US012735396B2

(12) United States Patent
Norman et al.

(10) Patent No.: US 12,735,396 B2
(45) **Date of Patent: *Sep. 15, 2026**

(54) DIHYDRO-CYCLOPENTA-ISOQUINOLINE

(71) Applicant: UCB Biopharma SRL, Brussels (BE)

(72) Inventors: Timothy John Norman, Slough (GB); Jag Paul Heer, Slough (GB); Oliver Philps, Abingdon (GB); William Ross Pitt, Slough (GB); James Madden, Abingdon (GB); Zeshan Yousuf, Abingdon (GB)

(73) Assignee: UCB Biopharma SRL, Brussels (BE)

( * ) Notice: Subject to any disclaimer, the term of this patent is extended or adjusted under 35 U.S.C. 154(b) by 1050 days.

This patent is subject to a terminal disclaimer.

(21) Appl. No.: 17/786,300

(22) PCT Filed: Dec. 22, 2020

(86) PCT No.: PCT/EP2020/087681

§ 371 (c)(1),
(2) Date: Jun. 16, 2022

(87) PCT Pub. No.: WO2021/130255

PCT Pub. Date: Jul. 1, 2021

(65) Prior Publication Data

US 2023/0192646 A1 Jun. 22, 2023

(30) Foreign Application Priority Data

Dec. 23, 2019 (GB) ..................................... 1919210

(51) Int. Cl.

| | |
|---|---|
| ***C07D 401/12*** | (2006.01) |
| ***C07D 215/06*** | (2006.01) |
| ***C07D 401/14*** | (2006.01) |
| ***C07D 405/14*** | (2006.01) |
| ***C07D 409/14*** | (2006.01) |
| ***C07D 413/14*** | (2006.01) |
| ***C07D 471/04*** | (2006.01) |

(52) U.S. Cl.

CPC ......... *C07D 401/12* (2013.01); *C07D 215/06* (2013.01); *C07D 401/14* (2013.01); *C07D 405/14* (2013.01); *C07D 409/14* (2013.01); *C07D 413/14* (2013.01); *C07D 471/04* (2013.01)

(58) Field of Classification Search

None

See application file for complete search history.

(56) References Cited

U.S. PATENT DOCUMENTS

| | | | | |
|---|---|---|---|---|
| 4,857,301 | A | 8/1989 | Czarniecki et al. | |
| 5,340,811 | A | 8/1994 | Kajihara et al. | |
| 12,410,161 | B2 | 9/2025 | Norman et al. | |
| 2007/0027184 | A1 | 2/2007 | Malecha et al. | |
| 2009/0156642 | A1 | 6/2009 | Nishida et al. | |
| 2023/0050670 | A1* | 2/2023 | Norman | C07D 401/12 |
| 2023/0303517 | A1* | 9/2023 | Norman | C07D 401/14 |
| 2024/0092773 | A1* | 3/2024 | Norman | C07D 413/14 |

FOREIGN PATENT DOCUMENTS

| | | | | | |
|---|---|---|---|---|---|
| CN | 1050183 | A | | 3/1991 | |
| EP | 0418071 | | | 3/1991 | |
| EP | 0 419 676 | | | 4/1991 | |
| EP | 0419676 | A1 | * | 4/1991 | C07C 323/21 |
| GB | 2270689 | | | 3/1994 | |
| JP | 2007 099676 | | | 4/2007 | |
| JP | 2007099676 | A | * | 4/2007 | |
| JP | 2017-501215 | | | 1/2017 | |
| WO | 1996/01643 | | | 1/1996 | |
| WO | 9828293 | | | 7/1998 | |
| WO | WO 2004/058709 | | | 7/2004 | |
| WO | WO-2004058709 | A1 | * | 7/2004 | A61P 37/08 |
| WO | 2008/059368 | | | 5/2008 | |

(Continued)

OTHER PUBLICATIONS

Search Report under Section 17 for Great Britian Patent Application No. GB1919210.3 dated Jun. 10, 2020, 2 pages.

(Continued)

*Primary Examiner* — Clinton A Brooks

*Assistant Examiner* — Nicola Maria Bauer

(74) *Attorney, Agent, or Firm* — McDonnell Boehnen Hulbert & Berghoff LLP

(57) ABSTRACT

The present invention relates to dihydro-cyclopenta-isoquinoline derivatives of formula (I), processes for preparing them, pharmaceutical compositions containing them and their use in treating disorders caused by IgE (such as allergic responses, non-allergic mast cell responses or certain autoimmune responses), and in particular disorders caused by the interaction of IgE with the FcεRI receptor.

(I)

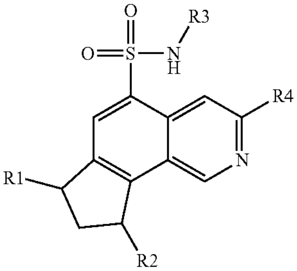

20 Claims, No Drawings

(56) References Cited

FOREIGN PATENT DOCUMENTS

| | | | | |
|---|---|---|---|---|
| WO | WO 2008/129276 | | 10/2008 | |
| WO | WO-2008129276 | A1 * | 10/2008 | ........... C07D 215/40 |
| WO | 2015/080707 | | 6/2015 | |
| WO | 2019/243550 | | 12/2019 | |
| WO | 2021/130257 | | 7/2021 | |
| WO | 2021/130259 | | 7/2021 | |
| WO | 2021/130260 | | 7/2021 | |
| WO | 2021/130262 | | 7/2021 | |

OTHER PUBLICATIONS

Parisi, Giuseppe Fabio et al. "Omalizumab treatment in a 12 year-old girl with chronic spontaneous urticaria" The Journal of Dermatological Treatment (2018) vol. 29(54), pp. 10-11 [available via https://www.tandfonline.comldoi/ full/10. 1080/09546634.2018. 1551609].

Sarkar Tarun K et al: "A Sequential Pummerer-Diels-Alder Route for the Generation and Trapping of Furo [3,4-c]pyridines: Synthesis of heterocyclic Analogues of 1-Arylnaphthalene Lignans", Journal of Organic Chemistry, vol. 68, No. 18, Sep. 1, 2003, pp. 6919-6927.

International Search Report dated Feb. 25, 2021 for International Application No. PCT/EP2020/087681, 3 pages.

Jun Kohno et al. "Production, Isolation and Biological Properties of TMC-120A, B and C, Novel Inhibitors of Eosinophil Survival from Aspergillus ustus TC 1118. Journal of Antibiotics" (1999) vol. 52(10), pp. 913-916.

Michael P Hay et al. "Tricyclic 1-18 [1,2,4]triazine 1,4-dioxides as hypoxia selective cytotoxins", Journal of Medicinal Chemistry (2008) vol. 51(21), pp. 6853-6865.

Kitagaki Shinji et al. "Intermolecular [4 + 2] Cycloaddition of o -Quinodimethanes Derived from Ene-Bis (sulfinylallenes)", Journal of Organic Chemistry (2006) vol. 71(18), pp. 6908-6914.

* cited by examiner

DIHYDRO-CYCLOPENTA-ISOQUINOLINE

CROSS-REFERENCE TO RELATED APPLICATIONS

This application is a U.S. national phase of International Application No. PCT/EP2020/087681, filed Dec. 22, 2020, which claims priority from Great Britain Application No. GB 1919210.3, filed Dec. 23, 2019, the disclosure of each of which is hereby incorporated by reference in its entirety.

TECHNICAL FIELD

The present invention relates to dihydro-cyclopenta-isoquinoline derivatives of formula (I), processes for preparing them, pharmaceutical compositions containing them and their use in treating disorders caused by IgE (such as allergic responses, non-allergic mast cell responses or certain auto-immune responses), and in particular disorders caused by the interaction of IgE with the FcεRI receptor.

BACKGROUND OF THE INVENTION

IgE (immunoglobulin E) is a member of the immunoglobulin family and mediates allergic responses such as asthma, food allergies, type 1 hypersensitivity and the familiar sinus inflammation. IgE is secreted by, and expressed on the surface of, B-cells. IgE synthesized by B-cells is anchored in the B-cell membrane by a transmembrane domain linked to the mature IgE sequence by a short membrane binding region. IgE also is bound to B-cells (and monocytes, eosinophils and platelets) through its Fc region to a low affinity IgE receptor (FcεRII). Upon exposure of a mammal to an allergen, B-cells are clonally amplified which synthesize IgE that binds the allergen. This IgE in turn is released into the circulation by the B-cells where it is bound by B-cells (through FcεRII) and by mast cells and basophils through the so-called high affinity receptor (FcεRI) found on the surface of the mast cells and basophils. Such mast cells and basophils are thereby sensitized for allergen. The next exposure to the allergen cross-links the FcεRI on these cells and thus activate their release of histamine and other factors which are responsible for clinical hypersensitivity and anaphylaxis.

Currently, allergic diseases, urticaria, and asthma are usually treated with one or more of the following drugs: (1) antihistamines and antileukotrienes which antagonize the inflammatory mediators histamine and leukotrienes, (2) local or systemic (oral or injectable) corticosteroids or immunosuppressants which suppress a broad spectrum of inflammatory mechanisms, (3) short or long-acting bronchodilators which relax smooth muscle of constricted airway in asthma, or (4) mast cell stabilizers which inhibit the degranulation of mast cells that is normally triggered by IgE-binding at FcεRI, (5) biologicals which prevent the binding of IgE at FcεRI. There has been also attempts to use peptides that modulate IgE binding to FcεRI. As an example, WO96/01643 describes peptides that consist of 4-50 amino to treat immediate allergic responses.

However, there is still a need to identify compounds which have therapeutic utility in the treatment or prevention of disorders caused by IgE, particularly disorders caused by the interaction of IgE with the FcεRI receptor.

SUMMARY OF THE INVENTION

It has been found that compounds of formula (I) and their pharmaceutically acceptable salts can be used for this purpose.

DETAILED DESCRIPTION

The present invention provides compounds of formula (I) and pharmaceutically acceptable salts thereof:

(I)

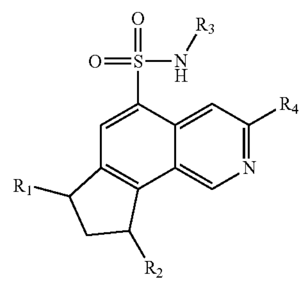

wherein

R1 represents:

Hydroxy;

Amino;

—NH—C(O)—$Ra^1$;

—NH—C(O)—NH—$Rb^1$;

—NH—C(O)—C1-6-alkanediyl-C(O)—C1-6-alkoxy optionally substituted with one or more aryl substituted with one or more halogen, —OH, C1-6-alkyl;

—NH—C(O)—C1-6-alkanediylC(O)-aryl optionally substituted with one or more hydroxy; halogen; C1-6-alkyl;

—NH—C(O)—C1-6-alkanediyl-NHC(O)-aryl optionally substituted with one or more hydroxy; halogen; C1-6-alkyl;

—NH—C(O)—C1-6-alkanediyl-aryloxy optionally substituted with one or more hydroxy; halogen; C1-6-alkyl;

—NH—C(O)—NH—C(O)O—C1-6-alkyl; —NH-Heteroaryl optionally substituted with one or more Halogen; C1-6-alkyl; C1-6-alkoxy; cyano; heteroaryl;

—NH—C(S)—NH-$Rc^1$;

—NH-Aryl optionally substituted with one or more Halogen; C1-6-alkyl; C1-6-alkoxy; cyano; heteroaryl;

—NH—C(O)O-$Rd^1$

—NH—C(N—CN)—NH—C1-6-alkyl;

Heteroaryl optionally substituted with one or more C1-6-alkyl; C1-6-alkylamino; heteroarylamino;

wherein $Ra^2$ represents

C1-6-alkyl optionally substituted with one or more group chosen amongst Aryl or Heteroaryl, optionally substituted with Halogen; C1-6-alkoxy; cyano;

Aryl optionally substituted with one or more Halogen; C1-6-alkyl; C1-6-alkoxy; C1-6-akylamino;

Heteroaryl optionally substituted with one or more Halogen; C1-6-alkyl, C1-6-alkoxy; cyano; heterocycloalkyl;

—C2-6-alkenediyl-aryl optionally substituted with one or more C1-6-alkyl; Halogen;
—R1'C(O)OR1" group, wherein R1" is alkyl and R1' is alkanediyl;
C3-8-cycloalkyl optionally substituted with one or more Halogen; C1-6-alkyl; C1-6-alkoxy; cyano;
C3-8-heterocycloalkyl optionally substituted with one or more Halogen; C1-6-alkyl; C1-6-alkoxy; cyano;
$Rb^2$ represents
C1-6-alkyl optionally substituted with aryl optionally substituted with one or more Halogen; C1-6-alkoxy; heteroaryl which is optionally substituted with one or more Halogen; C1-6-alkyl; C1-6-alkoxy;
C3-12-cycloalkyl optionally substituted with one or more C1-6-alkyl group; aryl; Aryl optionally substituted with one or more cyano;
C2-6-alkenediyl-aryl optionally substituted with one or more Halogen; C1-6-alkyl; —OH; Aryl substituted with one or more Halogen; C1-6-alkyl; —OH;
Heterorary optionally substituted with one or more Halogen; C1-6-alkyl; C1-6-alkoxy;
Heterocycloalkyl optionally substituted with one or more Halogen; C1-C6-alkoxy; cyano;
Amino;
$Rc^1$ represents
C1-6-alkyl;
Heteroaryl;
$Rd^1$ represents:
C1-6-alkyl;

R2 represents:
Hydroxy;
—NH—C(O)O—C1-6-Alkyl;
—NH—C(S)—NH—$Ra^2$;
—NH—C(O)—NH—$Rb^2$;
—NH-Aryl optionally substituted with one or more C1-6-alkoxy; C1-6-Alkylamino; heteroarylamino;
—NH—C1-6-Alkyl optionally substituted with one or more C1-6-alkyl; C1-6-alkoxy; cyano; aryl;
heteroaryl; C(O)O—C1-6-Alkyl group; C1-6-Alkylamino group; said substituent being optionally substituted with one or more hydroxy; halogen; oxo;
Heteroaryl optionally substituted with one or more heteroaryl; hydroxy; oxo; C1-6-alkyl; C1-6-alkylamino or heteroarylamino; said heteroaryl or heteroarylamino being optionally substituted with one or more group chosen amongst amino; C1-6-alkyl; C1-6-alkylamino;
—NH-Heteroaryl optionally substituted with one or more Halogen; C1-6-alkyl; C1-6-alkoxy; cyano; heteroaryl; C(O)OH; C(O)O—C1-6-Alkyl group; C1-6-Alkylamino group;
Aryl-C1-6-Alkylamino;
—C1-6-alkylamino;
—NH—C(O)—C1-6-alkyl;
—NH—CO-$Rc^2$;
—NH—C(O)—C2-6-alkenediyl-C(O)O—C1-6-Alkyl;
—NH—C(O)—C2-6-alkenediyl-aryl optionally substituted with one or more hydroxy; C1-6-alkyl; Halogen;
—NH—C(O)—C1-6-alkanediyl-heteroaryl optionally substituted with one or more oxo group;
—NH—C(O)—C1-6-alkanediyl-heterocycloalkyl optionally substituted with one or more oxo group;
—$NHSO_2$—C1-6-alkyl;
—$NHSO_2$—Heteroaryl optionally substituted with one or more Halogen; C1-6-alkyl; C1-6-alkoxy; C(O)OH group;
—NH—C(S)—NH—C1-6-Alkyl;
—$NHSO_2$—C1-6-alkoxy optionally substituted with one or more Halogen group;
—NH—C(N—CN)—NH—C1-6-alkyl;
Amino group;
$Ra^2$ represents
Heteroaryl;
C1-6-alkyl;
$Rb^2$ represents
C1-6-alkyl optionally substituted with one or more aryl; alkoxy-Aryl; heteroaryl optionally substituted with one or more C1-6-alkyl;
Heteroaryl optionally substituted with one or more Halogen; C1-6-alkyl; C1-6-alkoxy; cyano;
Cycloalkyl optionally substituted with one or more Halogen; C1-6-alkyl, C1-6-alkoxy; cyano; aryl;
C1-6-alkanediyl-C(O)O—C1-6-alkyl;
Heterocycloalkyl;
Aryl optionally substituted with one or more Halogen; C1-6-alkyl; C1-6-alkoxy; cyano; C1-6-alkyl-C(O)O—C1-6-alkyl;
$Rc^2$ represents
C1-6-alkyl;
C3-8-cycloalkyl;
C3-8-heterocycloalkyl;
Aryl optionally substituted with one or more C1-6-alky; C1-6-alkylamino;
Heteroaryl optionally substituted with one or more Halogen; C1-6-alkyl; C1-6-alkoxy; cyano; heterocycloalkyl; Aryl; amino;
C2-6-alkenediyl-Aryl optionally substituted with one or more Halogen; C1-6-alkyl; —OH;
C2-6-alkanediyl-Heterocyloalkyl optionally substituted with one or more C1-6-alkyl; —OH;
C2-6-alkanediyl-C1-6-alkoxy group optionally substituted with one oxo group;

R3 represents a group chosen amongst:
C1-6-alkyl optionally substituted with one or more group chosen amongst $R3^a$;
C1-3-alkanediyl-C3-6-cycloalkyl optionally substituted with one or more $R3^a$;
C1-3-alkanediyl-C3-6-heterocycloalkyl optionally substituted with one or more $R3^a$;
C3-6-heterocycloalkyl optionally substituted with one or more $R3^a$;
C3-6-cycloalkyl optionally substituted with one or more $R3^a$;
$R3^a$ represents a group chosen amongst hydrogen Halogen, C1-2-alkyl; hydroxy; C1-2-alkoxy R4 represents a group chosen amongst:
C3-6-cycloalkyl optionally substituted with one or more $R4^a$ group; or C1-6-alkanediyl-C3-6-cycloalkyl optionally substituted with one or more $R4^a$ group; or C1-6-alkanediyl-C3-6-heterocycloalkyl optionally substituted with one or more $R4^a$ group;
$R4^a$ represents a group chosen amongst hydroxy; Halogen; C1-2-alkyl.

The compounds of formula (I) may contain one or more asymmetric carbon atoms. They can therefore exist as enantiomers or diastereoisomers. These enantiomers, diastereoisomers, and mixtures thereof, include racemic mixtures, forming part of the invention.

The compounds of formula (I) may exist in the form of bases or addition salts with acids. Such addition salts are part of the invention. These salts are advantageously prepared with pharmaceutically acceptable acids. Salts of other acids that are useful, for example, for the purification or the isolation of the compounds of formula (I) are also part of the present invention.

The term "pharmaceutically acceptable salt" according to the invention embraces salts of the compounds of formula (I) with a pharmaceutically acceptable acid or base, in particular an acid addition salt. The acid addition salt form of a compound of formula (I) that occurs in its free form as a base can be obtained by treating the free base with an appropriate acid such as an inorganic acid, for example, a hydrohalic acid such as hydrochloric acid or hydrobromic acid, sulfuric acid, nitric acid, phosphoric acid and the like; or an organic acid, such as, for example, acetic acid, trifluoroacetic acid, oxalic acid, hydroxyacetic acid, propanoic acid, lactic acid, pyruvic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and the like.

The invention also relates to all stereoisomeric forms such as enantiomeric and diastereoisomeric forms of the compounds of formula (I) or mixtures thereof (including all possible mixtures of stereoisomers such as racemates). With respect to the present invention reference to a compound or compounds is intended to encompass that compound in each of its possible isomeric forms and mixtures thereof, unless the particular isomeric form is referred to specifically.

Some of the compounds of formula (I) may also exist in tautomeric forms. Such forms although not explicitly indicated in the above formula are intended to be included within the scope of the present invention.

It is to be understood that each individual atom present in formula (I), or in formulae depicted herein, may in fact be present in the form of any of its naturally occurring isotopes, with the most abundant isotope(s) being preferred. Thus, by way of example, each individual hydrogen atom present in formula (I), or in the formulae depicted herein, may be present as a 1H, 2H (deuterium) or 3H (tritium) atom, preferably 1H. Similarly, by way of example, each individual carbon atom present in formula (I), or in the formulae depicted herein, may be present as a 12C, 13C or 14C atom, preferably 12C.

The present invention includes within its scope solvates of the compounds of formula (I) above.

Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see Pharmaceutical Salts and Co-crystals, ed. J. Wouters & L. Quere, RSC Publishing, 2012).

Compounds according to the present invention may exist in different polymorphic forms. Although not explicitly indicated in the above formula, such forms are intended to be included within the scope of the present invention.

The present invention also includes within its scope prodrug of the compounds of formula (I) above.

The term "prodrug" means a compound metabolised in vivo to a compound of the invention or its salt. A prodrug may be identified by administering the prodrug to a mammal, such as rat, mouse, monkey or man, and identifying the compound or its salt, for example in blood or urine.

Another embodiment of the present invention concerns a pharmaceutical composition comprising a detectable amount of a compound of formula (I) or a pharmaceutically acceptable salt, solvate or co-crystal thereof in combination with a pharmaceutically acceptable diluent or carrier.

In yet another embodiment, the present invention concerns a compound of formula (I) a pharmaceutically acceptable salt, solvate or co-crystal thereof for use as a medicament, in particular for use in a method for the treatment or prevention of disorders caused by IgE, including allergy, type 1 hypersensitivity, familiar sinus inflammation, urticaria or related conditions, such as airway constriction in asthma, local inflammation in eczema, increased mucus secretion in allergic rhinitis, increased vascular permeability, eosinophilic granulomatosis with polyangiitis (also known as "Churg Strauss syndrome"), aspirin exacerbated respiratory disease, or cutaneous T-cell lymphoma.

In a further embodiment, the present invention concerns a method for the treatment or prevention of allergy, type 1 hypersensitivity, familiar sinus inflammation, urticaria or related conditions, which comprises the administration of a compound of formula (I) in a therapeutically effective amount.

In the frame of the present invention:

Ct-z represents a carbon chain which may have from t to z carbon atoms, for example C1-7 a carbon chain which may have from 1 to 7 carbon atoms;

Alkyl is a saturated, linear or branched aliphatic group; for example, a C1-6-alkyl group represents a carbon chain of 1 to 6 carbon atoms, linear or branched, for example a methyl, ethyl, propyl, isopropyl, butyl, isobutyl, tertbutyl, pentyl, hexyl. Alkyl encompass deuterated groups, where one or more hydrogen atoms are replaced with deuterium atom $^2H$.

Alkanediyl is a divalent linear or branched saturated hydrocarbon group of general formula $C_nH_{2n}$ such as $—CH_2—CH_2—$;

Alkenediyl is a divalent linear or branched unsaturated hydrocarbon group showing at least one double bond, such as —CH═CH—:

Alkylamino refers to one or more alkyl groups substituted on an amino radical. As examples of alkylamino one can mention methylamino; ethylamino; tertbutylamino; dimethylamino;

acyl, an alkyl-C(O)— group;

oxo, a ═O group hydroxy is a —OH group;

hydroxyalkyl is an alkyl group of which one or more hydrogen atom has been substituted with a hydroxy group;

alkoxy, —O-alkyl group;

alkylthio, a —S-alkyl group;

halogen atom, a fluorine, chlorine, bromine or iodine atom;

cycloalkyl refers to a mono or bicyclic saturated aliphatic group comprising between 3 and 14 atoms, preferably 3 to 9 atoms in the group. As an example of cycloalkyl one can mention cyclopropyl; cyclobutyl; cyclopentyl; cyclohexyl; spiro-undecanyl; spiro[2.2]pentanyl;

heterocycloalkyl refers to a mono or bicyclic saturated group comprising between 3 and 14 atoms in the group and wherein one or more carbon atom is replaced with an atom chosen amongst nitrogen; oxygen; sulfur. As an example of heterocycloalkyl one can mention aziridinyl; pyrrolidinyl. piperidyl; oxetane; oxa-spiro-undecanyl;

aryl refers to a mono- or bicyclic aromatic group comprising between 6 and 10 carbon atoms wherein at least one ring in the group is an aromatic group. As examples of an aryl group one can mention phenyl or naphthyl groups;

Heteroaryl refers to a mono- or bicyclic group comprising from 5 to 14 atoms, preferably 5 to 9 atoms wherein at least one ring in the group is aromatic and wherein at least one atom in the group is chosen amongst nitrogen; oxygen; sulfur. As examples of a heteroaryl group one can mention triazolyl, furanyl; pyrrolyl; chromanyl; isoquinolinyl;

Arylamino refers to an amino group —NH2 substituted with an aryl group. Example of arylamino can be anilino;

Heteroarylamino refers to an amino group —NH2 substituted with a heteroaryl group. Example of heteroaryl group can be pyridinylamino;

Aryloxy refers to an —O-aryl group. As an example of aryloxy one can cite phenoxy.

According to an embodiment, compounds of the invention are characterized by the formula wherein R4 represents cyclopropyl or spiro[2.2]pentanyl; optionally substituted with one or more group chosen independently from hydroxy; Chloro, Fluoro, Bromo; Methyl.

According to an embodiment, compounds of the invention are characterized by the formula wherein wherein R4 represents cyclopropyl.

According to an embodiment, compounds of the invention are characterized by the formula wherein R1 and R2 represent independently from each other —NH—CO—$Ra^1$ and $Ra^1$ represents Heteroaryl optionally substituted with one or more Halogen; C1-6-alkyl, C1-6-alkoxy; cyano; heterocycloalkyl; aryl; or —NH-heteroaryl optionally substituted with one or more Halogen; C1-6-alkyl, C1-6-alkoxy; cyano; heterocycloalkyl; aryl.

According to an embodiment compounds of the invention are characterized by the formula wherein wherein R1 represents:

hydroxy; pyridine-carbonylamino; ethylcarbamoylamino; (methoxyphenyl)methylcarbamoylamino; [(bromphenyl)methyl]carbamoylamino; naphthalenylcarbamoylamino; (methyl-xazolyl)methyl]carbamoylamino; ethoxycarbonyl-carbamoylamino; [(methoxyphenyl)ethyl]carbonylamino; (cyclopropylethyl)carbamoylamino; (methyl)cyclopropyl]carbamoylamino; (benzyl)carbamoylamino; (phenyl-cyclopropyl)carbamoylamino; (chromanyl)carbamoylamino; (chlorophenyl)propenoyl]amino; (methoxypyridine-carbonyl)amino; [(methoxy-oxo-propanoyl)amino]; (benzamidoacetyl)amino; (chloro-methoxy-thiophene-carbonyl)amino; (ethoxy-oxo-propanoyl)amino; methylbutanoylamino; [(chlorophenoxy)acetyl]amino; (methoxypyridinyl)amino; amino; benzimidazolylamino; ethylcarbamothioylamino; (pyridinyl-triazolyl)amino; [(ethyl-triazolyl)amino; (ethylamino)-triazolyl; ethylcarbamoylamino; (methyl-oxadiazolyl)anilino; tert-butoxycarbonylamino; [N'-cyano-N-ethylcarbamimidoyl]amino; pyridin-3-yl-carbamoylamino; propan-2-yl-carbamoylamino; (5-methylpyridine-3-carbonyl)amino; (6-morpholin-4-ylpyridine-3-carbonyl)amino; benzamido; [(dimethylamino)benzoyl]amino; Dimethylbutanoylamino.

According to an embodiment compounds of the invention are characterized by the formula wherein R1 represents:

Hydroxy; pyridine-3-carbonylamino; ethylcarbamoylamino; (4-methoxyphenyl)methylcarbamoylamino; (3-cyanophenyl)carbamoylamino; [(4-bromphenyl)methyl]carbamoylamino; naphthalen-1-ylcarbamoylamino; [(5-methyl-1,2-oxazol-3-yl)methyl]carbamoylamino; ethoxycarbonyl-carbamoylamino; [(1R)-1-(3-methoxyphenyl)ethyl]carbonylamino; (1-cyclopropylethylcarbamoylamino); 2-(methyl)cyclopropyl]carbamoylamino; (1-benzyl)carbamoylamino; (2-phenyl-cyclopropyl)carbamoylamino; (chroman-3-yl)carbamoylamino; (E)-3-(2-chlorophenyl)prop-2-enoyl]amino; (6-methoxypyridine-3-carbonyl)amino; [(3-methoxy-3-oxo-propanoyl)amino]; (2-benzamidoacetyl)amino; (5-chloro-4-methoxy-thiophene-3-carbonyl)amino; (3-ethoxy-3-oxo-propanoyl)amino; 2-methylbutanoylamino; [2-(4-chlorophenoxy)acetyl]amino; (5-methoxypyridin-3-yl)amino; amino; 1H-benzimidazol-2-ylamino; ethylcarbamothioylamino; (4-pyridin-3-yl-1,2,4-triazol-3-yl)amino; 3-(ethylamino)-1,2,4-triazol-4-yl; 3-(5-methyl-1,3,4-oxadiazol-2-yl)anilino; tert-butoxycarbonylamino; [(Z)—N'-cyano-N-ethyl-carbamimidoyl]amino; propan-2-ylcarbamoylamino; pyridin-3-ylcarbamothioylamino; (5-methylpyridine-3-carbonyl)amino; 6-morpholin-4-ylpyridine-3-carbonyl)amino; benzamido; [4-(dimethylamino)benzoyl]amino; 3,3-dimethylbutanoylamino.

According to an embodiment compounds of the invention are characterized by the formula wherein R2 represents:

tert-butoxycarbonyl-amino; amino; pyridylcarbamothioylamino; ethylcarbamoylamino; pyridinyl-amino; (pyridinyl-triazolyl)amino; (pyridinyl-amino)-triazolyl; (ethyl-triazolyl)amino; benzylamino; propylamino; methylpropanoylamino; hydroxy; ethylcarbamoylamino; isoquinolinyl-amino; (methoxypyridinyl)amino; (pyridinyl)carbonylamino; benzimidazolylamino; [(phenyl)-oxazolyl]carbonylamino; quinoxaline-carbonylamino; [(hydroxyphenyl)propenoyl]amino; pyrido-pyrazine-carbonylamino; benzoxazole-carbonylamino; [ethoxy-oxo-butenoyl]amino; (benzimidazolyl)propanoylamino; (oxopyridinyl)propanoylamino; methoxy-benzofuran-carbonyl)amino; (oxopyrrolidinyl)propanoylamino; [(ethoxycarbonyl-pyridyl)amino]; (methoxyanilino); (cyano-pyridyl)amino; [(methyl-pyridazinyl)amino]; quinolinyl-amino; (methyl-oxazolyl)methyl-carbamoyl-amino; (phenylcyclopropyl)carbamoylamino; [(tert-butoxymethyl-oxo-ethyl)carbamoylamino]; dihydro-2H-chromenylcarbamoylamino; [(methoxyphenyl)ethylcarbamoylamino]; oxanylcarbamoylamino; (chloro-methylphenyl)carbamoylamino; methanesulfonamido; methylpropylsulfonylamino; pyridinylsulfonylamino; [(carboxypyridyl)amino]; pyridylcarbamoylamino; methoxy-pyridinyl)amino; ethyl-carbamothioyl-amino; (pyridinyl-triazolyl)amino; (methoxy-pyridinyl)amino; [(ethyl-triazolyl)amino; (ethylamino)-triazolyl; (methyl-oxadiazolyl)anilino; trichloroethoxysulfonylamino; [(Z)—N'-cyano-N-ethyl-carbamimidoyl]amino; pyridinylcarbamoylamino; propanylcarbamoylamino; pyridinylcarbamothioylamino; methylpyridinecarbonyl)amino; (morpholinylpyridinecarbonyl)amino; Benzamido; [(dimethylamino)benzoyl]amino; dimethylbutanoylamino.

According to an embodiment compounds of the invention are characterized by the formula wherein R2 represents:

tert-butoxycarbonyl-amino; amino; 3-pyridylcarbamothioylamino; ethylcarbamoylamino; pyridine-3-ylamino; (4-pyridin-3-yl-1,2,4-triazol-3-yl)amino; 3-(pyridin-3-ylamino)-1,2,4-triazol-4-yl; (4-ethyl-1,2,4-triazol-3-yl)amino; benzylamino; propylamino; 2-methylpropanoylamino; hydroxy; ethylcarbamoylamino; isoquinolin-4-ylamino; (5-methoxypyridin-3-yl)amino; (pyridine-3-I)carbonylamino; 1H-benzimidazol-2-ylamino; [3-(phenyl)-1,2-oxazol-5-yl]carbonylamino; quinoxaline-6-carbonylamino; [3-(4-hydroxyphenyl)prop-2-enoyl]amino; pyrido[2,3-b]pyrazine-7-carbonylamino; 1,3-benzoxazole-2-carbonylamino; [(E)-4-ethoxy-4-oxo-but-2-enoyl]amino; 3-(benzimidazol-1-yl)propanoylamino; 3-(2-oxopyridin-1-yl)propanoylamino; 4-methoxy-1-benzofuran-2-carbonyl)amino; 3-(2-oxopyrrolidin-1-yl)propanoylamino; [(5-ethoxycarbonyl-3-pyridyl)amino]; (2-methoxyanilino); (4-cyano-2-pyridyl)amino; [(6-methylpyridazin-3-yl)amino]; quinolin-4-ylamino; (5-methyl-1,2-oxazol-3-yl)methylcarbamoylamino; (2-phenylcyclopropyl)carbamoylamino; [(2-tert-butoxy-1-methyl-2-oxo-ethyl)carbamoylamino]; 3,4-dihydro-2H-chromen-3-ylcarbamoylamino; [1-(3-methoxyphenyl)ethylcarbamoylamino]; oxan-4-ylcarbamoylamino; (2-chloro-6-methylphenyl)carbamoylamino; methanesulfonamido; 2-methylpropylsulfonylamino; pyridin-3-ylsulfonylamino; [(5-carboxy-3-pyridyl)amino]; 3-pyridylcarbamoylamino; 5-methoxypyridin-3-yl)amino; ethylcarbamothioylamino; (4-pyridin-3-yl-1,2,4-triazol-3-yl)amino; (5-methoxypyridin-3-yl)amino; [(4-ethyl-1,2,4-triazol-3-yl)amino; 3-(ethylamino)-1,2,4-triazol-4-yl; 3-(5-methyl-1,3,4-oxadiazol-2-yl)anilino; 2,2,2-trichloroethoxysulfonylamino; [(Z)—N'-cyano-N-ethyl-carbamimidoyl]amino; pyridin-3-ylcarbamoylamino; propan-2-ylcarbamoylamino; pyridin-3-ylcarbamothioylamino; 5-methylpyridine-3-carbonyl)amino; (6-morpholin-4-ylpyridine-3-carbonyl)amino; Benzamido; [4-(dimethylamino)benzoyl]amino; 3,3-dimethylbutanoylamino.

According to an embodiment compounds of the invention are chosen amongst the following: tert-butyl N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]carbamate;

tert-butyl N-[cis-(7RS,9SR)-3-cyclopropyl-5-(2-methylpropylsulfamoyl)-7-(pyridine-3-carbonylamino)-8,9-dihydro-7H-cyclopenta[h]isoquinolin-9-yl]carbamate;

N-[trans-(7RS,9RS)-9-amino-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(pyridin-3-ylcarbamothioylamino)-8,9-dihydro-7H-cyclopenta[h]isoquinolin-7-yl]pyridine-3-carboxamide;

N-[trans-(7RS,9RS)-3-cyclopropyl-9-(ethylcarbamoylamino)-5-(2-methylpropylsulfamoyl)-8,9-dihydro-7H-cyclopenta[h]isoquinolin-7-yl]pyridine-3-carboxamide;

N-[cis-(7RS,9SR)-3-cyclopropyl-5-(2-methylpropylsulfamoyl)-9-(pyridin-3-ylamino)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(pyridin-3-ylamino)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[(4-pyridin-3-yl-1,2,4-triazol-3-yl)amino]-8,9-dihydro-7H-cyclopenta[h]isoquinolin-7-yl]pyridine-3-carboxamide;

N-[trans-(7RS,9RS)-3-cyclopropyl-5-(2-methyl propylsulfamoyl)-9-[3-(pyridin-3-ylamino)-1,2,4-triazol-4-yl]-8,9-dihydro-7H-cyclopenta[h]isoquinolin-7-yl]pyridine-3-carboxamide;

N-[trans-(7RS,9RS)-3-cyclopropyl-9-[(4-ethyl-1,2,4-triazol-3-yl)amino]-5-(2-methylpropylsulfamoyl)-8,9-dihydro-7H-cyclopenta[h]isoquinolin-7-yl]pyridine-3-carboxamide;

N-[trans-(7RS,9RS)-9-(benzylamino)-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(propylamino)-8,9-dihydro-7H-cyclopenta[h]isoquinolin-7-yl]pyridine-3-carboxamide;

N-[trans-(7RS,9RS)-3-cyclopropyl-9-(2-methylpropanoylamino)-5-(2-methylpropylsulfamoyl)-8,9-dihydro-7H-cyclopenta[h]isoquinolin-7-yl]pyridine-3-carboxamide;

1-ethyl-3-[trans-(7RS,9RS)-3-cyclopropyl-9-hydroxy-5-(2-methylpropylsulfamoyl)-8,9-dihydro-7H-cyclopenta[h]isoquinolin-7-yl]urea;

1-ethyl-3-[cis-(7RS,9SR)-3-cyclopropyl-9-hydroxy-5-(2-methylpropylsulfamoyl)-8,9-dihydro-7H-cyclopenta[h]isoquinolin-7-yl]urea 1-ethyl-3-[trans-(7RS,9RS)-3-cyclopropyl-7-hydroxy-5-(2-methylpropylsulfamoyl)-8,9-dihydro-7H-cyclopenta[h]isoquinolin-9-yl]urea;

N-[cis-(7RS,9SR)-3-cyclopropyl-9-(isoquinolin-4-ylamino)-5-(2-methylpropylsulfamoyl)-8,9-dihydro-7H-cyclopenta[h]isoquinolin-7-yl]pyridine-3-carboxamide;

1-[(4-methoxyphenyl)methyl]-3-[trans-(7RS,9RS)-3-cyclopropyl-9-[(5-methoxypyridin-3-yl)amino]-5-(2-methylpropylsulfamoyl)-8,9-dihydro-7H-cyclopenta[h]isoquinolin-7-yl]urea;

N-[trans-(7RS,9RS)-7-[(3-cyanophenyl)carbamoylamino]-3-cyclopropyl-5-(2-methylpropylsulfamoyl)-8,9-dihydro-7H-cyclopenta[h]isoquinolin-9-yl]pyridine-3-carboxamide;

N-[trans-(7RS,9RS)-7-[(4-bromophenyl)methylcarbamoylamino]-3-cyclopropyl-5-(2-methylpropylsulfamoyl)-8,9-dihydro-7H-cyclopenta[h]isoquinolin-9-yl]pyridine-3-carboxamide;

N-[trans-(7RS,9RS)-3-cyclopropyl-5-(2-methylpropylsulfamoyl)-7-(naphthalen-1-ylcarbamoylamino)-8,9-dihydro-7H-cyclopenta[h]isoquinolin-9-yl]pyridine-3-carboxamide;

1-[(5-methyl-1,2-oxazol-3-yl)methyl]-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea; Ethyl N-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]carbamoyl]carbamate;

1-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]-3-[rac-(1S)-1-(3-methoxyphenyl)ethyl]urea;

1-(1-cyclopropylethyl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

1-(2-methylcyclopropyl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

1-benzyl-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

1-(2-phenylcyclopropyl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

1-(3,4-dihydro-2H-chromen-3-yl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

N-[trans-(7RS,9RS)-3-cyclopropyl-5-(2-methylpropylsulfamoyl)-7-[[rac-(E)-3-(2-chlorophenyl)prop-2-enoyl]amino]-8,9-dihydro-7H-cyclopenta[h]isoquinolin-9-yl]pyridine-3-carboxamide;

6-methoxy-N-[trans-(7RS,9RS)-3-cyclopropyl-5-(2-methylpropylsulfamoyl)-9-(pyridine-3-carbonylamino)-8,9-dihydro-7H-cyclopenta[h]isoquinolin-7-yl]pyridine-3-carboxamide;

methyl 3-oxo-3-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]amino]propanoate N-[2-oxo-2-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]amino]ethyl]benzamide;

5-chloro-4-methoxy-N-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]thiophene-3-carboxamide;

ethyl 3-oxo-3-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]amino]propanoate;

N-[cis-(7RS,9SR)-3-cyclopropyl-7-(2-methylbutanoylamino)-5-(2-methylpropylsulfamoyl)-8,9-dihydro-7H-cyclopenta[h]isoquinolin-9-yl]pyridine-3-carboxamide;

N-[cis-(7RS,9SR)-7-[[2-(4-chlorophenoxy)acetyl]amino]-3-cyclopropyl-5-(2-methylpropylsulfamoyl)-8,9-dihydro-7H-cyclopenta[h]isoquinolin-9-yl]pyridine-3-carboxamide;

3-phenyl-N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]-1,2-oxazole-5-carboxamide;

N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]quinoxaline-6-carboxamide;

N-[trans-(7RS,9RS)-3-cyclopropyl-5-(2-methylpropylsulfamoyl)-9-[[rac-(E)-3-(4-hydroxyphenyl)prop-2-enoyl]amino]-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]pyrido[2,3-b]pyrazine-7-carboxamide;

N-[trans-(7RS,9RS)-3-cyclopropyl-5-(2-methylpropylsulfamoyl)-7-(pyridine-3-carbonylamino)-8,9-50 dihydro-7H-cyclopenta[h]isoquinolin-9-yl]-1,3-benzoxazole-2-carboxamide;

ethyl rac-(E)-4-oxo-4-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]amino]but-2-enoate;

N-[trans-(7RS,9RS)-9-[3-(benzimidazol-1-yl)propanoylamino]-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[3-(2-oxopyridin-1-yl)propanoylamino]-8,9-dihydro-7H-cyclopenta[h]isoquinolin-7-yl]pyridine-3-carboxamide;

N-[trans-(7RS,9RS)-3-cyclopropyl-9-[(4-methoxy-1-benzofuran-2-carbonyl)amino]-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[3-(2-oxopyrrolidin-1-yl)propanoylamino]-8,9-dihydro-7H-cyclopenta[h]isoquinolin-7-yl]pyridine-3-carboxamide;

ethyl 5-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]amino]pyridine-3-carboxylate;

N-[trans-(7RS,9RS)-3-cyclopropyl-9-(2-methoxyanilino)-5-(2-methylpropylsulfamoyl)-8,9-dihydro-7H-cyclopenta[h]isoquinolin-7-yl]pyridine-3-carboxamide;

N-[trans-(7RS,9RS)-9-[(4-cyanopyridin-2-yl)amino]-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[(6-methylpyridazin-3-yl)amino]-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(quinolin-4-ylamino)-8,9-dihydro-7H-cyclopenta[h]isoquinolin-7-yl]pyridine-3-carboxamide;

N-[trans-(7RS,9RS)-3-cyclopropyl-9-[(5-methyl-1,2-oxazol-3-yl)methylcarbamoylamino]-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[(2-phenylcyclopropyl)carbamoylamino]-8,9-dihydro-7H-cyclopenta[h]isoquinolin-7-yl]pyridine-3-carboxamide;

tert-butyl 2-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]carbamoylamino]propanoate;

N-[trans-(7RS,9RS)-3-cyclopropyl-9-(3,4-dihydro-2H-chromen-3-ylcarbamoylamino)-5-(2-methylpropylsulfamoyl)-8,9-dihydro-7H-cyclopenta[h]isoquinolin-7-yl]pyridine-3-carboxamide;

N-[trans-(7SR,9SR)-3-cyclopropyl-5-(2-methylpropylsulfamoyl)-9-[[rac-(1R)-1-(3-methoxyphenyl)ethyl]carbamoylamino]-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(oxan-4-ylcarbamoylamino)-8,9-dihydro-7H-cyclopenta[h]isoquinolin-7-yl]pyridine-3-carboxamide;

N-[trans-(7RS,9RS)-9-[(2-chloro-6-methylphenyl)carbamoylamino]-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-9-(methanesulfonamido)-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(2-methylpropylsulfonylamino)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(pyridin-3-ylsulfonylamino)-8,9-dihydro-7H-cyclopenta[h]isoquinolin-7-yl]pyridine-3-carboxamide;

5-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]amino]pyridine-3-carboxylic acid;

1-pyridin-3-yl-3-[cis-(7RS,9SR)-3-cyclopropyl-5-(2-methylpropylsulfamoyl)-7-(pyridin-3-ylcarbamoylamino)-8,9-dihydro-7H-cyclopenta[h]isoquinolin-9-yl]urea;

cis-(7RS,9SR)-3-cyclopropyl-7,9-bis[(5-methoxypyridin-3-yl)amino]-N-(2-methylpropyl)-8,9-dihydro-7H-cyclopenta[h]isoquinoline-5-sulfonamide;

cis-(7RS,9SR)-7-amino-3-cyclopropyl-9-[(5-methoxypyridin-3-yl)amino]-N-(2-methylpropyl)-8,9-dihydro-7H-cyclopenta[h]isoquinoline-5-sulfonamide;

cis-(7RS,9SR)-7,9-bis(1H-benzimidazol-2-ylamino)-3-cyclopropyl-N-(2-methylpropyl)-8,9-dihydro-7H-cyclopenta[h]isoquinoline-5-sulfonamide;

1-ethyl-3-[cis-(7RS,9SR)-3-cyclopropyl-7-(ethylcarbamothioylamino)-5-(2-methylpropylsulfamoyl)-8,9-dihydro-7H-cyclopenta[h]isoquinolin-9-yl]thiourea;

cis-(7RS,9SR)-3-cyclopropyl-N-(2-methylpropyl)-7,9-bis[(4-pyridin-3-yl-1,2,4-triazol-3-yl)amino]-8,9-dihydro-7H-cyclopenta[h]isoquinoline-5-sulfonamide;

trans-(7RS,9RS)-3-cyclopropyl-7,9-bis[(5-methoxypyridin-3-yl)amino]-N-(2-methylpropyl)-8,9-dihydro-7H-cyclopenta[h]isoquinoline-5-sulfonamide;

trans-(7RS,9RS)-7,9-bis(1H-benzimidazol-2-ylamino)-3-cyclopropyl-N-(2-methylpropyl)-8,9-dihydro-7H-cyclopenta[h]isoquinoline-5-sulfonamide;

trans-(7RS,9RS)-3-cyclopropyl-7,9-bis[(4-ethyl-1,2,4-triazol-3-yl)amino]-N-(2-methylpropyl)-8,9-dihydro-7H-cyclopenta[h]isoquinoline-5-sulfonamide;

trans-(7RS,9RS)-3-cyclopropyl-7,9-bis[3-(ethylamino)-1,2,4-triazol-4-yl]-N-(2-methylpropyl)-8,9-dihydro-7H-cyclopenta[h]isoquinoline-5-sulfonamide;

1-ethyl-3-[trans-(7RS,9RS)-3-cyclopropyl-7-(ethylcarbamoylamino)-5-[(2-fluoro-2-methylpropyl)sulfamoyl]-8,9-dihydro-7H-cyclopenta[h]isoquinolin-9-yl]urea;

trans-(7RS,9RS)-3-cyclopropyl-7,9-bis[3-(5-methyl-1,3,4-oxadiazol-2-yl)anilino]-N-(2-methylpropyl)-8,9-dihydro-7H-cyclopenta[h]isoquinoline-5-sulfonamide;

tert-butyl N-[trans-(7RS,9RS)-3-cyclopropyl-5-(2-methylpropylsulfamoyl)-9-(2,2,2-trichloroethoxysulfonylamino)-8,9-dihydro-7H-cyclopenta[h]isoquinolin-7-yl]carbamate;

2-cyano-1-ethyl-3-[trans-(7RS,9RS)-3-cyclopropyl-5-(2-methylpropylsulfamoyl)-7-[[rac-(E)-N'-cyano-N-ethyl-carbamimidoyl]amino]-8,9-dihydro-7H-cyclopenta[h]isoquinolin-9-yl]guanidine;

1-ethyl-3-[cis-(7RS,9SR)-3-cyclopropyl-7-(ethylcarbamoylamino)-5-[(2-fluoro-2-methylpropyl)sulfamoyl]-8,9-dihydro-7H-cyclopenta[h]isoquinolin-9-yl]urea;

1-pyridin-3-yl-3-[trans-(7RS,9RS)-3-cyclopropyl-5-(2-methylpropylsulfamoyl)-7-(pyridin-3-ylcarbamoylamino)-8,9-dihydro-7H-cyclopenta[h]isoquinolin-9-yl]urea;

1-propan-2-yl-3-[trans-(7RS,9RS)-3-cyclopropyl-5-(2-methylpropylsulfamoyl)-7-(propan-2-ylcarbamoylamino)-8,9-dihydro-7H-cyclopenta[h]isoquinolin-9-yl]urea;

1-pyridin-3-yl-3-[trans-(7RS,9RS)-3-cyclopropyl-5-(2-methylpropylsulfamoyl)-7-(pyridin-3-ylcarbamothioylamino)-8,9-dihydro-7H-cyclopenta[h]isoquinolin-9-yl]thiourea;

5-methyl-N-[trans-(7RS,9RS)-3-cyclopropyl-5-(2-methylpropylsulfamoyl)-9-[(5-methylpyridine-3-carbonyl)amino]-8,9-dihydro-7H-cyclopenta[h]isoquinolin-7-yl]pyridine-3-carboxamide;

6-morpholin-4-yl-N-[trans-(7RS,9RS)-3-cyclopropyl-5-(2-methylpropylsulfamoyl)-9-[(6-morpholin-4-ylpyridine-3-carbonyl)amino]-8,9-dihydro-7H-cyclopenta[h]isoquinolin-7-yl]pyridine-3-carboxamide;

N-[trans-(7RS,9RS)-9-benzamido-3-cyclopropyl-5-(2-methylpropylsulfamoyl)-8,9-dihydro-7H-cyclopenta[h]isoquinolin-7-yl]benzamide;

4-(dimethylamino)-N-[trans-(7RS,9RS)-3-cyclopropyl-9-[[4-(dimethylamino)benzoyl]amino]-5-(2-methylpropylsulfamoyl)-8,9-dihydro-7H-cyclopenta[h]isoquinolin-7-yl]benzamide;

3,3-dimethyl-N-[trans-(7RS,9RS)-3-cyclopropyl-9-(3,3-dimethylbutanoylamino)-5-(2-methylpropylsulfamoyl)-8,9-dihydro-7H-cyclopenta[h]isoquinolin-7-yl]butanamide; N,N'-(trans-(7RS,9RS)-3-cyclopropyl-5-(N-isobutylsulfamoyl)-8,9-dihydro-7H-cyclopenta[h]isoquinoline-7,9-diyl)diacetamide;

N-[3-cyclopropyl-5-[(2-fluoro-2-methylpropyl)sulfamoyl]-9-(pyridine-3-carbonylamino)-8,9-dihydro-7H-cyclopenta[h]isoquinolin-7-yl]pyridine-3-carboxamide;

N-[9-amino-3-cyclopropyl-5-[(2-fluoro-2-methylpropyl)sulfamoyl]-8,9-dihydro-7H-cyclopenta[h]isoquinolin-7-yl]pyridine-3-carboxamide.

The following examples illustrate how the compounds covered by formula (I) may be synthesized.

They are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLES

| Abbreviations | |
|---|---|
| AcOH | Acetic Acid |
| DCM | Dichloromethane |
| MTBE | tert-Butylmethyl ether |
| $Et_2O$ | Diethyl ether |
| THF | Tetrahydrofuran |
| EtOAc | Ethyl acetate |
| MeCN | Acetonitrile |
| MeOH | Methanol |
| h | Hour |
| r.t. | Room temperature |
| M | Mass |
| Brine | Saturated sodium chloride solution |
| HPLC | High performance liquid chromatography |
| LCMS | Liquid Chromatography Mass Spectrometry |
| MS | Mass Spectrometry |
| ES+ | Electrospray positive ionisation |
| DIPEA | N,N-di-iso-propylethylamine |
| RT | Retention time |

-continued

| Abbreviations | |
|---|---|
| DMF | N,N'-dimethylformamide |
| TFA | Trifluoroacetic acid |
| DMSO | Dimethyl sulfoxide |
| TBTU | O-(Benzotriazol-1-yl)-N,N,N',N'-tetramethyl-uronium tetrafluoroborate |
| EtOH | Ethanol |
| sat. | saturated |
| aq. | aqueous |
| tBuXPhos Pd G3 | [(2-Di-tert-butylphosphino-2',4',6'-triisopropyl-1,1'-biphenyl)-2-(2'-amino-1,1' biphenyl)] palladium(II) methanesulfonate |
| TEA | Triethylamine |
| DMA | N,N-dimethylacetamide |
| TBME | tert-Butylmethyl ether (also abbreviated to MTBE) |
| o/n | overnight |
| IPA | Isopropyl alcohol |
| conc. | Concentrated |
| SCX | Biotage ® ISOLUTE ® SCX-2 Propylsulfonic acid functionalized silica |

LCMS Methods

Method 1

| | |
|---|---|
| X-Bridge C18 waters | 2.1 × 20 mm, 2.5 μm column |
| Column Temperature | 40° C. |
| Mobile Phase A: | 10 mM Ammonium formate in water + 0.1% formic acid |
| Mobile Phase B: | Acetonitrile + 5% water + 0.1% formic acid |
| Gradient program: | Flow rate 1 mL/minute |

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 2

| | |
|---|---|
| X-Bridge C18 Waters | 2.1 × 20 mm, 2.5 μM column |
| Column Temperature | 40° C. |
| Mobile Phase A: | 10 mM Ammonium formate in water + 0.1% formic acid |
| Mobile Phase B: | Acetonitrile + 5% water + 0.1% Formic acid |
| Gradient program: | Flow rate 1 mL/min |

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Method 3

| | |
|---|---|
| Waters UPLC ® BEH ™ C18 Part No. 186002352, | 2.1 × 100 mm, 1.7 μm |
| Column Temperature | 40° C. |
| Mobile Phase A: | 2 mM ammonia bicarbonate, buffered to pH 10 |
| Mobile Phase B: | Acetonitrile |
| Gradient program | Flow rate 0.6 mL/Min |

-continued

| Time | A % | B % |
|---|---|---|
| 0.00 | 95.00 | 5.00 |
| 5.30 | 0 | 100 |
| 5.80 | 0 | 100 |
| 5.82 | 95.00 | 5.00 |
| 7.00 | 95.00 | 5.00 |

Method 4

| | |
|---|---|
| Mobile Phase A: | 0.1% Formic Acid in water |
| Mobile Phase B: | 0.1% Formic Acid in Acetonitrile |
| Phenomenex, Kinetex-XB C18, 2.1 mm × 100 mm, 1.7 μm column | |
| Flow rate: | 0.6 mL/min |
| Column temperature: | 40° C. |
| Injection volume: | 1 μL |

| Gradient: | Time (minutes): | % A | % B |
|---|---|---|---|
| | 0.00 | 95 | 5 |
| | 5.30 | 0 | 100 |
| | 5.80 | 0 | 100 |
| | 5.82 | 95 | 5 |
| | 7.00 | 95 | 5 |
| UV 215 nM, PDA spectrum 200-400 nm, step: 1 nm | | | |
| MSD Scan Positive 150-850 | | | |

Method 5

| | |
|---|---|
| Mobile Phase A: | 2 mM Ammonium bicarbonate pH10 |
| Mobile Phase B: | Acetonitrile |
| Phenomenex Gemini-NX C18 2.0 mm × 50 mm, 3 μm column | |
| Flow rate: | 0.6 mL/min |
| Column temperature: | 40° C. |
| Injection volume: | 3 μL |

| Gradient: | Time (minutes): | % A | % B |
|---|---|---|---|
| | 0.00 | 95 | 5 |
| | 5.50 | 0 | 100 |
| | 5.90 | 0 | 100 |
| | 5.92 | 95 | 5 |
| UV 215 nM, PDA spectrum 210-420 nm, step: 1 nm | | | |
| MSD Scan Positive 150-850 | | | |

Method 6

A QDA Waters simple quadrupole mass spectrometer is used for LCMS analysis.

This spectrometer is equipped with an ESI source and an UPLC Acquity Classic with diode array detector (210 to 400 nm).

Data are acquired in a full MS scan from m/z 50 to 1000 in positive mode with a basic elution.

The reverse phase separation is carried out at 45° C. on a Waters Acquity UPLC BEH C18 1.7 μm (2.1×50 mm) column for basic elution.

Gradient elution is performed with:

| | |
|---|---|
| Mobile Phase A: | $H_2O$/acetonitrile/ammonium formate (95/5/63 mg/L) + 50 µL $NH_4OH$ |
| Mobile Phase B: | Acetonitrile/$H_2O$/ammonium formate (95/5/63 mg/L) + 50 µL $NH_4OH$ |
| Gradient program: | |
| HPLC flow rate: | 0.4 mL/minute to 0.5 mL/minute |
| Injection volume: | 1 µL |

| Full flow in MS. | Time (minute) | A (%) | B (%) | Flow (mL/minute) |
|---|---|---|---|---|
| | 0 | 99 | 1 | 0.4 |
| | 0.3 | 99 | 1 | 0.4 |
| | 3.2 | 0 | 100 | 0.4 |
| | 3.25 | 0 | 100 | 0.5 |
| | 4 | 0 | 100 | 0.5 |
| | 4.1 | 99 | 1 | 0.4 |
| | 4.8 | 90 | 1 | 0.4 |

Method 7

| | |
|---|---|
| Stationary phase: | X-Bridge C18 Waters 2.1 × 20 mm, 2.5 µM column |
| Mobile Phase A: | 10 mM Ammonium formate in water + 0.1% Ammonia solution |
| Mobile Phase B: | Acetonitrile + 5% water + 0.1% Ammonia Solution |
| Flow rate: | 1 mL/min |

| Gradient program: | Time | A % | B % |
|---|---|---|---|
| | 0.00 | 95.00 | 5.00 |
| | 1.50 | 5.00 | 95.00 |
| | 2.25 | 5.00 | 95.00 |
| | 2.50 | 95.00 | 5.00 |

Method 8

| | |
|---|---|
| Stationary phase: | X-Bridge C18 Waters 2.1 × 20 mm, 2.5 µM column |
| Mobile Phase A: | 10 mM Ammonium formate in water + 0.1% Ammonia solution |
| Mobile Phase B: | Acetonitrile + 5% water + 0.1% Ammonia Solution |
| Flow rate: | 1 mL/min |

| Gradient program: | Time | A % | B % |
|---|---|---|---|
| | 0.00 | 95.00 | 5.00 |
| | 1.50 | 5.00 | 95.00 |
| | 2.25 | 5.00 | 95.00 |
| | 2.50 | 95.00 | 5.00 |

Method 9

| | |
|---|---|
| Stationary phase: | X-Bridge C18 Waters 2.1 × 20 mm, 2.5 µM column |
| Mobile Phase A: | 10 mM Ammonium formate in water + 0.1% Formic acid |
| Mobile Phase B: | Acetonitrile + 5% water + 0.1% Formic acid |
| Flow rate: | Pump 1: 1 mL/min, Pump 2: 0.5 mL/min |

| Gradient | Pump 1: | | | Pump 2: | | |
|---|---|---|---|---|---|---|
| program: | Time | A % | B % | Time | A % | B % |
| | 0.00 | 95.10 | 4.90 | 0.10 | 5.00 | 95.00 |
| | 4.00 | 5.00 | 95.00 | 1.00 | 5.00 | 95.00 |
| | 5.00 | 5.00 | 95.00 | 1.10 | 95.00 | 5.00 |
| | 5.10 | 95.10 | 4.90 | | | |

Method 10

| Stationary phase: | X-Bridge C18 Waters 2.1 × 20 mm, 2.5 μM column | |
|---|---|---|
| Mobile Phase A: | 10 mM Ammonium formate in water + 0.1% Ammonia solution | |
| Mobile Phase B: | Acetonitrile + 5% water + 0.1% Ammonia Solution | |
| Flow rate: | 1 mL/min | |

| Gradient program: | Time | A % | B % |
|---|---|---|---|
| | 0.00 | 95.00 | 5.00 |
| | 1.50 | 5.00 | 95.00 |
| | 2.25 | 5.00 | 95.00 |
| | 2.50 | 95.00 | 5.00 |

Method 11

| Stationary phase: | Waters Acquity UPLC BEH C18 2.1 × 50 mm, 1.7 μM column |
|---|---|
| Mobile Phase A: | 10 mM Ammonium formate in water + 0.1% Ammonia solution |
| Mobile Phase B: | Acetonitrile + 5% water + 0.1% Ammonia Solution |
| Flow rate: | 1.5 mL/min |

| Gradient program: | Time | A % | B % |
|---|---|---|---|
| | 0.00 | 95.00 | 5.00 |
| | 0.10 | 95.00 | 5.00 |
| | 3.50 | 5.00 | 95.00 |
| | 4.00 | 5.00 | 95.00 |
| | 4.05 | 95.00 | 5.00 |

Method 12

| Stationary phase: | X-Bridge C18 Waters 2.1 × 20 mm, 2.5 μM column |
|---|---|
| Mobile Phase A: | 10 mM Ammonium formate in water + 0.1% ammonia solution |
| Mobile Phase B: | Acetonitrile + 5% water + 0.1% Ammonia Solution |
| Flow rate: | 1 mL/min |

| Gradient program: | Time | A % | B % |
|---|---|---|---|
| | 0.00 | 95.00 | 5.00 |
| | 4.00 | 5.00 | 95.00 |
| | 5.00 | 5.00 | 95.00 |
| | 5.10 | 95.00 | 5.00 |

Method 13

| Stationary phase: | X-Bridge C18 Waters 2.1 × 20 mm, 2.5 μM column |
|---|---|
| Mobile Phase A: | 10 mM Ammonium formate in water + 0.1% ammonia solution |
| Mobile Phase B: | Acetonitrile + 5% water + 0.1% Ammonia Solution |
| Flow rate: | 1 mL/min |

| Gradient program: | Time | A % | B % |
|---|---|---|---|
| | 0.00 | 95.00 | 5.00 |
| | 4.00 | 5.00 | 95.00 |
| | 5.00 | 5.00 | 95.00 |
| | 5.10 | 95.00 | 5.00 |

Method 14

| Stationary phase: | X-Bridge C18 Waters 2.1 × 20 mm, 2.5 μM column | | |
|---|---|---|---|
| Mobile Phase A: | 10 mM Ammonium formate in water + 0.1% Ammonia solution | | |
| Mobile Phase B: | Acetonitrile + 5% water + 0.1% Ammonia Solution | | |
| Flow rate: | 1 mL/min | | |
| Gradient program: | Time | A % | B % |
| | 0.00 | 95.00 | 5.00 |
| | 1.50 | 5.00 | 95.00 |
| | 2.25 | 5.00 | 95.00 |
| | 2.50 | 95.00 | 5.00 |

Method 15

| Stationary phase: | X-Bridge C18 Waters 2.1 × 20 mm, 2.5 μM column | | | | | |
|---|---|---|---|---|---|---|
| Mobile Phase A: | 10 mM Ammonium formate in water + 0.1% Ammonia solution | | | | | |
| Mobile Phase B: | Acetonitrile + 5% water + 0.1% Ammonia solution | | | | | |
| Flow rate: | Pump 1: 1 mL/min, Pump 2: 0.5 mL/min | | | | | |
| | Pump 1: | | | Pump 2: | | |
| Gradient program: | Time | A% | B% | Time | A% | B% |
| | 0.00 | 95.10 | 4.90 | 0.10 | 5.00 | 95.00 |
| | 4.00 | 5.00 | 95.00 | 1.00 | 5.00 | 95.00 |
| | 5.00 | 5.00 | 95.00 | 1.10 | 95.00 | 5.00 |
| | 5.10 | 95.10 | 4.90 | | | |

Method 16

| Stationary phase: | Waters Acquity UPLC BEH, C18, 2.1 × 50 μm, 1.7 μM | | |
|---|---|---|---|
| Mobile Phase A: | 10 mM Ammonium Formate in water + 0.1% Ammonia Solution | | |
| Mobile Phase B: | Acetonitrile + 5 % water + 0.1% Ammonia Solution | | |
| Flow rate: | 0.7 mL/min | | |
| Gradient program: | Time | A % | B % |
| | 95.00 | 95.00 | 95.00 |
| | 0.00 | 98.00 | 2.00 |
| | 4.00 | 5.00 | 95.00 |
| | 5.00 | 5.00 | 95.00 |
| | 5.10 | 98.00 | 2.00 |

Method 17

| Stationary phase: | X-Bridge C18 Waters 2.1 × 20 mm, 2.5 μM column | | |
|---|---|---|---|
| Mobile Phase A: | 10 mM Ammonium formate in water + 0.1% ammonia solution | | |
| Mobile Phase B: | Acetonitrile + 5% water + 0.1% Ammonia Solution | | |
| Flow rate: | 1 mL/min | | |
| Gradient program: | Time | A % | B % |
| | 0.00 | 95.00 | 5.00 |
| | 4.00 | 5.00 | 95.00 |
| | 5.00 | 5.00 | 95.00 |
| | 5.10 | 95.00 | 5.00 |

Method 18

A SYNAPT G2-SI Waters Q-TOF mass spectrometer equipped with an ESI source and a Waters Acquity H-class UPLC with diode array detector (210 to 400 nm.)

Data are acquired in a full MS scan from m/z 50 to 1200 in positive mode

The reverse phase separation is carried out at 45° C. on an Acquity UPLC HSS T3 C18 column (1.8 μm, 2.1×50 mm)

Gradient elution is done with

Solvent C: Water/Acetonitrile/Formic acid (95/5/750l/L)

Solvent D: Water/Acetonitrile/Formic acid (5/95/500l/L)

pH~3

Full flow in MS.

injection volume: 0.5 to 1 μl

| Time (min) | C (%) | D (%) | Flow |
| --- | --- | --- | --- |
| 0 | 98 | 2 | 0.8 |
| 0.3 | 98 | 2 | 0.8 |
| 3 | 5 | 95 | 0.8 |
| 4 | 5 | 95 | 0.8 |
| 4.1 | 98 | 2 | 0.8 |
| 5.1 | 98 | 2 | 0.8 |

General Procedures

General Procedure 1

To a stirred solution of the relevant amine (1 equivalent) in DCM (unless otherwise stated) were added DIPEA (2-4 equivalents) and isocyanate/isothiocyanate (2-4 equivalents). The reaction was heated at reflux (unless otherwise stated). After completion, the reaction mixture was concentrated in vacuo and purified by column chromatography.

General Procedure 2

To a stirred solution of the relevant amine (1 equivalent) in DCM (2 mL) at room temperature were added DIPEA (2-4 equivalents) and an acid chloride (2-4 equivalents). After completion, the reaction mixture was concentrated in vacuo and purified by column chromatography.

Intermediate 1

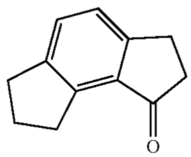 [SMILES: O=C1CCc2ccc3c(c21)CCC3]

3,6,7,8-tetrahydro-2H-as-indacen-1-one

3-Indan-5-ylpropanoic acid (100 g, 526 mol, commercially available from Angene, CAS number: 23291-98-7) in polyphosphoric acid (320 mL) was heated to 140° C. for 6 minutes then cooled to 10° C. and quenched by the addition of ice-water (500 mL). The resulting mixture was extracted with DCM (25 L followed by 15 L). The combined organic extracts were dried over $Na_2SO_4$, filtered and concentrated in vacuo. The residue was purified by column chromatography on $SiO_2$ to give the title compound as a brown solid (4.5 g, 5% yield). $\delta_H$ (400 MHz, CDCl3) 7.42 (m, 1H), 7.23 (m, 1H), 3.21 (m, 2H), 3.10 (m, 2H), 2.94 (m, 2H), 2.66 (m, 2H), 2.14 (m, 2H).

Intermediate 2

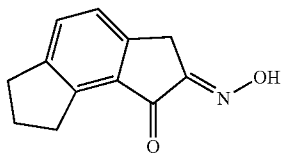 [SMILES: O=C1/C(=N/O)Cc2ccc3c(c21)CCC3]

(2E)-2-hydroxyimino-3,6,7,8-tetrahydro-as-indacen-1-one

A solution of intermediate 1 (85 g, 493 mmol) in MTBE (1.27 L) was treated with HCl (12 M in EtOH, 20.6 mL), cooled to 0° C. and treated with a solution of isopentyl nitrite (100 mL, 740 mol) in ethanol (600 mL) [added dropwise over 5 minutes]. The resulting mixture was stirred at 0° C. for 0.4 h then the solid was collected by filtration and washed with MTBE and dried, to yield the title compound as a brown solid (80 g, 81% yield). MS m/z=202 $[M+H]^+$. $\delta_H$ (400 MHz, DMSO-d6) 7.55 (d, 1H), 7.34 (d, 1H), 3.70 (s, 2H), 3.12 (t, 2H), 2.86 (t, 2H), 2.04-2.11 (m, 2H).

Intermediate 3

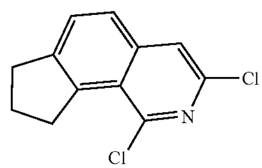 [SMILES: Clc1cc2ccc3c(c2c(Cl)n1)CCC3]

1,3-dichloro-8,9-dihydro-7H-cyclopenta[h]isoquinoline

A solution of intermediate 2 (83 g, 412.5 mol) in $POCl_3$ (1.25 L) was cooled to 0° C. and treated with $PCl_5$ (94.5 g, 454 mol). The resulting mixture was treated with HCl (gas) until the reaction was saturated and stirred at 65° C. for 1 h. After this time the mixture was treated with further $PCl_5$ (34.4 g, 165 mmol) and stirred for a further 15 h. The mixture was concentrated in vacuo and treated with water, the resulting solid was collected by filtration and dried to give the title compound (80 g, 81% yield). MS m/z=238 $[M+H]^+$. $\delta_H$ (400 MHz, $CDCl_3$) 7.64-7.56 (m, 3H), 3.75 (m, 2H), 3.09 (m, 2H), 2.19-2.26 (m, 2H).

Intermediate 4

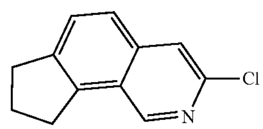 [SMILES: Clc1cc2ccc3c(c2cn1)CCC3]

3-chloro-8,9-dihydro-7H-cyclopenta[h]isoquinoline

A solution of intermediate 3 (80 g, 336 mol) in EtOAc (666 mL) was treated with phosphorous (27.4 g, 806.4 mmol) and HI (155 mL, 57% wt aqueous solution, 1.18 mol) and stirred at 120° C. for 4 h. The resulting mixture was filtered whilst hot and concentrated in vacuo. The residue was dissolved in water, basified by the addition of ammonia solution and the resulting solid collected by filtration. The solid was dissolved in DCM, washed with brine, dried over $Na_2SO_4$ and concentrated and purified by column chromatography on $SiO_2$ to give the title compound as a white solid (38.5 g, 56% yield). MS m/z=204 $[M+H]^+$. $\delta_H$ (400 MHz, $CDCl_3$) 9.04 (s, 1H), 7.70 (s, 1H), 7.56-7.63 (m, 2H), 3.34 (m, 2H), 3.11 (m, 2H), 2.34-2.27 (m, 2H).

Intermediate 5

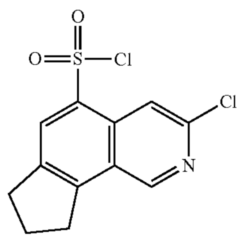 [SMILES: O=S(=O)(Cl)c1cc2c(c3cnc(Cl)cc13)CCC2]

3-chloro-8,9-dihydro-7H-cyclopenta[h]isoquinoline-5-sulfonyl chloride

Intermediate 4 (10 g, 49 mmol) was charged in a sealed 250 mL round bottom pressure flask and chlorosulfonic acid (35 mL, 520 mmol) was added (evolution of hydrogen chloride gas was observed upon addition). The resulting dark red/brown solution was purged under a flow of nitrogen for 5 minutes. The flask was sealed and heated at 80° C. for 3 hours. The reaction mixture was diluted with dichloromethane (100 mL) and then added carefully to stirred ice-water (500 mL) over 45 minutes. The two phases were separated, and the aqueous layer further extracted into dichloromethane (200 mL×2), combined organic extracts were washed with brine (200 mL), dried over sodium sulfate and evaporated down to give the title compound (14.6 g, 98% Yield). $^1$H NMR (300 MHz, Chloroform-d) $\delta_H$ 9.20 (d, J=0.9 Hz, 1H), 8.57 (d, J=0.8 Hz, 1H), 8.46 (s, 1H), 3.48 (tt, J=8.0, 1.2 Hz, 2H), 3.29-3.14 (m, 2H), 2.50-2.32 (m, 2H). LCMS $[M+H]^+$ 302/304, RT 1.33 (Method 8)

Intermediate 6

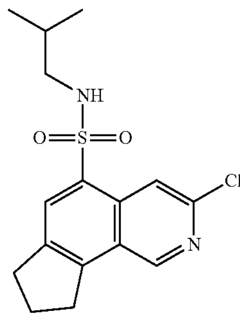 [SMILES: CC(C)CNS(=O)(=O)c1cc2c(c3cnc(Cl)cc13)CCC2]

3-chloro-N-isobutyl-8,9-dihydro-7H-cyclopenta[h]isoquinoline-5-sulfonamide

To a stirred solution of intermediate 5 (14.6 g, 48 mmol) in anhydrous DCM (125 mL) under nitrogen was added isobutylamine (12 mL, 120 mmol) dropwise (evolution of gas was observed). The reaction mixture was stirred at room temperature for 3 days. The reaction mixture was washed with water (125 mL). The aqueous layer separated and further extracted into dichloromethane (125 mL×2), combined organic extracts washed with brine (150 mL), dried over sodium sulfate and evaporated to dryness. The crude was purified by chromatography (gradient of 0% to 100% ethyl acetate in iso-hexane) to give the title compound (10.7 g, 65% Yield). $^1$H NMR (300 MHz, Chloroform-d) $\delta_H$ 9.14 (d, J=0.9 Hz, 1H), 8.48 (d, J=0.9 Hz, 1H), 8.36 (s, 1H), 4.67 (t, J=6.4 Hz, 1H), 3.50-3.35 (m, 2H), 3.18 (t, J=7.4 Hz, 2H), 2.78-2.65 (m, 2H), 2.45-2.28 (m, 2H), 1.69 (dq, J=13.4, 6.7 Hz, 1H), 0.81 (d, J=6.7 Hz, 6H). LCMS $[M+H]^+$ 339/341, RT 1.26 (Method 8).

Intermediates 7 & 8

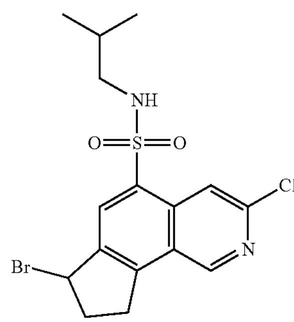

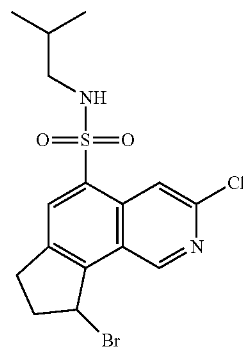

7-bromo-3-chloro-N-isobutyl-8,9-dihydro-7H-cyclopenta[h]isoquinoline-5-sulfonamide (7) 9-bromo-3-chloro-N-isobutyl-8,9-dihydro-7H-cyclopenta[h]isoquinoline-5-sulfonamide (8)

To a stirred solution of intermediate 6 (4.77 g, 14.1 mmol) in EtOAc (250 mL), 2,2'-azobis(2-methylpropionitrile) (240 mg, 1.4 mmol) and N-bromosuccinimide (3.3 g, 18 mmol) were added. The reaction mixture was stirred at 90° C. in the dark for 2.5 hours. The reaction mixture was evaporated to give a crude 1:1 mixture of the title compounds (9.24 g) which was used in the next step without further purification.

Intermediate 9 & 10

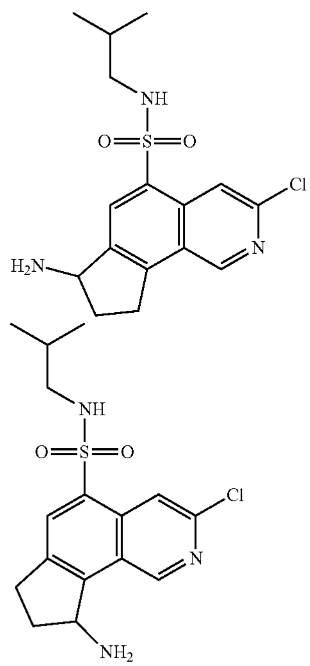

7-amino-3-chloro-N-isobutyl-8,9-dihydro-7H-cyclopenta[h]isoquinoline-5-sulfonamide (9)

9-amino-3-chloro-N-isobutyl-8,9-dihydro-7H-cyclopenta[h]isoquinoline-5-sulfonamide (10)

Two batches of a crude 1:1 mixture of intermediates 7 & 8 (2.31 g, 6 mmol) were dissolved in 0.4 M ammonia in THF (400 mL, 200 mmol) in round bottom pressure flasks. The sealed reaction mixtures were heated at 70° C. for 16 hours. The two reaction mixtures were cooled and evaporated down.

The resulting residues were resubmitted to the reaction conditions above using half the amount of ammonia in THF for 21 hours. The reaction mixtures were cooled, combined and evaporated down to give a ~1:1 ratio of the title compounds (4.7 g) which was used in the next step without further purification.

Intermediate 11 & 12

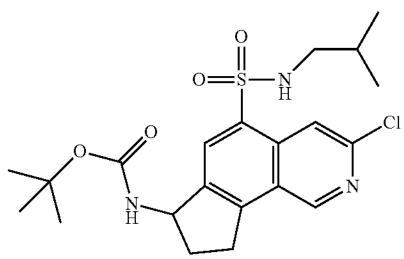

-continued

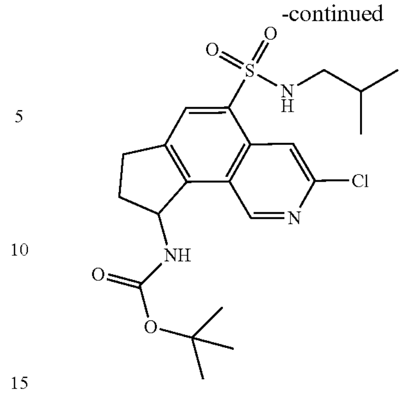

tert-butyl N-[3-chloro-5-(isobutylsulfamoyl)-8,9-dihydro-7H-cyclopenta[h]isoquinolin-7-yl]carbamate (11)

tert-butyl N-[3-chloro-5-(isobutylsulfamoyl)-8,9-dihydro-7H-cyclopenta[h]isoquinolin-9-yl]carbamate (12)

To a stirred ~1:1 mixture of intermediates 9 & 10 (2.88 g, 8.14 mmol) in dichloromethane (60 mL) was added di-tert-butyl dicarbonate (1.86 g, 8.52 mmol) followed by triethylamine (2.26 mL, 16.3 mmol). The reaction mixture was stirred at room temperature for 2 hours. The reaction mixture was evaporated to dryness and the crude purified by column chromatography (gradient of 0% to 100% ethyl acetate in iso-hexane) to give the title compounds.

Intermediate 11 (877 mg, 39% Yield)

LCMS $[M+H]^+$ 454/456, RT 1.28 (Method 8). $^1$H NMR (300 MHz, Chloroform-d) $\delta_H$ 9.15 (d, J=0.8 Hz, 1H), 8.51 (d, J=0.9 Hz, 1H), 8.42 (s, 1H), 5.40 (m, 1H), 4.88 (m, 1H), 4.72 (t, J=6.4 Hz, 1H), 3.54 (ddd, J=17.1, 9.1, 3.3 Hz, 1H), 3.35-3.17 (m, 1H), 2.95-2.63 (m, 3H), 2.17-1.98 (m, 1H), 1.77-1.66 (m, 1H), 1.51 (s, 9H), 0.83 (dd, J=6.7, 3.8 Hz, 6H).

Intermediate 12 (1.00 g, 46% Yield)

LCMS $[M+H]^+$ 454/456, RT 1.31 (Method 8). $^1$H NMR (300 MHz, Chloroform-d) $\delta_H$ 9.40 (d, J=0.8 Hz, 1H), 8.48 (d, J=0.8 Hz, 1H), 8.33 (s, 1H), 5.86 (s, 1H), 4.94 (m, J=9.5 Hz, 1H), 4.77 (t, J=6.4 Hz, 1H), 3.27 (dt, J=15.8, 7.6 Hz, 1H), 3.07 (ddd, J=16.8, 9.0, 4.6 Hz, 1H), 2.85-2.65 (m, 3H), 2.20 (m, 1H), 1.76-1.67 (m, 1H), 1.46 (s, 9H), 0.83 (dd, J=6.7, 1.8 Hz, 6H).

Intermediate 13

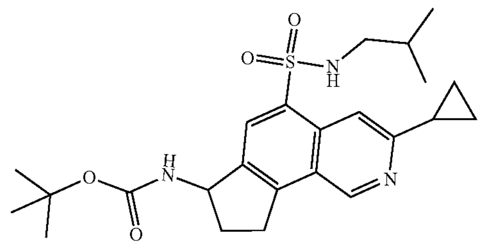 [SMILES: CC(C)CNS(=O)(=O)c1cc2c(c3cnc(C4CC4)cc13)CCC2NC(=O)OC(C)(C)C]

tert-butyl N-[3-cyclopropyl-5-(isobutylsulfamoyl)-8,9-dihydro-7H-cyclopenta[h]isoquinolin-7-yl]carbamate A mixture of intermediate 11 (910 mg, 2.0 mmol), cyclopropylboronic acid (540 mg, 6.0 mmol) and cesium carbonate (1.6 g, 4.9 mmol) in 1,4-dioxane (20 mL) was charged in a round bottom pressure flask under an atmosphere of nitrogen. Chloro(n2-P,C-tris(2,4-di-tert-butylphenyl)phosphite)(tricyclohexylphosphine)palladium(II) (210 mg, 0.20 mmol) was added and the sealed reaction mixture heated at 100° C. for 17 hours. The cooled reaction mixture was evaporated down. The resulting residue was partitioned between dichloromethane (50 mL) and water (25 mL). The aqueous layer was separated and further extracted into dichloromethane (50 mL×2), combined organic extracts were washed with brine (50 mL), dried over sodium sulfate and evaporated to dryness. The crude was purified by chromatography (gradient of 0% to 100% ethyl acetate in iso-hexane) to give the title compound (694 mg, 75% Yield). $^1$H NMR (300 MHz, Chloroform-d) $\delta_H$ 9.21 (d, J=0.9 Hz, 1H), 8.34 (s, 1H), 8.26 (d, J=0.9 Hz, 1H), 5.39 (m, 1H), 4.85 (m, 1H), 4.66 (t, J=6.4 Hz, 1H), 3.49 (ddd, J=17.1, 9.1, 3.5 Hz, 1H), 3.23 (dt, J=16.8, 8.1 Hz, 1H), 2.93-2.62 (m, 3H), 2.24 (ddd, J=13.2, 8.1, 4.8 Hz, 1H), 2.12-1.93 (m, 1H), 1.72 (m, 1H), 1.51 (s, 9H), 1.18-1.01 (m, 4H), 0.84 (dd, J=6.7, 4.4 Hz, 6H). LCMS [M+H]$^+$ 460, RT 1.38 (Method 8).

Intermediate 14

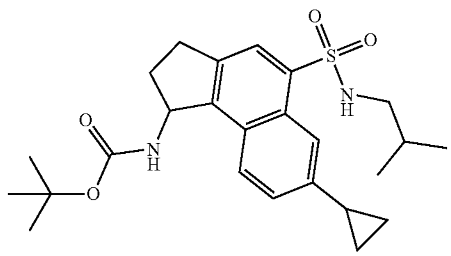 [SMILES: CC(C)CNS(=O)(=O)c1cc2c(c3ccc(C4CC4)cc13)C(NC(=O)OC(C)(C)C)CC2]

tert-butyl N-[7-cyclopropyl-5-(isobutylsulfamoyl)-2,3-dihydro-1H-cyclopenta[a]naphthalen-1-yl]carbamate A mixture of intermediate 12 (500 mg, 1.10 mmol), cyclopropylboronic acid (299 mg, 3.304 mmol) and cesium carbonate (906 mg, 2.753 mmol) in anhydrous 1,4-dioxane (5 mL) was degassed and filled with nitrogen. Chloro(n2-P,C-tris(2,4-di-tert-butylphenyl)phosphite)(tricyclohexylphosphine)palladium(II) (117.6 mg, 0.11 mmol) was added and the reaction mixture heated at 120° C. for 1.5 h in the microwave. The reaction mixture was concentrated under reduced pressure, then partitioned between DCM and water. Organic phase washed with brine, passed through a phase separator cartridge and evaporated. The crude was purified by column chromatography (eluting with 20-70% EtOAc/hexane) to give the title compound (332 mg, 66% Yield). LCMS [M+H-tBu]$^+$ 404.0, RT 2.73 (Method 15).

Intermediate 15

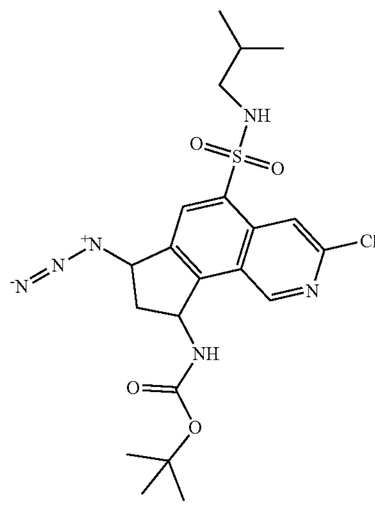

tert-butyl N-[7-azido-3-chloro-5-(isobutylsulfamoyl)-8,9-dihydro-7H-cyclopenta[h]isoquinolin-9-yl]carbamate To a solution of intermediate 12 (2550 mg, 5.62 mmol) in EtOAc (120 mL) was added 1-bromopyrrolidine-2,5-dione (1200 mg, 6.74 mmol) and 2-[({E})-(1-cyano-1-methyl-ethyl)azo]-2-methyl-propanenitrile (92 mg, 0.562 mmol). The mixture was heated in the dark at 90° C. for 30 minutes. The reaction was cooled, and the solvent was removed to give a brown solid. The brown solid was dissolved in DMF (15 mL), cooled to 0° C. and sodium azide (657 mg, 10.1 mmol) was added. The reaction was stirred for 10 minutes. EtOAc (50 mL) was added to the reaction followed by water (30 mL). The organic layer was separated and washed further with water (2×20 mL) and brine (10 mL). The organic layer was dried ($MgSO_4$) and the solvent was removed to give a brown solid. The solid was purified by flash column chromatography eluting with 0 to 35% of ethyl acetate in heptane gradient to afford the title compound as a brown solid (2.2 g, 53% pure, 42% yield). LCMS [M+H]$^+$ 495, RT 3.37 minutes (Method 1). The other major peak in the LCMS was unreacted intermediate 11.

Intermediate 16

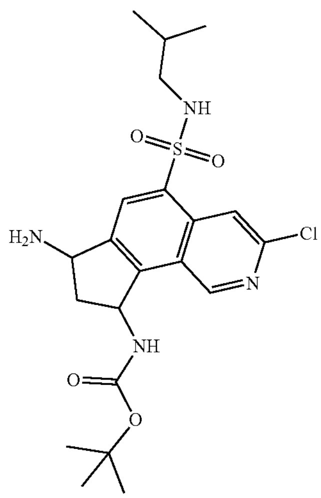 [SMILES: CC(C)CNS(=O)(=O)c1cc2c(c3cnc(Cl)cc13)C(NC(=O)OC(C)(C)C)CC2N]

tert-butyl N-[7-amino-3-chloro-5-(isobutylsulfamoyl)-8,9-dihydro-7H-cyclopenta[h]isoquinolin-9-yl]carbamate To a solution of intermediate 15 (19000 mg, 16.51 mmol, 43% pure) in ethyl acetate (100 mL) was added EtOH (50 mL) and 10% palladium on carbon (3328 mg, 3.12 mmol). The reaction evacuated and then placed under a hydrogen atmosphere and stirred vigorously for 2 hours. The palladium residues were filtered off through a celite plug and the solvent removed. The resulting residue was purified by flash column chromatography eluting with 0 to 100% of ethyl acetate in heptane gradient followed by 0 to 10% 7 M $NH_3$ in MeOH in ethyl acetate to afford the titled compound as a brown solid (5.98 g, 77% yield); LCMS $[M+H]^+$ 469, RT 2.49 minutes (Method 1) and recovered intermediate 12 (10 g, 60% pure).

Intermediate 17

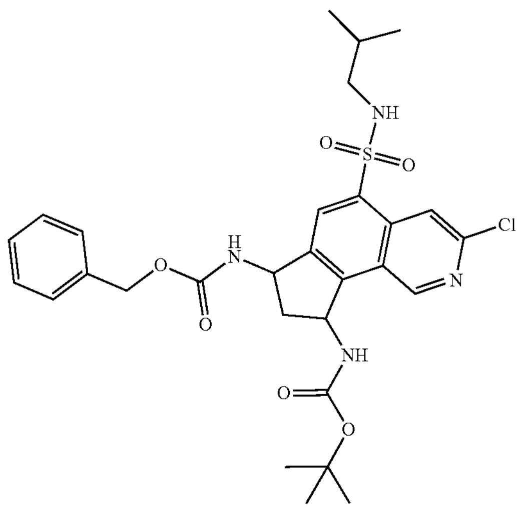 [SMILES: CC(C)CNS(=O)(=O)c1cc2c(c3cnc(Cl)cc13)C(NC(=O)OC(C)(C)C)CC2NC(=O)OCc1ccccc1]

tert-butyl N-[7-(benzyloxycarbonylamino)-3-chloro-5-(isobutylsulfamoyl)-8,9-dihydro-7H-cyclopenta[h]isoquinolin-9-yl]carbamate To a solution of intermediate 16 (5960 mg, 12.7 mmol) in DMF (40 mL) was added triethylamine (7.1 mL, 50.8 mmol) and benzyl (2,5-dioxopyrrolidin-1-yl) carbonate (4117 mg, 16.5 mmol). The solution was stirred for 30 minutes. The reaction was diluted with EtOAc (100 mL) and then washed with water (3×50 mL) and brine (30 mL). The organic layer was dried ($MgSO_4$) and the solvent was removed to give an oil. The oil was purified by flash column chromatography eluting with 0 to 40% of ethyl acetate in heptane gradient to afford the title compound as a fluffy brown solid (7.7 g, 94% yield); LCMS [M+H]+ 603, RT 3.39 and 3.47 minutes [cis and trans isomers](Method 1).

Intermediate 18

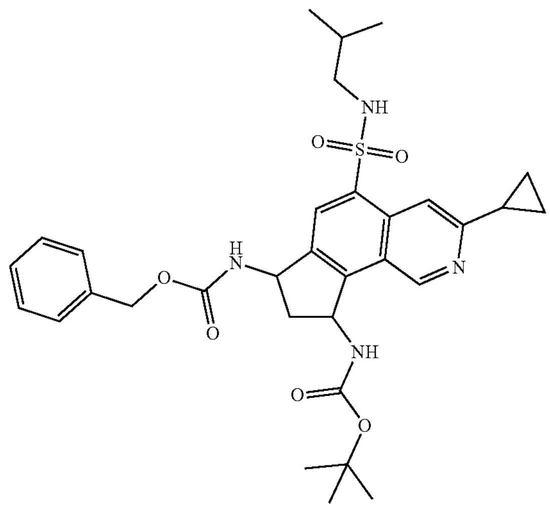 [SMILES: CC(C)CNS(=O)(=O)c1cc2c(c3cnc(C4CC4)cc13)C(NC(=O)OC(C)(C)C)CC2NC(=O)OCc1ccccc1]

tert-butyl N-[7-(benzyloxycarbonylamino)-3-cyclopropyl-5-(isobutylsulfamoyl)-8,9-dihydro-7H-cyclopenta[h]isoquinolin-9-yl]carbamate In a pressure tube, intermediate 17 (9.73 g, 16.1 mmol), tripotassium phosphate (12.2 g, 56.5 mmol), tricyclohexylphosphonium tetrafluoroborate (2.07 g, 5.65 mmol), diacetoxypalladium (1.10 g, 4.83 mmol) and cyclopropylboronic acid (6.24 g, 72.6 mmol) were suspended in a mixture of 1,4-dioxane (103 mL), toluene (51 mL) and water (8 mL). The system was evacuated thrice and backfilled with nitrogen and capped. The reaction was heated at 105° C. for 4 hours. The reaction was cooled and filtered through a plug of celite to remove the palladium residues. The celite was washed with EtOAc (20 mL) and water (10 mL). The filtrate was diluted with EtOAc (150 mL) and water (60 mL). The organic layer was separated and washed further with water (2×20 mL) and brine (20 mL). The organic layer was dried ($MgSO_4$) and the solvent was removed to give a brown oil. The oil was purified by flash column chromatography eluting with 0 to 40% of ethyl acetate in heptane gradient to afford the title compound as a brown solid (8.35 g, 85% yield); LCMS $[M+H]^+$ 609, RT 3.46 and 3.54 minutes [cis and trans isomers](Method 1).

Intermediates 19 & 20

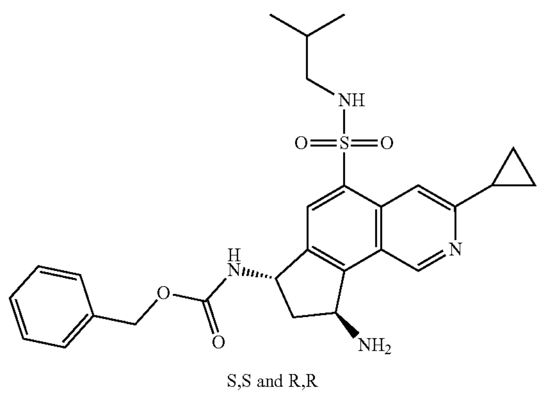

S,S and R,R

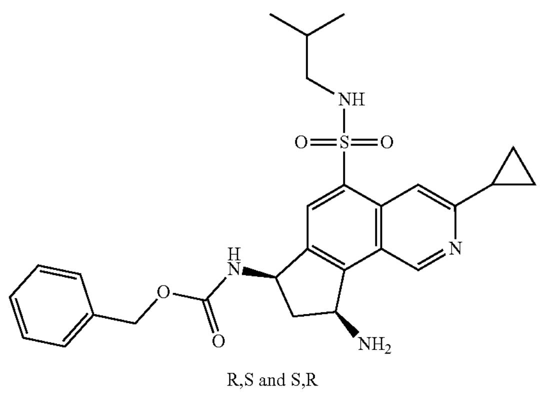

R,S and S,R benzyl N-[trans-(7SR,9SR)-9-amino-3-cyclopropyl-5-(isobutylsulfamoyl)-8,9-dihydro-7H-cyclopenta[h]isoquinolin-7-yl]carbamate (19) benzyl N-[cis-(7RS,9SR)-9-amino-3-cyclopropyl-5-(isobutylsulfamoyl)-8,9-dihydro-7H-cyclopenta[h]isoquinolin-7-yl]carbamate (20)

To a solution of intermediate 18 (850 mg, 1.40 mmol) in DCM (5 mL) was added trifluoroacetic acid (5 ml). The solution was stirred at room temperature for 30 minutes. The solvent was removed, azeotroping excess TFA with 1:1 DCM/heptane to give a brown oil. The oil was purified by SCX cartridge eluting with 0 to 100% of 7 M $NH_3$ in methanol gradient to afford the racemic amine as an orange gum. The gum was further purified by flash column chromatography eluting with 0 to 5% of 7 M $NH_3$ in MeOH in DCM gradient to give the title compounds as mixtures of enantiomers:

Trans product (intermediate 19) as a white solid (250 mg, 35% yield); $\delta_H$ (500 MHz, Chloroform-d) 9.48 (s, 1H), 8.32 (s, 1H), 8.27 (s, 1H), 7.46-7.30 (m, 5H), 5.67 (q, J=7.7 Hz, 1H), 5.22-5.08 (m, 3H), 5.02 (d, J=8.8 Hz, 1H), 4.69 (t, J=6.3 Hz, 1H), 2.84-2.73 (m, 1H), 2.73-2.54 (m, 2H), 2.31 (dt, J=13.6, 7.4 Hz, 1H), 2.22 (td, J=8.1, 4.1 Hz, 1H), 1.70 (dp, J=13.6, 6.7 Hz, 1H), 1.16 (tt, J=4.6, 2.4 Hz, 2H), 1.12-1.03 (m, 2H), 0.84 (t, J=6.8 Hz, 6H). LCMS $[M+H]^+$ 509, RT 2.55 minutes (Method 1).

Cis product (intermediate 20) as a white solid (305 mg, 42% yield); $\delta_H$ (500 MHz, Chloroform-d) 9.71 (s, 1H), 8.35 (s, 1H), 8.28 (s, 1H), 7.44-7.28 (m, 5H), 5.52 (d, J=8.4 Hz, 1H), 5.28-5.09 (m, 3H), 5.01-4.87 (m, 1H), 4.72 (t, J=6.2 Hz, 1H), 3.08-2.93 (m, 1H), 2.83-2.64 (m, 2H), 2.22 (ddd, J=13.0, 8.2, 4.8 Hz, 1H), 1.87 (dt, J=13.6, 4.3 Hz, 1H), 1.20-1.12 (m, 2H), 1.12-1.02 (m, 2H), 0.84 (t, J=6.5 Hz, 6H). LCMS [M+H]+ 509, RT 2.55 minutes (Method 1).

Intermediate 21

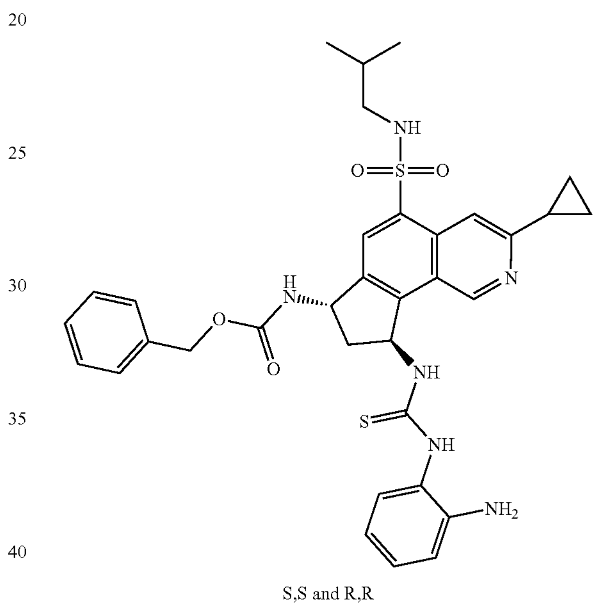

S,S and R,R benzyl N-[trans-(7SR,9SR)-9-[(2-aminophenyl)carbamothioylamino]-3-cyclopropyl-5-(isobutylsulfamoyl)-8,9-dihydro-7H-cyclopenta[h]isoquinolin-7-yl]carbamate To a mixture of sodium hydrogen carbonate (60 mg, 0.708 mmol) in water (0.5 mL) and DCM (1 mL) was added carbonothioyl dichloride (0.027 mL, 0.354 mmol) at 0° C. To this was added a solution of intermediate 19 (60 mg, 0.118 mmol) in DCM (1 mL). The mixture was stirred vigorously at 0° C. for 30 minutes. The organic layer was separated, and the aqueous layer extracted with DCM (10 mL). The combined organic layers were dried ($MgSO_4$) and the solvent was removed to give the intermediate isothiocyanate as a solid. The solid was dissolved in THF and benzene-1,2-diamine (22 mg, 0.200 mmol) was added. The solution was stirred for 18 hours. The solvent was removed to give a white solid. The solid was purified by flash column chromatography eluting with 0 to 100% of ethyl acetate in heptane gradient followed by a 0 to 10% methanol in EtOAc gradient to afford the title compound as a mixture of trans enantiomers (77 mg, 99% yield); LCMS $[M+H]^+$ 659, RT 2.03 minutes (Method 2).

Intermediate 22

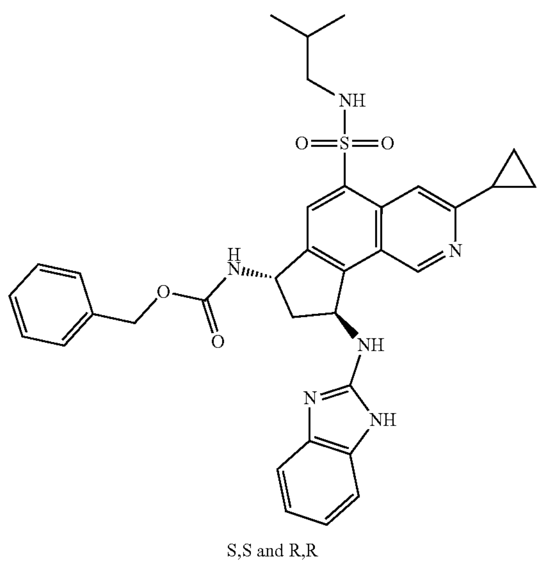 [SMILES: CC(C)CNS(=O)(=O)c1cc2c(c3cnc(C4CC4)cc13)[C@@H](Nc1nc3ccccc3[nH]1)C[C@@H]2NC(=O)OCc1ccccc1]

S,S and R,R benzyl N-[trans-(7SR,9SR)-9-(1H-benzimidazol-2-ylamino)-3-cyclopropyl-5-(isobutylsulfamoyl)-8,9-dihydro-7H-cyclopenta[h]isoquinolin-7-yl]carbamate To a suspension of intermediate 21 (77 mg, 0.117 mmol) in MeOH (2 mL) was added 2-iodoacetic acid (26 mg, 0.140 mmol). The reaction was heated at 70° C. for 90 minutes. Another portion of 2-iodoacetic acid (10 mg, 0.058 mmol) was added and the reaction was heated at 70° C. for a further 30 minutes. The solution was cooled, and the solvent removed to give a residue. The residue was partitioned between EtOAc (10 mL) and sat aq. $NaHCO_3$ solution (5 mL). The organic layer was separated, and the aqueous layer extracted further with EtOAc (2×10 mL). The combined organic layers were dried ($MgSO_4$) and the solvent was removed to give a solid. The solid was purified by flash column chromatography eluting with 0 to 5% of 7M $NH_3$/methanol in DCM gradient to afford the title compound as a mixture of trans enantiomers (50 mg, 68% yield); LCMS $[M+H]^+$ 625, RT 1.77 minutes (Method 2).

Intermediate 23

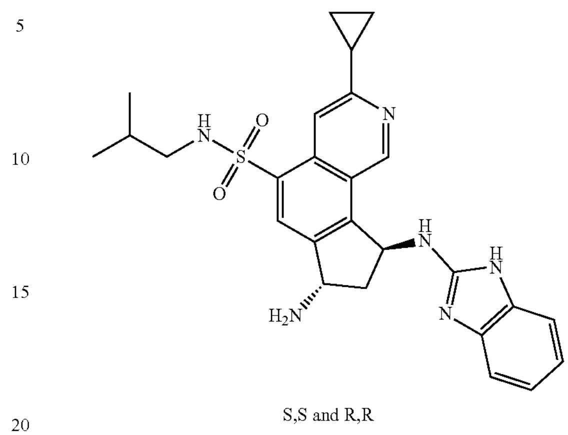

S,S and R,R

Trans-(7SR,9SR)-7-amino-9-(1H-benzimidazol-2-ylamino)-3-cyclopropyl-N-isobutyl-8,9-dihydro-7H-cyclopenta[h]isoquinoline-5-sulfonamide To a partial solution of intermediate 22 (381 mg, 0.610 mmol) in acetic acid (3 mL) was added hydrogen bromide in AcOH (45%, 3.5 mL, 27.4 mmol). The solids slowly went into solution over 30 minutes. The reaction was stirred for 1 hour. Another portion of HBr in AcOH (0.7 mL) was added and the reaction was stirred for a further 1 hour. The solvent was removed to give a brown residue. The residue was purified with an SCX cartridge eluting with 0 to 100% of 7 M $NH_3$ in methanol gradient to afford the title compound as a mixture of trans enantiomers (300 mg, 97% yield); LCMS $[M+H]^+$ 491, RT 1.48 minutes (Method 2).

Intermediate 24

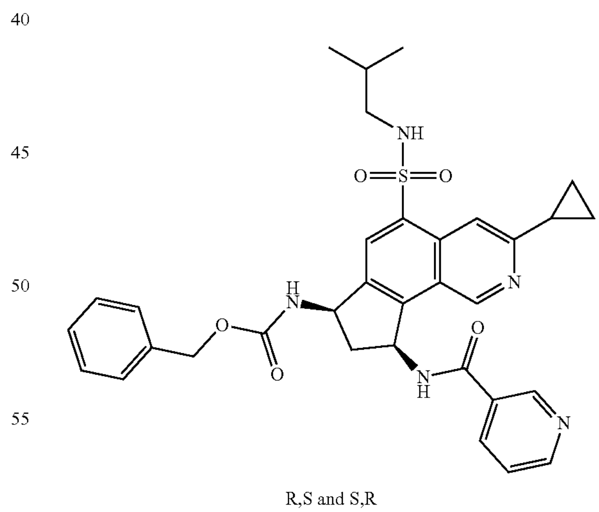

R,S and S,R benzyl N-[cis-(7RS,9SR)-3-cyclopropyl-5-(isobutylsulfamoyl)-9-(pyridine-3-carbonylamino)-8,9-dihydro-7H-cyclopenta[h]isoquinolin-7-yl]carbamate To a stirred solution of intermediate 20 (550 mg, 1.08 mmol) in THF (25 mL) at room temperature were added N,N-diisopropylethylamine (419 mg, 3.24 mmol) and nicotinoyl chloride hydrochloride (211 mg, 1.19 mmol). The reaction was monitored by LCMS until complete, then diluted with EtOAc (30 mL) and washed with sat. aq. $NaHCO_3$ solution and brine. Volatiles were removed in vacuo and the crude purified by column chromatography (eluting EtOAc in isohexane followed by MeOH in EtOAc) to give the title compound as a mixture of cis enantiomers (550 mg, 81% Yield). $^1H$ NMR (300 MHz, Methanol-d4) $\delta_H$ 9.40-9.33 (m, 1H), 9.00-8.92 (m, 1H), 8.73-8.62 (m, 1H), 8.43-8.38 (m, 1H), 8.33 (s, 1H), 8.27-8.19 (m, 1H), 7.55-7.48 (m, 1H), 7.42-7.26 (m, 5H), 6.27-6.13 (m, 1H), 5.31-5.07 (m, 3H), 3.38-3.33 (m, 1H), 2.65 (dd, J=6.9, 1.6 Hz, 2H), 2.27 (p, J=6.6 Hz, 1H), 2.15 (dt, J=14.3, 5.0 Hz, 1H), 1.73-1.51 (m, 1H), 1.10-1.04 (m, 4H), 0.78 (dd, J=6.7, 2.8 Hz, 6H). LCMS $[M+H]^+$ 614, RT 2.29 (Method 10).

Intermediate 25

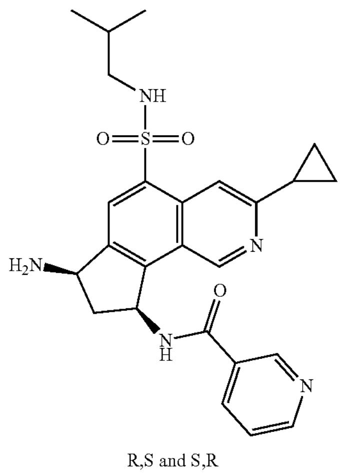 [SMILES: CC(C)CNS(=O)(=O)c1cc2c(c3cnc(C4CC4)cc13)[C@@H](NC(=O)c1cccnc1)C[C@H]2N]

R,S and S,R

N-[cis-(7RS,9SR)-7-amino-3-cyclopropyl-5-(isobutylsulfamoyl)-8,9-dihydro-7H-cyclopenta[h]isoquinolin-9-yl]pyridine-3-carboxamide Intermediate 24 (550 mg, 0.8783 mmol) was dissolved in EtOH (2 mL) and palladium on carbon (0.087 mmol) added. The solution was degassed and placed under an atmosphere of hydrogen. Additional portions of palladium on carbon were added until reaction had gone to completion. The reaction mixture was then filtered through celite, washing with EtOAc. The solvents were removed, and the crude purified by column chromatography eluting a gradient of 20% (3.5 N $NH_3$ MeOH in DCM) in DCM to give the title compound as a mixture of cis enantiomers (175 mg, 41% Yield). $^1H$ NMR (300 MHz, Methanol-d4) $\delta_H$ 8.53 (d, J=0.9 Hz, 1H), 8.18 (dd, J=2.3, 0.9 Hz, 1H), 7.87 (dd, J=4.9, 1.6 Hz, 1H), 7.71 (s, 1H), 7.60 (d, J=1.0 Hz, 1H), 7.45 (ddd, J=8.0, 2.3, 1.6 Hz, 1H), 6.72 (ddd, J=8.0, 4.9, 0.9 Hz, 1H), 5.37 (dd, J=8.7, 4.9 Hz, 1H), 3.73 (dd, J=8.0, 4.9 Hz, 1H), 2.49-2.39 (m, 2H), 1.86 (dd, J=6.9, 0.9 Hz, 2H), 1.52-1.40 (m, 1H), 0.89-0.76 (m, 1H), 0.29-0.18 (m, 4H), −0.01 (d, J=6.6 Hz, 6H). LCMS $[M+H]^+$ 480, RT 1.02 (Method 10).

Intermediate 26

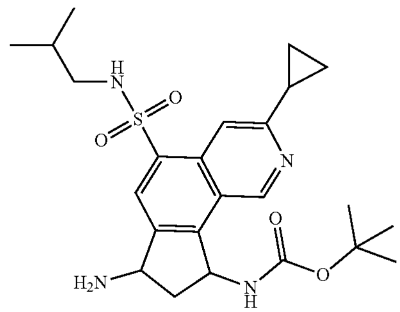 [SMILES: CC(C)CNS(=O)(=O)c1cc2c(c3cnc(C4CC4)cc13)C(NC(=O)OC(C)(C)C)CC2N]

tert-butyl N-[7-amino-3-cyclopropyl-5-(isobutylsulfamoyl)-8,9-dihydro-7H-cyclopenta[h]isoquinolin-9-yl]carbamate To a solution of intermediate 18 (300 mg, 0.493 mmol) in THF (3 mL) was added 10% palladium on carbon (600 mg, 0.564 mmol). The mixture was evacuated and placed under a hydrogen atmosphere for 4 hours. The palladium residues were removed through Celite washing the Celite with excess EtOAc (10 mL) and MeOH (10 mL). The solvent of the filtrate was removed to give an oil. The oil was purified by flash column chromatography eluting with 0 to 10% of 7 M $NH_3$/MeOH in DCM gradient to afford the title compound as a brown solid (160 mg, 68% yield); LCMS $[M+H]^+$ 475, RT 1.75 minutes (Method 2).

Intermediate 27 & 28

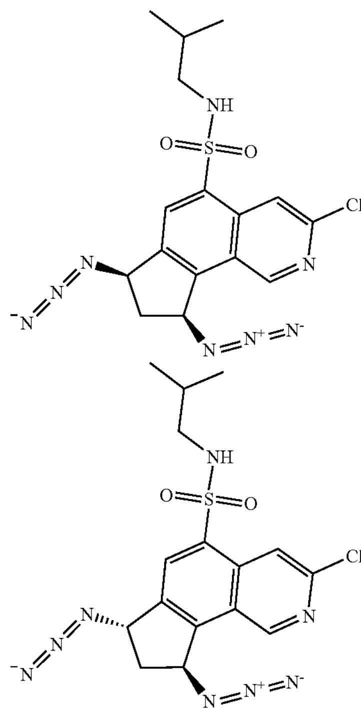

Cis-(7RS,9SR)-7,9-diazido-3-chloro-N-isobutyl-8,9-dihydro-7H-cyclopenta[h]isoquinoline-5-sulfonamide (27)

Trans-(7SR,9SR)-7,9-diazido-3-chloro-N-isobutyl-8,9-dihydro-7H-cyclopenta[h]isoquinoline-5-sulfonamide (28)

Intermediate 40 (12 g, 24.16 mmol) was dissolved in N,N-dimethylformamide (240 mL, 3.09 mol) and cooled in an ice bath prior to portion-wise addition of sodium azide (3.9 g, 60 mmol). The reaction mixture was stirred at this temperature for 1.5 h. The reaction was cooled in an ice bath prior to addition of water (250 mL) and TBME (250 mL). The resulting slurry was stirred vigorously then partitioned and the aqueous layer extracted with TBME (2×250 mL). The combined organic extracts were dried and concentrated in vacuo. Purification by column chromatography (0-40% gradient of EtOAc in isohexane) gave the title compounds as mixtures of enantiomers:

Intermediate 27 (838 mg, 9% Yield). $^1$H NMR (400 MHz, Chloroform-d) $\delta_H$ 9.39 (d, J=0.8 Hz, 1H), 8.52 (d, J=0.8 Hz, 1H), 8.38 (s, 1H), 5.42 (dd, J=7.9, 3.3 Hz, 1H), 4.88 (t, J=6.3 Hz, 1H), 3.44-3.32 (m, 1H), 3.15 (ddd, J=16.9, 8.9, 3.9 Hz, 1H), 2.85-2.68 (m, 3H), 2.55 (ddt, J=14.3, 8.5, 3.7 Hz, 1H), 1.73-1.67 (m, 1H), 0.82 (dd, J=6.7, 1.5 Hz, 6H). LCMS [M+H]$^+$ 421, RT 2.81 (Method 12).

Intermediate 28 (3.4 g, 33% Yield). $^1$H NMR (400 MHz, Chloroform-d) $\delta_H$ 9.49 (d, J=0.8 Hz, 1H), 8.57 (d, J=0.8 Hz, 1H), 8.46 (s, 1H), 5.34 (dd, J=7.8, 4.0 Hz, 1H), 5.06 (dd, J=7.7, 3.9 Hz, 1H), 4.85 (t, J=6.3 Hz, 1H), 3.25 (dt, J=14.8, 7.7 Hz, 1H), 2.80 (dq, J=17.1, 6.4 Hz, 3H), 2.51 (dt, J=14.8, 4.0 Hz, 1H), 1.79-1.64 (m, 1H), 0.82 (dd, J=6.7, 3.4 Hz, 6H). LCMS [M+H]$^+$ 421, RT 2.78 (Method 12).

Intermediates 29 & 29a

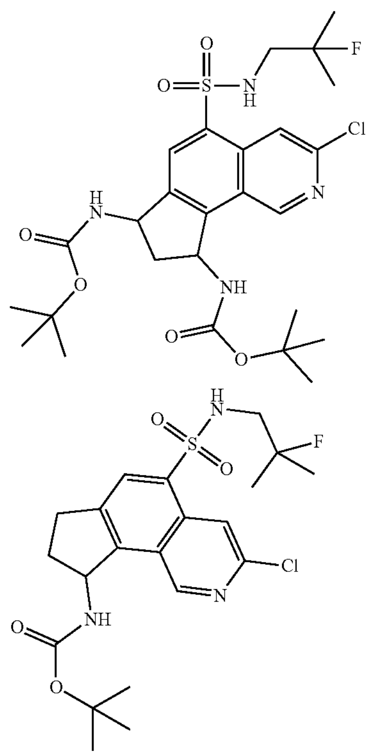

tert-butyl N-[7-(tert-butoxycarbonylamino)-3-chloro-5-[(2-fluoro-2-methyl-propyl)sulfamoyl]-8,9-dihydro-7H-cyclopenta[h]isoquinolin-9-yl]carbamate (29) tert-butyl N-[3-chloro-5-[(2-fluoro-2-methyl-propyl)sulfamoyl]-8,9-dihydro-7H-cyclopenta[h]isoquinolin-9-yl]carbamate (29a)

To a stirred solution of intermediate 53 (3.0 g, 8.40 mmol) in ethyl acetate (180 mL) under nitrogen was added 2,2'-azobis(2-methylpropionitrile) (140 mg, 0.840 mmol) and N-bromosuccinimide (2.0 g, 11 mmol). The reaction mixture was stirred at 90° C. in the dark for 1.5 hours. The reaction mixture was evaporated to give crude brominated products, as a pale brown residue (5.5 g). This mixture was dissolved in tetrahydrofuran (200 mL) and the mixture charged into a sealed 500 mL ace round bottom pressure flask. Ammonia gas was bubbled through the reaction mixture for 5 minutes. The sealed reaction mixture was heated at 70° C. for 2 days. The reaction mixture was cooled and then evaporated down to give crude aminated products, as a dark green residue (5.7 g). This mixture was dissolved in dichloromethane (100 mL) and di-tert-butyl dicarbonate (2.1 g, 9.5 mmol) was added followed by triethylamine (2.5 mL, 18 mmol). The reaction mixture was stirred at room temperature under nitrogen for 3 hours. The reaction mixture was evaporated to dryness and the crude product purified by chromatography eluting with a gradient of 0% to 40% ethyl acetate in iso-hexane to give approximately a 5.5:1 mixture of the title compounds 29a:29 respectively (1.2 g);

Intermediate 29 LCMS [M+H]$^+$ 587, RT 2.71 minutes (Method 13).

Intermediate 29a LCMS [M+H]+ 472, RT 2.55 minutes (Method 13).

Intermediate 30

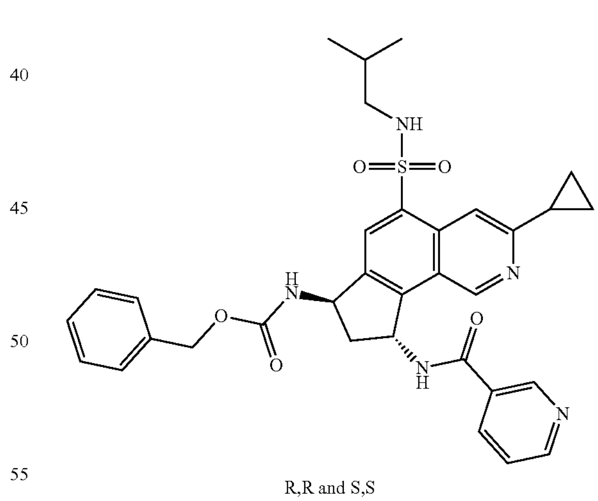

R,R and S,S benzyl N-[trans-(7RS,9RS)-3-cyclopropyl-5-(isobutylsulfamoyl)-9-(pyridine-3-carbonylamino)-8,9-dihydro-7H-cyclopenta[h]isoquinolin-7-yl]carbamate To a stirred solution of intermediate 19 (490 mg, 0.96 mmol) in THF (25 mL) at room temperature were added N,N-diisopropylethylamine (373 mg, 2.89 mmol) and nicotinoyl chloride hydrochloride (188 mg, 1.06 mmol). The reaction was monitored by LCMS until complete, then diluted with EtOAc (30 mL) and washed with sat. aq. $NaHCO_3$ solution and brine. Volatiles were removed in vacuo and the crude purified by column chromatography (eluting EtOAc in isohexane followed by MeOH in EtOAc) to give the title compound as a mixture of enantiomers (500 mg, 83% Yield). $^1H$ NMR (300 MHz, Methanol-d4) $\delta_H$ 9.34 (s, 1H), 8.97-8.92 (m, 1H), 8.65 (dd, J=5.0, 1.7 Hz, 1H), 8.46-8.39 (m, 1H), 8.33 (s, 1H), 8.27-8.20 (m, 1H), 7.57-7.46 (m, 1H), 7.46-7.24 (m, 5H), 6.43-6.32 (m, 1H), 5.70 (t, J=7.6 Hz, 1H), 5.27-5.09 (m, 2H), 2.74-2.46 (m, 3H), 2.35-2.21 (m, 1H), 1.72-1.57 (m, 1H), 1.14-1.00 (m, 4H), 0.83-0.68 (m, 6H). LCMS $[M+H]^+$ 614, RT 2.23 (Method 10).

Intermediate 31

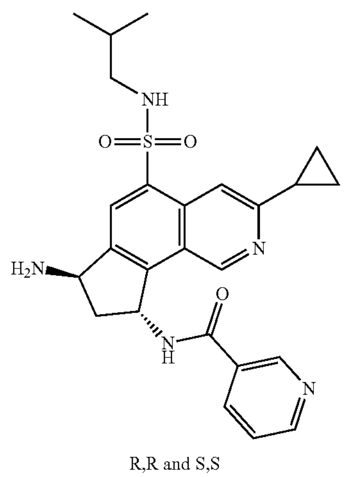 [SMILES: CC(C)CNS(=O)(=O)c1cc2c(c3cnc(C4CC4)cc13)[C@H](NC(=O)c1cccnc1)C[C@H]2N]

R,R and S,S

N-[trans-(7RS,9RS)-7-amino-3-cyclopropyl-5-(isobutylsulfamoyl)-8,9-dihydro-7H-cyclopenta[h]isoquinolin-9-yl]pyridine-3-carboxamide Intermediate 30 (500 mg, 0.81 mmol) was dissolved in EtOH (2 mL) and palladium on carbon (0.081 mmol) added. The solution was degassed and placed under an atmosphere of hydrogen. Additional portions of palladium on carbon were added until reaction had gone to completion. The reaction mixture was then filtered through Celite, washing with EtOAc. The solvents were removed, and the crude purified by column chromatography eluting a gradient of 20% (3.5 N $NH_3$ MeOH in DCM) in DCM to give the title compound as a mixture of enantiomers (157 mg, 40% Yield). $^1H$ NMR (300 MHz, Methanol-d4) $\delta_H$ 9.34 (d, J=0.9 Hz, 1H), 8.94 (dd, J=2.3, 0.9 Hz, 1H), 8.65 (dd, J=5.0, 1.7 Hz, 1H), 8.53 (s, 1H), 8.42 (d, J=1.0 Hz, 1H), 8.22 (ddd, J=8.0, 2.3, 1.7 Hz, 1H), 7.50 (ddd, J=8.0, 4.9, 0.9 Hz, 1H), 6.37 (dd, J=8.4, 2.5 Hz, 1H), 2.71-2.61 (m, 3H), 2.54-2.40 (m, 1H), 2.34-2.22 (m, 1H), 1.66 (dt, J=13.5, 6.8 Hz, 1H), 1.12-1.04 (m, 4H), 0.81 (dd, J=6.7, 1.1 Hz, 6H). LCMS $[M+H]^+$ 480, RT 0.99 (Method 10).

Intermediate 32

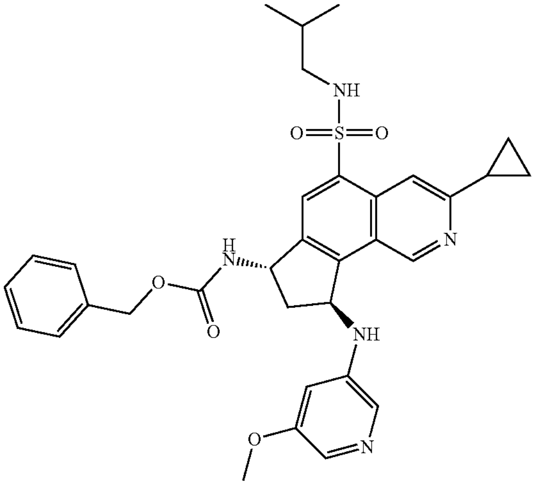

S,S and R,R benzyl N-[trans-(7SR,9SR)-3-cyclopropyl-5-(isobutylsulfamoyl)-9-[(5-methoxy-3-pyridyl)aminol-8,9-dihydro-7H-cyclopenta[h]isoquinolin-7-yl]carbamate In a pressure vial, 3-bromo-5-methoxypyridine (277 mg, 1.47 mmol), tBuXPhos Pd G3 (117 mg, 0.147 mmol), intermediate 19 (300 mg, 0.590 mmol) and sodium 2-methylpropan-2-olate (227 mg, 2.36 mmol) were suspended in 1,4-Dioxane (25 mL). The reaction was placed under nitrogen, capped, and the mixture was heated at 65° C. for 2.5 hours. The majority of the 1,4-dioxane was removed and the residue was loaded onto an SCX column. Purification by SCX column chromatography eluting with 0 to 100% of 7 M $NH_3$ in methanol gradient afforded an oil. It still contained multiple components. Further purification by flash column chromatography eluting with 0 to 5% of 7 M $NH_3$/MeOH in DCM gradient afforded the title compound as a mixture of enantiomers (208 mg, 57% yield); LCMS $[M+H]^+$ 616, RT 3.31 minutes (Method 1).

Intermediate 33

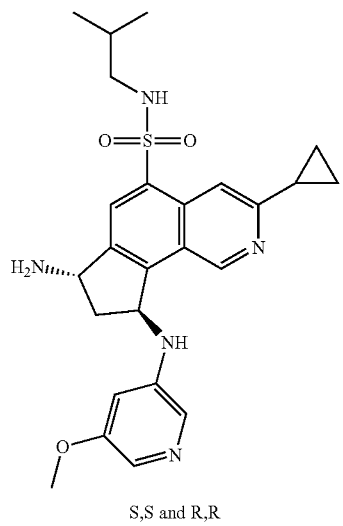 [SMILES: COc1cncc(N[C@H]2C[C@H](N)c3cc(S(=O)(=O)NCC(C)C)c4cc(C5CC5)ncc4c32)c1]

S,S and R,R

Trans-(7SR,9SR)-7-amino-3-cyclopropyl-N-isobutyl-9-[(5-methoxy-3-pyridyl)aminol-8,9-dihydro-7H-cyclopenta[h]isoquinoline-5-sulfonamide To a solution of intermediate 32 (283 mg, 0.460 mmol) in MeOH (5 mL) was added 10% Pd on carbon (10%, 264 mg, 0.248 mmol). The reaction was placed under hydrogen for 1 hour. The palladium residues were removed through Celite and the solvent was removed to give a pale-yellow solid. The solid was purified by flash column chromatography eluting with 0 to 10% of 7 M $NH_3$/MeOH in DCM gradient to afford the title compound as a mixture of enantiomers (195 mg, 88% yield); LCMS $[M+H]^+$ 482, RT 1.85 minutes (Method 1).

Intermediate 34

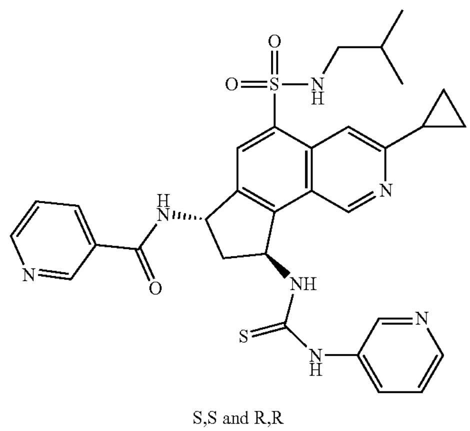 [SMILES: CC(C)CNS(=O)(=O)c1cc2c(c3cnc(C4CC4)cc13)[C@@H](NC(=S)Nc1cccnc1)C[C@@H]2NC(=O)c1cccnc1]

S,S and R,R

N-[trans-(7SR,9SR)-3-cyclopropyl-5-(isobutylsulfamoyl)-9-(3-pyridylcarbamothioylamino)-8,9-dihydro-7H-cyclopenta[h]isoquinolin-7-yl]pyridine-3-carboxamide To a solution of Example 3 (50 mg, 0.104 mmol) in THF (1 mL) was added 3-isothiocyanatopyridine (0.013 mL, 0.115 mmol). The solution was stirred for 10 minutes by which time a white solid had precipitated out of solution. The solid was filtered, washed with DCM (1 mL) and dried under vacuum to give the title compound as a mixture of enantiomers (32 mg, 49% yield). The filter paper was washed to give a 2nd crop of the title compound (16 mg, 25% yield). LCMS $[M+H]^+$ 616, RT 2.90 minutes (Method 4).

Intermediate 35

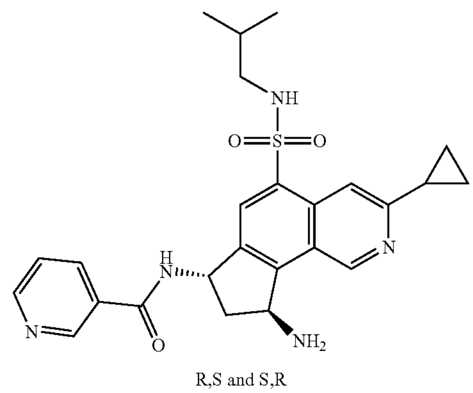 [SMILES: CC(C)CNS(=O)(=O)c1cc2c(c3cnc(C4CC4)cc13)[C@@H](N)C[C@@H]2NC(=O)c1cccnc1]

R,S and S,R

N-[cis-(7RS,9SR)-9-amino-3-cyclopropyl-5-(isobutylsulfamoyl)-8,9-dihydro-7H-cyclopenta[h]isoquinolin-7-yl]pyridine-3-carboxamide To a suspension of Example 2 (275 mg, 0.474 mmol) in DCM (2.5 mL) was added trifluoroacetic acid (2.5 mL, 33.7 mmol). The resulting solution was stirred at room temperature for 45 minutes. The solvent was removed from the reaction azeotroping with 1:1 DCM/heptane to remove the excess TFA. The gum was purified by SCX column chromatography eluting with 0 to 10% of 7 M $NH_3$ in MeOH gradient to afford the title compound as a mixture of enantiomers (226 mg, 97% yield); LCMS $[M+H]^+$ 480, RT 1.60 minutes (Method 2).

Intermediate 36

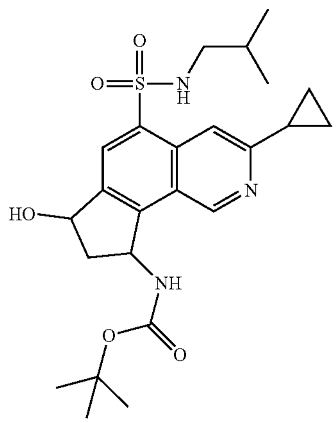 [SMILES: CC(C)CNS(=O)(=O)c1cc2c(c3cnc(C4CC4)cc13)C(NC(=O)OC(C)(C)C)CC2O]

tert-butyl N-[3-cyclopropyl-7-hydroxy-5-(isobutylsulfamoyl)-8,9-dihydro-7H-cyclopenta[h]isoquinolin-9-yl]carbamate A suspension of intermediate 14 (350 mg, 0.76 mmol), 2,2'-azobis(2-methylpropionitrile) (13 mg, 0.078 mmol and N-bromosuccinimide (165 mg, 0.927 mmol) in ethyl acetate (10 mL) was stirred and heated at 100° C. in a microwave for 1 h. The reaction was concentrated in vacuo to give a brown oil which was dissolved in tetrahydrofuran (8 mL) and water (2 mL) and to which was added silver carbonate (425 mg, 1.53 mmol) at room temperature. Reaction complete by LCMS after 2.5 hours. Reaction diluted with ethyl acetate, filtered, the solvent removed, and the residue purified by column chromatography (eluting with a gradient of ethyl acetate in iso-hexane) to give the title compound as a brown oil (95 mg, 26%) as a mixture (~2:1) of diastereoisomers. LCMS $[M+H]^+$ 476 with retention times 1.18 min and 1.21 min (Method 8).

Intermediate 37

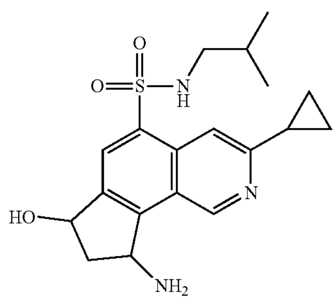 [SMILES: CC(C)CNS(=O)(=O)c1cc2c(c3cnc(C4CC4)cc13)C(N)CC2O]

9-amino-3-cyclopropyl-7-hydroxy-N-isobutyl-8,9-dihydro-7H-cyclopenta[h]isoquinoline-5-sulfonamide A solution of Intermediate 36 (32 mg, 0.067 mmol) and trifluoroacetic acid (0.5 mL) in dichloromethane (0.5 mL) was stirred at room temperature. After 30 min the reaction was quenched with saturated $NaHCO_3$ solution (4 mL) and stirred for 1 h. The solution was diluted with 30% isopropyl alcohol in chloroform (10 mL) and the layers separated. The aqueous layer was further extracted with 30% isopropyl alcohol in chloroform (3×5 mL) and the combined organics washed with brine (5 mL), dried, and concentrated in vacuo to give the title compound as a brown oil as a mixture (~2:1) of diastereoisomers. LCMS $[M+H]^+$ 376 with retention times 0.904 min and 0.939 min (Method 8).

Intermediate 38

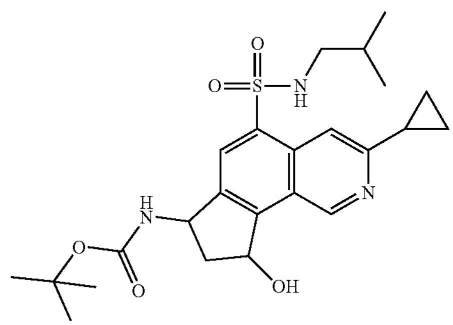 [SMILES: CC(C)CNS(=O)(=O)c1cc2c(c3cnc(C4CC4)cc13)C(O)CC2NC(=O)OC(C)(C)C]

tert-butyl N-[3-cyclopropyl-9-hydroxy-5-(isobutylsulfamoyl)-8,9-dihydro-7H-cyclopenta[h]isoquinolin-7-yl]carbamate A suspension of Intermediate 13 (223 mg, 0.485 mmol), 2,2'-azobis(2-methylpropionitrile) (8 mg, 0.048 mmol) and N-bromosuccinimide (100 mg, 0.562 mmol) in ethyl acetate (5 mL) was heated at 100° C. for 1.5 hours in a microwave. The reaction was concentrated in vacuo to give a brown solid which was dissolved in tetrahydrofuran (8 mL) and water (2 mL) and to which was added silver carbonate (425 mg, 1.53 mmol). Reaction stirred at room temp overnight then diluted with ethyl acetate, filtered, washed with brine (20 mL), dried ($Na_2SO_4$), filtered and concentrated in vacuo. The residue was purified by column chromatography eluting with a gradient of ethyl acetate in iso-hexane to give the title compound as a brown oil (60 mg, 26%) as a mixture (~1:1) of diastereoisomers. LCMS $[M+H]^+$ 476 with retention times 1.235 min and 1.263 min (Method 8).

Intermediate 39

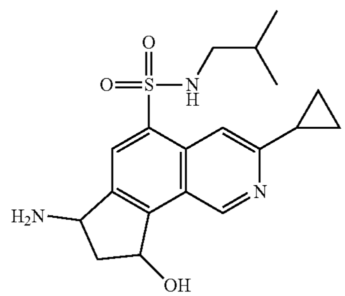 [SMILES: CC(C)CNS(=O)(=O)c1cc2c(c3cnc(C4CC4)cc13)C(O)CC2N]

7-amino-3-cyclopropyl-9-hydroxy-N-isobutyl-8,9-dihydro-7H-cyclopenta[h]isoquinoline-5-sulfonamide To a solution of Intermediate 38 (41 mg, 0.086 mmol) in dichloromethane (1 mL) was added trifluoroacetic acid (0.5 mL) dropwise. After 30 min the reaction was quenched with saturated $NaHCO_3$ (3 mL), stirred at room temp for 1 hour, the layers separated, and the aqueous phase extracted with 30% isopropyl alcohol in chloroform (2×5 mL). The combined organics were dried and concentrated in vacuo to give the title compound as a mixture (~1:1) of diastereoisomers (23 mg, 72%). LCMS $[M+H]^+$ 376 with retention times 0.955 min and 0.926 min (Method 8).

Intermediate 40

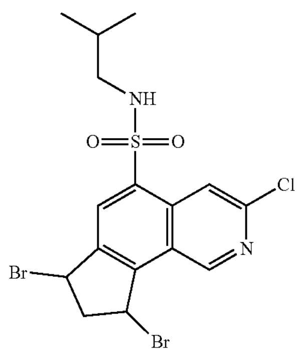 [SMILES: CC(C)CNS(=O)(=O)c1cc2c(c3cnc(Cl)cc13)C(Br)CC2Br]

7,9-dibromo-3-chloro-N-isobutyl-8,9-dihydro-7H-cyclopenta[h]isoquinoline-5-sulfonamide To a solution of intermediate 6 (9 g, 26.5 mmol) in ethyl acetate (360 mL), 2,2'-azobis(2-methylpropionitrile) (445 mg, 2.65 mmol) and N-bromosuccinimide (11.8 g, 66.4 mmol) were added. The reaction mixture was sealed and heated at 90° C. for 3 h. The reaction mixture was washed with water (300 mL) and dried over $Na_2SO_4$. The solvent was removed in vacuo to give the crude title compound as a mixture of enantiomers (13.2 g, quantitative) which was used in the next stage without further purification.

Intermediate 41

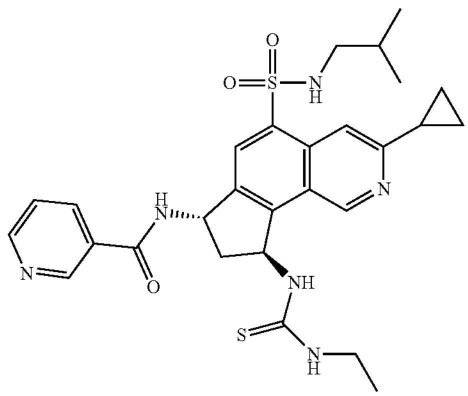

S,S and R,R

N-[trans-(7SR,9SR)-3-cyclopropyl-9-(ethylcarbamothioylamino)-5-(isobutylsulfamoyl)-8,9-dihydro-7H-cyclopenta[h]isoquinolin-7-yl]pyridine-3-carboxamide To a solution of Example 3 (50 mg, 0.104 mmol) in THF (1 mL) was added isothiocyanatoethane (0.010 mL, 0.115 mmol). The solution was stirred for 60 minutes. Another portion of isothiocyanatoethane (0.010 mL, 0.115 mmol) was added and the solution was stirred for 1 hour. The solvent was removed to give a white solid. Trituration with DCM gave the title compound as a mixture of enantiomers (55 mg, 87% yield). LCMS $[M+H]^+$ 567, RT 3.03 minutes (Method 3).

Intermediate 42

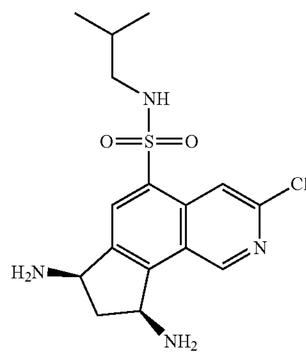

R,S and S,R

Cis-(7RS,9SR)-7,9-diamino-3-chloro-N-isobutyl-8,9-dihydro-7H-cyclopenta[h]isoquinoline-5-sulfonamide Intermediate 27 (1.2 g, 2.85 mmol) was dissolved in ethanol (12 mL) and palladium on carbon (0.28 mmol) added. The solution was degassed and placed under an atmosphere of hydrogen. Additional portions of palladium on carbon were added until reaction had gone to completion. The reaction mixture was then filtered through celite, washing with EtOH (15 mL). The solvents were removed, and the crude purified by column chromatography eluting with a 0-100% gradient of MeOH in DCM to give the title compound as a mixture of enantiomers (851 mg, 52% Yield). $^1H$ NMR (300 MHz, Methanol-d4) $\delta_H$ 9.68 (d, J=0.8 Hz, 1H), 8.55 (d, J=0.8 Hz, 1H), 8.46 (s, 1H), 4.87 (dd, J=7.8, 5.3 Hz, 1H), 4.35 (dd, J=8.0, 5.5 Hz, 1H), 3.07 (dt, J=13.7, 7.9 Hz, 1H), 2.70-2.53 (m, 2H), 1.75 (dt, J=13.7, 5.4 Hz, 1H), 1.65-1.50 (m, 1H), 0.81-0.66 (m, 6H). LCMS (ES) m/z=369 $(M+H)^+$, RT=1.76 (Method 12)

Intermediate 43

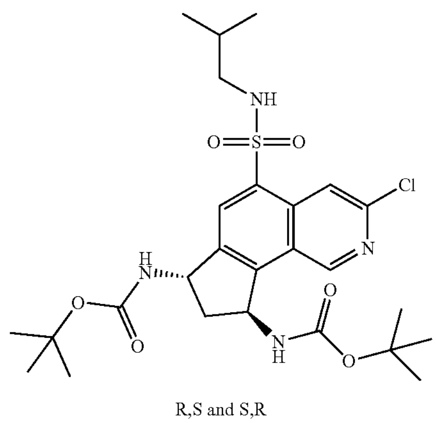 [SMILES: CC(C)CNS(=O)(=O)c1cc2c(c3cnc(Cl)cc13)[C@@H](NC(=O)OC(C)(C)C)C[C@@H]2NC(=O)OC(C)(C)C]

R,S and S,R tert-butyl N-[cis-(7RS,9SR)-7-(tert-butoxycarbonylamino)-3-chloro-5-(isobutylsulfamoyl)-8,9-dihydro-7H-cyclopenta[h]isoquinolin-9-yl]carbamate To a stirred solution of intermediate 42 (3.7 g, 7.0 mmol) in 1,4-dioxane (80 mL) was added di-tert-butyl dicarbonate (3.8 g, 18 mmol) followed by triethylamine (3.9 mL, 28 mmol). The reaction was stirred at ambient temperature overnight. The reaction mixture was diluted with water (80 mL) and DCM (100 mL). The organic phase was partitioned, and the aqueous layer extracted with DCM (100 mL). The combined organic extracts were dried and concentrated in vacuo. The crude was purified by flash column chromatography eluting with a 0-40% gradient of EtOAc in isohexane to give the title compound as a mixture of enantiomers (3.7 g, 7.0 mmol). $^1$H NMR (400 MHz, Chloroform-d) $\delta_H$ 9.44 (s, 1H), 8.48 (d, J=0.9 Hz, 1H), 8.37 (s, 1H), 5.79 (s, 1H), 5.68 (dt, J=13.4, 6.5 Hz, 1H), 5.41 (s, 1H), 5.05-4.91 (m, 1H), 4.80-4.66 (m, 1H), 3.26 (dt, J=14.4, 8.8 Hz, 1H), 2.83-2.63 (m, 2H), 2.13-2.06 (m, 1H), 1.69 (dp, J=13.4, 6.7 Hz, 1H), 1.46 (s, 9H), 1.43 (s, 9H), 0.82 (dd, J=6.7, 2.2 Hz, 6H). LCMS [M+H]$^+$ 569, RT 1.67 (Method 7).

Intermediate 44

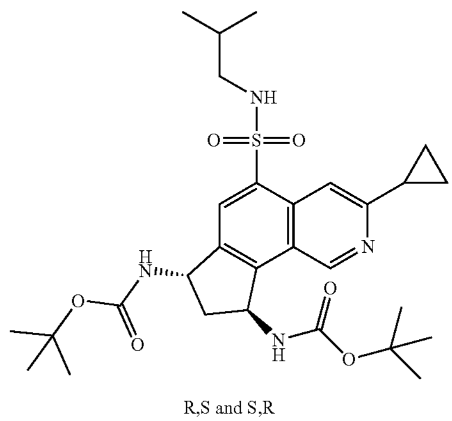 [SMILES: CC(C)CNS(=O)(=O)c1cc2c(c3cnc(C4CC4)cc13)[C@@H](NC(=O)OC(C)(C)C)C[C@@H]2NC(=O)OC(C)(C)C]

R,S and S,R tert-butyl N-[cis-(7RS,9SR)-7-(tert-butoxycarbonylamino)-3-cyclopropyl-5-(isobutylsulfamoyl)-8,9-dihydro-7H-cyclopenta[h]isoquinolin-9-yl]carbamate To a stirred suspension of intermediate 43 (2 g, 3.51 mmol) in toluene (20 mL), 1,4-dioxane (20 mL) and water (1 mL) were added cyclopropylboronic acid (1.27 g, 14.1 mmol), potassium phosphate tribasic (2.66 g, 12.3 mmol), tricyclohexylphosphonium tetrafluoroborate (334 mg, 0.879 mmol) and palladium(II) acetate (121 mg, 0.527 mmol). The reaction mixture was placed under an atmosphere of nitrogen and heated at 100° C. in a sealed pressure flask overnight. The reaction was cooled and diluted with DCM (100 mL) and water (50 mL). The organic phase was partitioned, and the aqueous layer extracted with DCM (2×50 mL). The organic layer was dried and concentrated in vacuo. The crude was purified by column chromatography eluting with a 0-45% gradient of EtOAc in isohexane to give the title compound as a mixture of enantiomers (1.25 g, 59% Yield). $^1$H NMR (400 MHz, Chloroform-d) $\delta_H$ 9.48 (s, 1H), 8.31 (s, 1H), 8.24 (s, 1H), 5.79-5.62 (m, 1H), 5.62-5.49 (m, 1H), 5.49-5.32 (m, 1H), 5.17-4.95 (m, 1H), 4.94-4.74 (m, 1H), 3.29-3.12 (m, 1H), 2.84-2.57 (m, 2H), 2.29-2.16 (m, 1H), 2.06-1.97 (m, 1H), 1.75-1.63 (m, 1H), 1.45 (s, 18H), 1.18-1.01 (m, 4H), 0.83 (dd, J=6.7, 3.3 Hz, 6H). LCMS [M+H]$^+$ 575, RT 3.08 (Method 7).

Intermediate 45

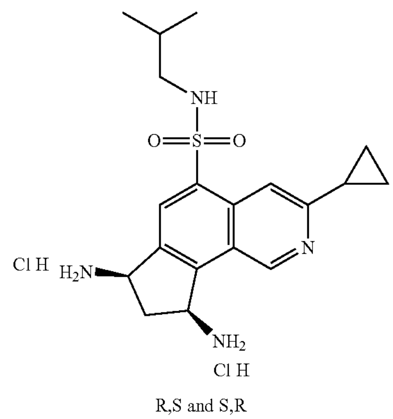

R,S and S,R

Cis-(7RS,9SR)-7,9-diamino-3-cyclopropyl-N-isobutyl-8,9-dihydro-7H-cyclopenta[h]isoquinoline-5-sulfonamide dihydrochloride To a stirred suspension of intermediate 44 (1.25 g, 2.18 mmol) in methanol (20 mL) at ambient temperature was added hydrochloric acid 4 M in dioxane (11 mL, 44 mmol). The reaction was stirred at ambient temperature overnight. The reaction mixture was concentrated in vacuo and the resulting solids triturated in diethyl ether (10 mL) and filtered, washing with additional diethyl ether (10 mL). The solids were dried to give the title compound as a bis HCl salt and a mixture of enantiomers (1.02 g, quantitative). $^1$H NMR (400 MHz, Methanol-d4) $\delta_H$ 9.80 (d, J=0.9 Hz, 1H), 8.80 (s, 1H), 8.66 (d, J=0.9 Hz, 1H), 5.71 (dd, J=8.9, 2.8 Hz, 1H), 5.12 (dd, J=9.3, 3.1 Hz, 1H), 3.58-3.47 (m, 1H), 2.72 (d, J=7.0 Hz, 2H), 2.60-2.42 (m, 2H), 1.64 (hept, J=6.8 Hz, 1H), 1.38-1.23 (m, 4H), 0.79 (d, J=6.7 Hz, 6H). LCMS $[M+H]^+$ 375, RT 1.54 (Method 15).

Intermediate 46

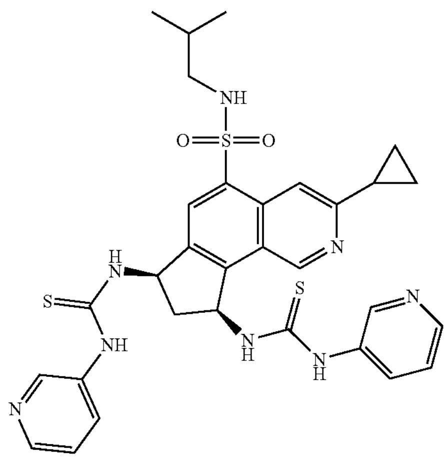

R,S and S,R

1-[cis-(7RS,9SR)-3-cyclopropyl-5-(isobutylsulfamoyl)-7-(3-pyridylcarbamothioylamino)-8,9-dihydro-7H-cyclopenta[h]isoquinolin-9-yl]-3-(3-pyridyl)thiourea To a stirred suspension of intermediate 45 (100 mg, 0.26 mmol) in DCM (4 mL) at room temperature was added 3-isothiocyanatopyridine (74.5 μL, 0.66 mmol). The reaction was stirred at ambient temperature for 30 min. A second portion of 3-isothiocyanatopyridine (16 μL) was added and stirring continued for 30 min. The reaction was filtered, washing with diethyl ether (5 mL). The solid was triturated and filtered using first DCM/MeOH (9:1) then MeOH to give the title compound as a mixture of enantiomers (117 mg, 67% Yield). $^1H$ NMR (400 MHz, DMSO-d6) $\delta_H$ 9.99-9.73 (m, 2H), 9.43 (s, 1H), 8.68-8.47 (m, 3H), 8.46-8.26 (m, 4H), 8.25-8.11 (m, 1H), 7.96 (dd, J=26.4, 8.2 Hz, 2H), 7.51-7.29 (m, 2H), 6.78-6.56 (m, 1H), 6.23-5.90 (m, 1H), 2.72-2.54 (m, 2H), 2.38-2.18 (m, 1H), 2.15-1.93 (m, 1H), 1.74-1.51 (m, 1H), 1.17-0.99 (m, 4H), 0.88-0.67 (m, 6H). LCMS $[M+H]^+$ 647, RT 2.19 (Method 15).

Intermediates 47 & 47a

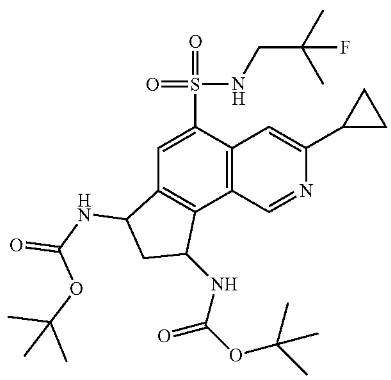

-continued

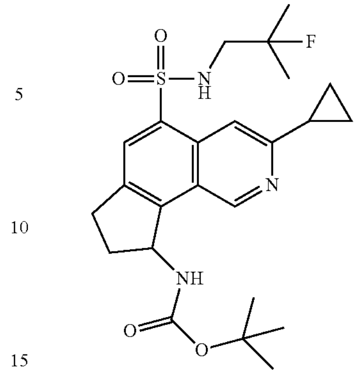

tert-butyl N-[7-(tert-butoxycarbonylamino)-3-cyclopropyl-5-[(2-fluoro-2-methyl-propyl)sulfamoyl]-8,9-dihydro-7H-cyclopenta[h]isoquinolin-9-yl]carbamate (47)

tert-butyl N-[3-cyclopropyl-5-[(2-fluoro-2-methyl-propyl)sulfamoyl]-8,9-dihydro-7H-cyclopenta[h]isoquinolin-9-yl]carbamate (47a)

A mixture of intermediates 29a and 29 in a ~5.5:1 ratio, respectively (1135 mg, 2.40 mmol) was taken up in toluene (10 mL). Cyclopropylboronic acid (652 mg, 7.21 mmol) and palladium(II)acetate (27 mg, 0.120 mmol) were added and the mixture was degassed, vacuum/nitrogen purge (×3). Tricyclohexylphosphonium tetrafluoroborate (137 mg, 0.361 mmol) and a solution of potassium phosphate tribasic (1280 mg, 6.01 mmol) in water (1 mL) was added and the mixture degassed again, vacuum/nitrogen purge (×3). The reaction mixture was heated at 120° C. for 2 h in the microwave. After cooling the mixture was diluted with EtOAc (100 mL) and the solution washed with water and then brine, passed through a phase separator cartridge and evaporated. The crude product was purified by flash chromatography eluting with a gradient of 10-60% EtOAc/hexane to afford the title compounds:

Intermediate 47 (156 mg); LCMS [M+H]+ 593, RT 2.89 minutes (Method 17).

Intermediate 47a (938 mg); LCMS [M+H]+ 478, RT 2.70 minutes (Method 15).

Intermediate 48

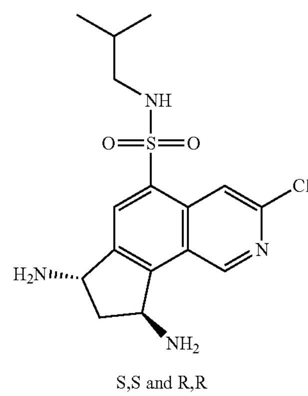 [SMILES: CC(C)CNS(=O)(=O)c1cc2c(c3cnc(Cl)cc13)[C@@H](N)C[C@@H]2N]

S,S and R,R

Trans-(7SR,9SR)-7,9-diamino-3-chloro-N-isobutyl-8,9-dihydro-7H-cyclopenta[h]isoquinoline-5-sulfonamide To a stirred solution of intermediate 28 (3.25 g, 7.72 mmol) in THF (80 mL) and $H_2O$ (10 mL) was added triphenylphosphine (4.95 g, 18.7 mmol). The reaction mixture was heated at 50° C. for 30 min prior to the further addition of $H_2O$ (20 mL). After a further 23 h, additional triphenylphosphine (1.0 g, 3.8 mmol) was added and heating continued at 50° C. o/n. The reaction mixture was then concentrated in vacuo and purified by using an SCX cartridge eluting with 7 N $NH_3$ in MeOH to give the title compound as a mixture of enantiomers (3.31 g, 93% yield). LCMS $[M+H]^+$ 369, RT 1.16 minutes (Method 13).

Intermediate 49

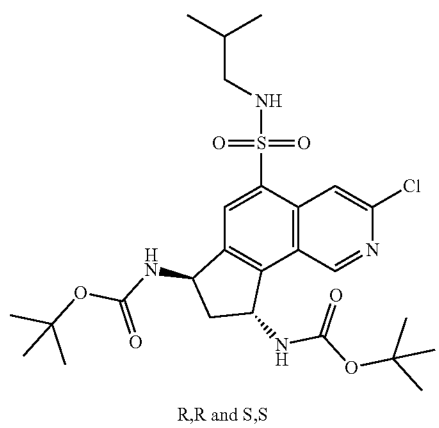 [SMILES: CC(C)CNS(=O)(=O)c1cc2c(c3cnc(Cl)cc13)[C@H](NC(=O)OC(C)(C)C)C[C@H]2NC(=O)OC(C)(C)C]

R,R and S,S tert-butyl N-[trans-(7RS,9RS)-7-(tert-butoxycarbonylamino)-3-chloro-5-(isobutylsulfamoyl)-8,9-dihydro-7H-cyclopenta[h]isoquinolin-9-yl]carbamate To a stirred solution of intermediate 48 (3.31 g, 7.17 mmol) in anhydrous 1,4-dioxane (80 mL) at r.t. were added TEA (4 mL, 28.7 mmol) and di-tert-butyl dicarbonate (4.1 g, 18 mmol). After 1 h 15 min, the reaction mixture was concentrated to half the volume, diluted with a mixture of DCM (100 mL) and sat. $NaHCO_3$ (100 mL), and the phases separated. The aqueous phase was extracted with DCM (3×30 mL) and the combined organics dried (MgSO4) and conc. in vacuo. Purification by column chromatography eluting with 0-30% EtOAc in iso-hexane gave the title compound as a mixture of enantiomers (2.20 g, 54% yield). LCMS $[M+H]^+$ 569, RT 2.46 minutes (Method 13).

Intermediate 50

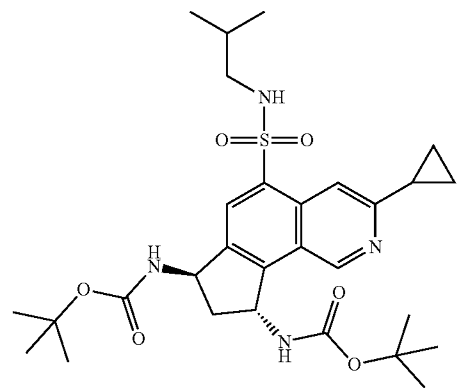 [SMILES: CC(C)CNS(=O)(=O)c1cc2c(c3cnc(C4CC4)cc13)[C@H](NC(=O)OC(C)(C)C)C[C@H]2NC(=O)OC(C)(C)C]

tert-butyl N-[trans-(7RS,9RS)-7-(tert-butoxycarbonylamino)-3-cyclopropyl-5-(isobutylsulfamoyl)-8,9-dihydro-7H-cyclopenta[h]isoquinolin-9-yl]carbamate To a stirred suspension of intermediate 49 (2.15 g, 3.78 mmol) in a mixture of toluene (20 mL), 1,4-dioxane (20 mL) and $H_2O$ (1 mL) were added cyclopropylboronic acid (1.36 g, 15 mmol), potassium phosphate tribasic (2.9 g, 13 mmol), tricyclohexylphosphonium tetrafluoroborate (360 mg, 0.95 mmol) and palladium (II) acetate (130 mg, 0.5675 mmol). The mixture was placed under an atmosphere of $N_2$ and heated at 100° C. in a sealed pressure round bottom flask. After 4 h 25 min, the reaction mixture was diluted with a mixture of DCM (100 mL with a few mL of IPA) and $H_2O$ (200 mL) and the phase separated. The aqueous was extracted with DCM (100 mL with a few mL of IPA), DCM (4×30 mL), the combined organics dried (MgSO4), filtered and conc. in vacuo. Purification by column chromatography eluting with 0-40% EtOAc in iso-hexane gave the title compound as a mixture of enantiomers (1.84 g, 80% yield). LCMS $[M+H]^+$ 575, RT 2.49 minutes (Method 13).

Intermediate 51

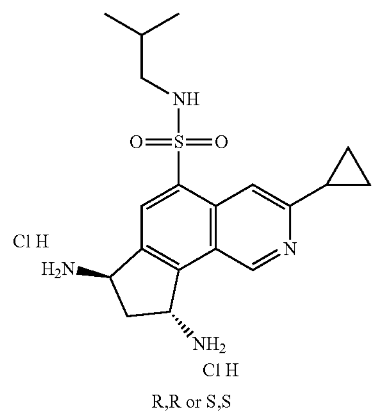

R,R or S,S

Trans-(7RS,9RS)-7,9-diamino-3-cyclopropyl-N-isobutyl-8,9-dihydro-7H-cyclopenta[h]isoquinoline-5-sulfonamide dihydrochloride To a stirred yellow semi-solution of intermediate 50 (1.8 g, 3.1 mmol) in MeOH (60 mL) in an ice-bath was added hydrochloric acid (4.0 mol/L) in dioxane (33 mL). The reaction mixture was then raised to r.t. and stirred for 4 h 30 min then concentrated in vacuo. The crude was triturated with $Et_2O$ (20 mL), filtered and washed with $Et_2O$ (20 mL). The residue was dried in vacuo to give the title compound as a mixture of enantiomers (1.51 g, quantitative). LCMS $[M+H]^+$ 375, RT 0.76 minutes (Method 8).

Intermediate 52

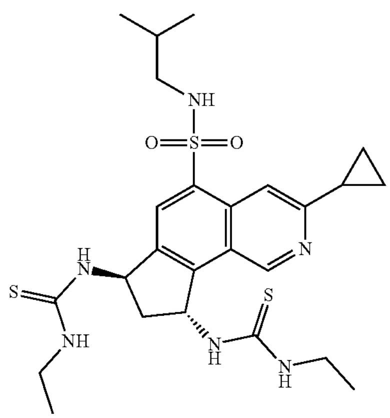

R,R and S,S

1-[trans-(7RS,9RS)-3-cyclopropyl-7-(ethylcarbamothioylamino)-5-(isobutylsulfamoyl)-8,9-dihydro-7H-cyclopenta[h]isoquinolin-9-yl]-3-ethyl-thiourea Following general procedure 1 using intermediate 51 (600 mg, 1.30 mmol) with a heating time of 10 h. The reaction mixture was concentrated in vacuo, triturated with $Et_2O$ (80 mL) and filtered to give the title compound as a mixture of enantiomers (623 mg, 87% yield). LCMS $[M+H]^+$ 549, RT 1.04 minutes (Method 8).

Intermediate 53

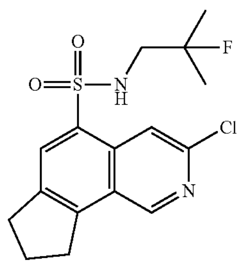 [SMILES: CC(C)(F)CNS(=O)(=O)c1cc2c(c3cnc(Cl)cc13)CCC2]

3-chloro-N-(2-fluoro-2-methyl-propyl)-8,9-dihydro-7H-cyclopenta[h]isoquinoline-5-sulfonamide To a stirred solution of intermediate 5 (11.5 g, 38.1 mmol) in DCM (200 mL) was added 2-fluoro-2-methyl-propan-1-amine hydrochloride (5.83 g, 45.7 mmol) followed by triethylamine (13.2 mL, 95.1 mmol). The reaction mixture was stirred at room temperature for 1 h. The reaction was washed with water (200 mL). The organic layer was partitioned and washed with more water (200 mL). The organic layer was dried and concentrated in vacuo to afford 11.8 g of green/black solid. This was triturated with hot IPA and filtered to give the title compound (10.4 g, 77% Yield) as a grey powder. $^1H$ NMR (300 MHz, Chloroform-d) $\delta_H$ 9.14 (d, J=0.9 Hz, 1H), 8.46 (d, J=0.8 Hz, 1H), 8.34 (s, 1H), 4.98 (t, J=6.5 Hz, 1H), 3.49-3.37 (m, 2H), 3.17 (t, J=7.5 Hz, 2H), 3.04 (dd, J=19.8, 6.5 Hz, 2H), 2.45-2.29 (m, 2H), 1.31 (d, J=21.4 Hz, 6H). LCMS $[M+H]^+$ 357, RT 1.92 (Method 14).

Intermediate 54

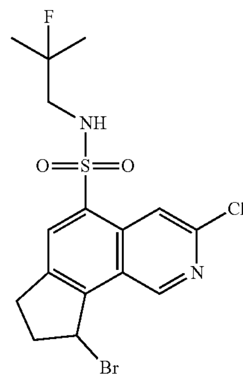 [SMILES: CC(C)(F)CNS(=O)(=O)c1cc2c(c3cnc(Cl)cc13)C(Br)CC2]

9-bromo-3-chloro-N-(2-fluoro-2-methyl-propyl)-8,9-dihydro-7H-cyclopenta[h]isoquinoline-5-sulfonamide To a stirred solution of intermediate 53 (10.47 g, 29.3 mmol) in EtOAc (500 mL), 2,2'-azobis(2-methylpropionitrile) (506 mg, 3 mmol) and N-bromosuccinimide (6.24 g, 34.7 mmol) were added. The reaction mixture was stirred at 90° C. in the dark for 1.5 h. The reaction was cooled and concentrated. Residual succinimide was filtered off and the crude purified by column chromatography eluting with a gradient of 0-25% EtOAc in isohexane to give the title compound (5.07 g, 44% Yield). $^1H$ NMR (300 MHz, Chloroform-d) $\delta_H$ 9.34 (d, J=0.8 Hz, 1H), 8.49 (d, J=0.8 Hz, 1H), 8.36 (s, 1H), 6.02 (dd, J=4.6, 2.6 Hz, 1H), 5.04 (t, J=6.4 Hz, 1H), 3.47-3.32 (m, 1H), 3.17-3.04 (m, 3H), 2.85-2.75 (m, 2H), 1.33 (dd, J=21.4, 4.7 Hz, 6H). LCMS $[M+H]^+$ 434/436, RT 2.57 (Method 14).

Intermediate 55

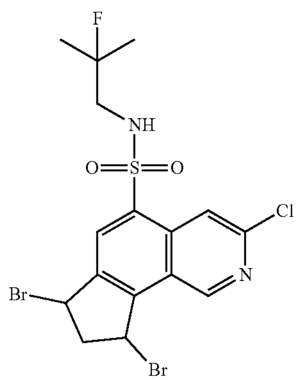 [SMILES: CC(C)(F)CNS(=O)(=O)c1cc2c(c3cnc(Cl)cc13)C(Br)CC2Br]

7,9-dibromo-3-chloro-N-(2-fluoro-2-methyl-propyl)-8,9-dihydro-7H-cyclopenta[h]isoquinoline-5-sulfonamide A vial was charged with Intermediate 54 (750 mg, 1.72 mmol), N-bromosuccinimide (360 mg, 2.02 mmol), 2,2'-azobis(2-methylpropionitrile) (30 mg, 0.179 mmol) and EtOAc (30 mL), sealed and then heated at 90° C. for 4 h. The reaction mixture was conc. in vacuo and purified by column chromatography eluting with 0-100% EtOAc in iso-hexane to give the title compound (779 mg, 84% yield) as a mixture of cis and trans isomers. LCMS $[M+H]^+$ 515, RT 2.70 minutes (cis isomer) and RT 2.79 minutes (trans isomer) (Method 12).

Intermediates 56 & 57

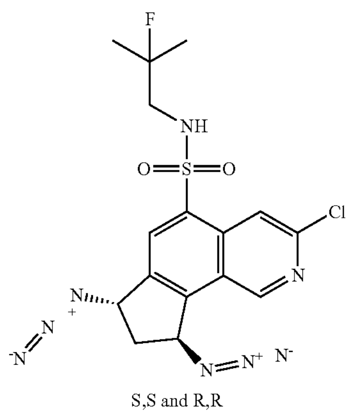

S,S and R,R

-continued

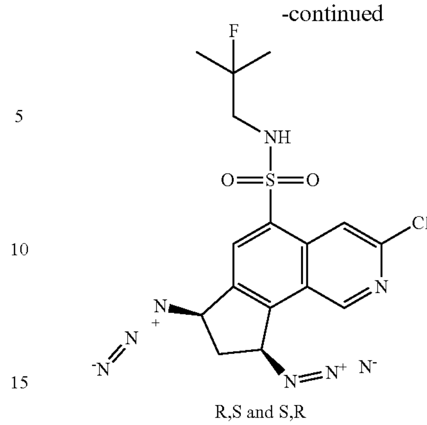

R,S and S,R

Trans-(7SR,9SR)-7,9-diazido-3-chloro-N-(2-fluoro-2-methyl-propyl)-8,9-dihydro-7H-cyclopenta[h]isoquinoline-5-sulfonamide (56) Cis-(7RS,9SR)-7,9-diazido-3-chloro-N-(2-fluoro-2-methyl-propyl)-8,9-dihydro-7H-cyclopenta[h]isoquinoline-5-sulfonamide (57)

To a stirred solution of intermediate 55 (779 mg, 1.45 mmol) in anhydrous DMF (5 mL) was added sodium azide (240 mg, 3.65 mmol). The reaction mixture was stirred at r.t. for 1 h 35 min then diluted with EtOAc (30 mL) and washed with brine (60 mL). The aqueous phase was extracted with EtOAc (2×20 mL) and the combined organics dried (phase separator) and concentrated in vacuo. Purification by column chromatography eluting with 0-30% EtOAc in iso-hexane gave the title compounds as mixtures of enantiomers:

Intermediate 56 (239 mg, 37% yield), LCMS $[M+H]^+$ 439, RT 1.54 minutes (Method 7).

Intermediate 57 (293 mg, 46% yield), LCMS $[M+H]^+$ 439, RT 1.53 minutes (Method 7).

Intermediate 58

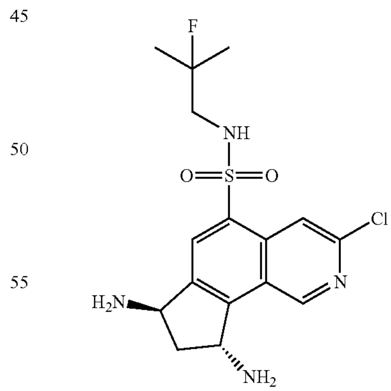

Trans-(7RS,9RS)-7,9-diamino-3-chloro-N-(2-fluoro-2-methyl-propyl)-8,9-dihydro-7H-cyclopenta[h]isoquinoline-5-sulfonamide Synthesised in the same manner as intermediate 48 using intermediate 56 (280 mg, 0.64 mmol) and comparable stoichiometries of reagents. Purification using an SCX cartridge eluting with 7 N $NH_3$ in MeOH gave the title compound as a mixture of enantiomers (255 mg, 83% yield). LCMS $[M+H]^+$ 387, RT 1.01 minutes (Method 13).

Intermediate 59

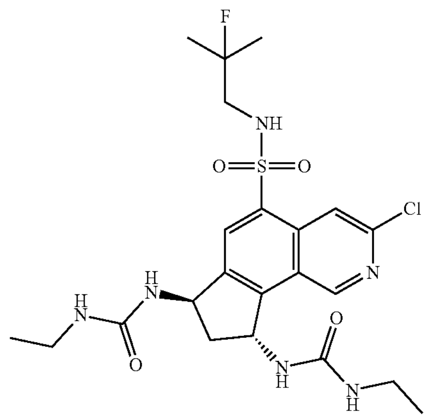

R,R and S,S

1-[trans-(7RS,9RS)-3-chloro-7-(methylcarbamoylamino)-5-[(2-fluoro-2-methyl-propyl)sulfamoyl]-8,9-dihydro-7H-cyclopenta[h]isoquinolin-9-yl]-3-ethyl-urea Following general procedure 1 using intermediate 58 (142 mg, 0.31 mmol) at r.t. Purification by column chromatography eluting with 0-10% MeOH in DCM gave the title compound as a mixture of enantiomers (74 mg, 45% yield). LCMS $[M+H]^+$ 529, RT 1.32 minutes (Method 13).

Intermediate 60

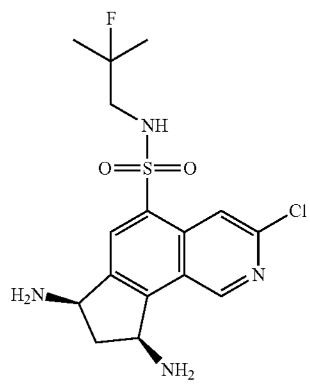 [SMILES: CC(C)(F)CNS(=O)(=O)c1cc2c(c3cnc(Cl)cc13)[C@H](N)C[C@H]2N]

R,S and S,R

Cis-(7RS,9SR)-7,9-diamino-3-chloro-N-(2-fluoro-2-methyl-propyl)-8,9-dihydro-7H-cyclopenta[h]isoquinoline-5-sulfonamide Synthesised in the same manner as intermediate 48 using intermediate 57 (240 mg, 0.55 mmol) and comparable stoichiometries of reagents. Purification using an SCX cartridge eluting with 7 N $NH_3$ in MeOH gave the title compound as a mixture of enantiomers (209 mg, 79% yield). LCMS $[M+H]^+$ 387, RT 1.09 minutes (Method 13).

Intermediate 61

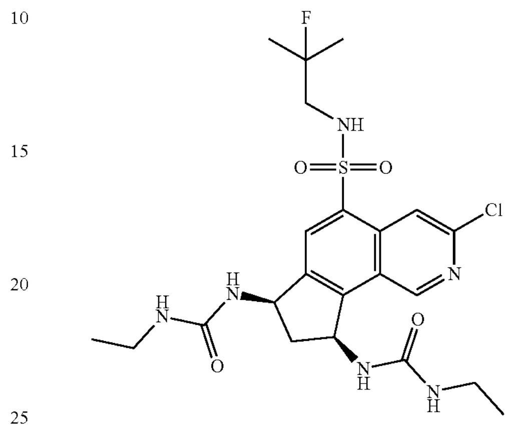

R,S and S,R

1-[cis-(7RS,9SR)-3-chloro-7-(methylcarbamoylamino)-5-[(2-fluoro-2-methyl-propyl)sulfamoyl]-8,9-dihydro-7H-cyclopenta[h]isoquinolin-9-yl]-3-ethyl-urea Following general procedure 1 with intermediate 60 (100 mg, 0.22 mmol) at room temperature. Purification by column chromatography eluting with 0-10% MeOH in DCM gave the title compound as a mixture of enantiomers (68 mg, 59% yield). LCMS $[M+H]^+$ 529, RT 1.34 minutes (Method 13).

Intermediate 62

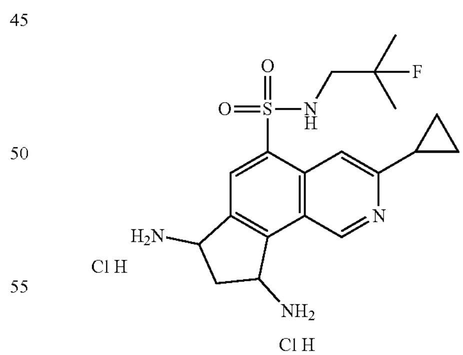

7,9-diamino-3-cyclopropyl-N-(2-fluoro-2-methyl-propyl)-8,9-dihydro-7H-cyclopenta[h]isoquinoline-5-sulfonamide dihydrochloride Intermediate 47 (153 mg, 0.258 mmol) was dissolved in 4 N HCl in dioxane (5 mL). Stirred at room temperature for 1 h. The solvent was removed in vacuo to afford the title compound (120 mg, quantitative) which was used without any further purification. LCMS [M+H]+ 393, RT 0.83 minutes (Method 8).

Examples 1 & 2

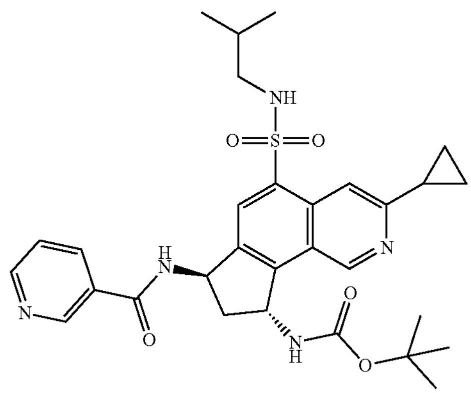

R,R and S,S

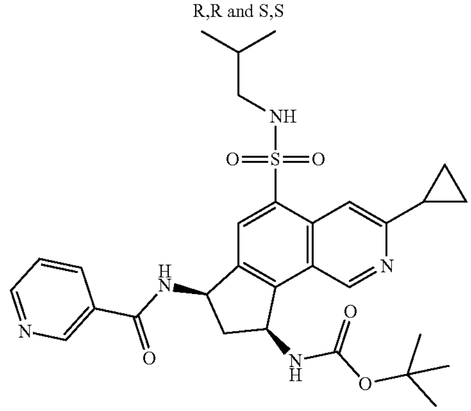

R,S and S,R tert-butyl N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]carbamate (1) tert-butyl N-[cis-(7RS,9SR)-3-cyclopropyl-5-(2-methylpropylsulfamoyl)-7-(pyridine-3-carbonylamino)-8,9-dihydro-7H-cyclopenta[h]isoquinolin-9-yl]carbamate (2)

To a solution of intermediate 26 (1870 mg, 3.94 mmol) in THF (15 mL) at 0° C. was added DIPEA (2.4 mL, 13.8 mmol) and pyridine-3-carbonyl chloride hydrochloride (912 mg, 5.12 mmol). The solution was stirred at room temperature for 10 minutes. The solvent was removed to give a brown solid. The solid was purified by flash column chromatography eluting with 0 to 100% of ethyl acetate in heptane gradient followed by a gradient of 0 to 5% 7 M $NH_3$/MeOH in DCM to give the title compounds a mixture of enantiomers:

Example 1 (980 mg, 42% yield); LCMS $[M+H]^+$ 580, RT 2.93 minutes (Method 1).

Example 2 (1240 mg, 51% yield); LCMS $[M+H]^+$ 580, RT 2.98 minutes (Method 1).

Example-3

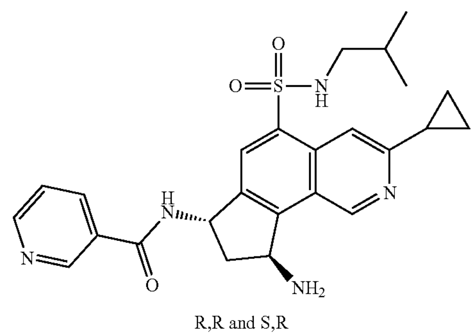 [SMILES: CC(C)CNS(=O)(=O)c1cc2c(c3cnc(C4CC4)cc13)[C@@H](N)C[C@@H]2NC(=O)c1cccnc1]

R,R and S,R

N-[trans-(7RS,9RS)-9-amino-3-cyclopropyl-5-(2-methylpropylsulfamoyl)-8,9-dihydro-7H-cyclopenta[h]isoquinolin-7-yl]pyridine-3-carboxamide To a suspension of Example 1 (200 mg, 0.345 mmol) in DCM (2.5 mL) at 0° C. was added trifluoroacetic acid (2.5 mL, 45.0 mmol). The resulting solution was stirred at room temperature for 30 minutes. The solvent was removed from the reaction azeotroping with 1:1 DCM/heptane to remove the excess TFA. The resulting gum was purified by SCX column chromatography eluting with 0 to 100% of 7 M $NH_3$ in methanol gradient to afford the title compound as a mixture of enantiomers (165 mg, quantitative); $\delta_H$ (500 MHz, Methanol-d4) 9.50 (s, 1H), 9.04 (dd, J=2.2, 0.8 Hz, 1H), 8.70 (dd, J=4.9, 1.6 Hz, 1H), 8.41 (d, J=0.7 Hz, 1H), 8.35-8.25 (m, 2H), 7.56 (ddd, J=8.0, 4.9, 0.8 Hz, 1H), 6.13 (t, J=7.7 Hz, 1H), 5.23 (d, J=6.0 Hz, 1H), 3.38-3.31 (m, 1H), 2.73-2.54 (m, 4H), 2.31 (ddd, J=13.5, 8.1, 5.0 Hz, 1H), 1.62 (dp, J=13.5, 6.7 Hz, 1H), 1.12 (ddtd, J=15.9, 8.0, 5.3, 1.8 Hz, 4H), 0.77 (dd, J=9.7, 6.7 Hz, 6H). LCMS $[M+H]^+$ 480, RT 1.55 minutes (Method 2).

Example 4

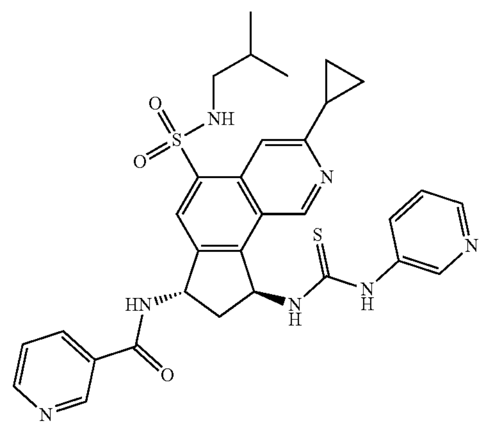

R,R and S,S

N-[trans-(7RS,9RS)-3-cyclopropyl-5-(2-methylpropylsulfamoyl)-9-(pyridin-3-ylcarbamothioylamino)-8,9-dihydro-7H-cyclopenta[h]isoquinolin-7-yl]pyridine-3-carboxamide To a solution of Example 3 (50 mg, 0.104 mmol) in THF (1 mL) was added 3-isothiocyanatopyridine (0.013 mL, 0.115 mmol). The solution was stirred for 10 minutes. The solid from the reaction mixture was filtered, washed with DCM (1 mL) and dried under vacuum to give the title compound as a mixture of enantiomers (32 mg, 49% yield). A second crop of the title compound was obtained from the filtrate (16 mg, 25% yield); $^{1}$H NMR (500 MHz, Methanol-d4) $\delta_H$ 9.51 (s, 1H), 9.05 (d, J=1.6 Hz, 1H), 8.71 (dd, J=4.9, 1.6 Hz, 1H), 8.58 (d, J=2.4 Hz, 1H), 8.43 (s, 1H), 8.37-8.24 (m, 3H), 8.03 (ddd, J=8.3, 2.5, 1.5 Hz, 1H), 7.61-7.49 (m, 1H), 7.39 (dd, J=8.2, 4.9 Hz, 1H), 7.07-6.98 (m, 1H), 6.08 (t, J=7.3 Hz, 1H), 2.83-2.74 (m, 2H), 2.66 (qd, J=12.9, 6.9 Hz, 2H), 2.31 (ddd, J=13.4, 7.9, 5.1 Hz, 1H), 1.63 (dp, J=13.5, 6.8 Hz, 1H), 1.18-1.03 (m, 4H), 0.77 (t, J=6.7 Hz, 6H). LCMS [M+H]$^+$ 616, RT 2.90 minutes (Method 3).

Example 5

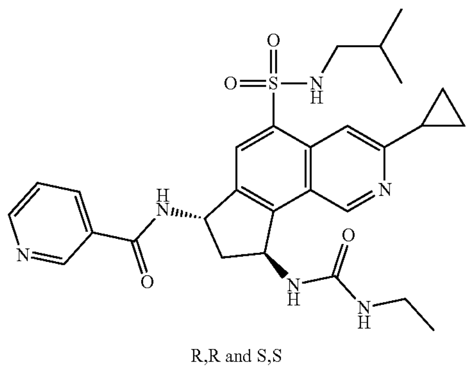 [SMILES: CCNC(=O)N[C@H]1C[C@H](NC(=O)c2cccnc2)c2cc(S(=O)(=O)NCC(C)C)c3cc(C4CC4)ncc3c21]

R,R and S,S

N-[trans-(7RS,9RS)-3-cyclopropyl-9-(ethylcarbamoylamino)-5-(2-methylpropylsulfamoyl)-8,9-dihydro-7H-cyclopenta[h]isoquinolin-7-yl]pyridine-3-carboxamide To a solution of Example 3 (20 mg, 0.0417 mmol) in THF (1 mL) was added isocyanatoethane (0.004 mL, 0.046 mmol). The solution was stirred for 18 hours. The solvent was removed to give a pale-yellow residue. The residue was purified by reverse phase HPLC (basic conditions) to afford the title compound as a mixture of enantiomers (18 mg, 76% yield); $\delta_H$ (500 MHz, Methanol-d4) 9.40 (d, J=0.7 Hz, 1H), 9.03 (dd, J=2.3, 0.8 Hz, 1H), 8.70 (dd, J=4.9, 1.6 Hz, 1H), 8.41 (d, J=0.8 Hz, 1H), 8.33-8.26 (m, 2H), 7.56 (ddd, J=8.0, 4.9, 0.8 Hz, 1H), 6.14-5.97 (m, 2H), 3.26-3.16 (m, 2H), 2.72-2.58 (m, 4H), 2.30 (ddd, J=13.3, 7.9, 5.2 Hz, 1H), 1.61 (dq, J=13.3, 6.6 Hz, 1H), 1.16-1.07 (m, 7H), 0.77 (t, J=6.6 Hz, 6H). LCMS [M+H]$^+$ 551, RT 2.69 minutes (Method 3).

Example 6

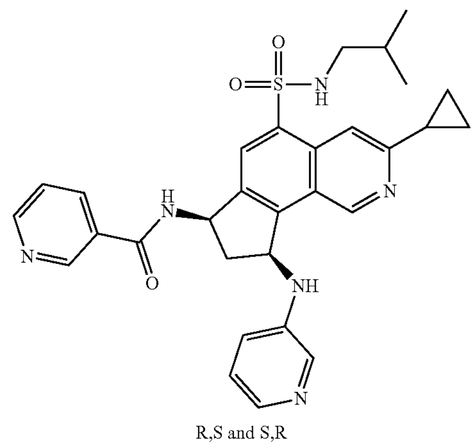 [SMILES: CC(C)CNS(=O)(=O)c1cc2c(c3cnc(C4CC4)cc13)[C@@H](Nc1cccnc1)C[C@H]2NC(=O)c1cccnc1]

R,S and S,R

N-[cis-(7RS,9SR)-3-cyclopropyl-5-(2-methylpropylsulfamoyl)-9-(pyridin-3-ylamino)-8,9-dihydro-7H-cyclopenta[h]isoquinolin-7-yl]pyridine-3-carboxamide In a pressure vial, to a solution of intermediate 35 (15 mg, 0.031 mmol) in 1,4-dioxane (1 mL) was added tBuXPhos Pd G3 (6.2 mg, 7.82 μmol), 3-bromopyridine (0.007 mL, 0.078 mmol) and sodium 2-methylpropan-2-olate (12 mg, 0.12 mmol). The solution was heated at 90° C. for 150 minutes. The solvent was removed to give a pale-yellow residue. The residue was purified by reverse phase HPLC (basic conditions) to afford the title compound as a mixture of enantiomers (8 mg, 46% yield); $^{1}$H NMR (500 MHz, Methanol-d4) $\delta_H$ 9.57 (s, 1H), 9.04 (d, J=1.7 Hz, 1H), 8.72 (dd, J=4.9, 1.5 Hz, 1H), 8.44 (d, J=0.7 Hz, 1H), 8.37 (s, 1H), 8.31 (dt, J=8.0, 1.9 Hz, 1H), 8.12 (s, 1H), 7.89 (d, J=4.0 Hz, 1H), 7.58 (ddd, J=8.0, 4.9, 0.7 Hz, 1H), 7.37-7.31 (m, 1H), 7.27 (dd, J=8.4, 4.7 Hz, 1H), 5.80-5.69 (m, 2H), 3.39 (dt, J=13.5, 8.0 Hz, 1H), 2.76-2.60 (m, 2H), 2.37-2.25 (m, 1H), 2.20 (dt, J=13.4, 6.1 Hz, 1H), 1.72-1.55 (m, 1H), 1.15-1.04 (m, 4H), 0.80 (dd, J=9.5, 6.7 Hz, 6H). LCMS [M+H]$^+$ 557, RT 3.01 minutes (Method 3).

Example 7

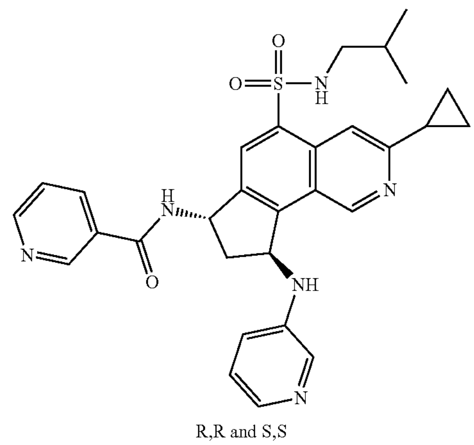 [SMILES: CC(C)CNS(=O)(=O)c1cc2c(c3cnc(C4CC4)cc13)[C@@H](Nc1cccnc1)C[C@@H]2NC(=O)c1cccnc1]

R,R and S,S

N-[trans-(7RS,9RS)-3-cyclopropyl-5-(2-methylpropylsulfamoyl)-9-(pyridin-3-ylamino)-8,9-dihydro-7H-cyclopenta[h]isoquinolin-7-yl]pyridine-3-carboxamide In a pressure vial, to a solution of Example 3 (7.0 mg, 0.014 mmol) in 1,4-dioxane (1 mL) was added tBuXPhos Pd G3 (2.9 mg, 3.65 μmol), 3-bromopyridine (0.003 mL, 0.036 mmol) and sodium 2-methylpropan-2-olate (5.6 mg, 0.0584 mmol). The solution was heated at 90° C. for 90 minutes. The solvent was removed to give a pale-yellow residue. The residue was purified by reverse phase HPLC (basic conditions) to afford the title compound as a mixture of enantiomers (5 mg, 60% yield); $\delta_H$ (500 MHz, Methanol-d4) 9.36-9.29 (m, 1H), 9.04 (d, J=1.6 Hz, 1H), 8.71 (dd, J=4.9, 1.6 Hz, 1H), 8.43 (d, J=0.8 Hz, 1H), 8.35 (s, 1H), 8.31 (dt, J=8.0, 1.9 Hz, 1H), 8.07 (s, 1H), 7.88 (t, J=2.91H z, 1H), 7.57 (ddd, J=8.0, 4.9, 0.8 Hz, 1H), 7.30-7.20 (m, 2H), 6.03 (t, J=7.4 Hz, 1H), 5.87 (d, J=5.1 Hz, 1H), 2.81-2.60 (m, 4H), 2.37-2.23 (m, 1H), 1.69-1.56 (m, 1H), 1.15-1.04 (m, 4H), 0.79 (t, J=6.7 Hz, 6H). LCMS [M+H]+ 557, RT 2.92 minutes (Method 3).

Examples 8 & 9

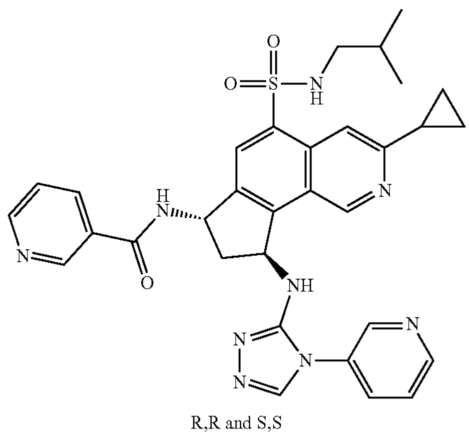

R,R and S,S

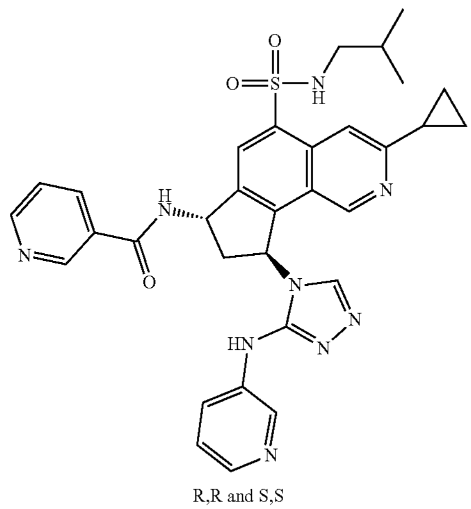

R,R and S,S

N-[trans-(7RS,9RS)-3-cyclopropyl-5-(2-methylpropylsulfamoyl)-9-[(4-pyridin-3-yl-1,2,4-triazol-3-yl)aminol-8,9-dihydro-7H-cyclopenta[h]isoquinolin-7-yl]pyridine-3-carboxamide (8)

N-[trans-(7RS,9 RS)-3-cyclopropyl-5-(2-methyl propylsulfamoyl)-9-[3-(pyridin-3-ylamino)-1,2,4-triazol-4-yl]-8,9-dihydro-7H-cyclopenta[h]isoquinolin-7-yl]pyridine-3-carboxamide (9)

To a solution of Intermediate 34 (43 mg, 0.07 mmol) in DMF (2 mL) was added formic hydrazide (13 mg, 0.21 mmol) and mercury dichloride (57 mg, 0.21 mmol). The mixture was stirred for 2 minutes then triethylamine (0.03 mL, 0.21 mmol) was added. The mixture was then heated at 90° C. for 1 hour. Acetonitrile (10 mL) and Celite (3 g) were added to the mixture, it was stirred for 5 minutes then filtered through Celite washing it with excess DCM and MeOH. The solvent of the filtrate was removed to give a brown oil. The oil was purified by reverse phase HPLC (basic conditions) to afford the title compounds as mixtures of enantiomers:

Example 8 (17 mg, 39% yield); $\delta_H$ (500 MHz, Methanol-d4) 9.46-9.39 (m, 1H), 9.04 (d, J=1.7 Hz, 1H), 8.74-8.62 (m, 2H), 8.59 (dd, J=4.9, 1.4 Hz, 1H), 8.41 (d, J=0.8 Hz, 1H), 8.36-8.24 (m, 3H), 7.94 (ddd, J=8.2, 2.5, 1.5 Hz, 1H), 7.62-7.50 (m, 2H), 6.11 (dd, J=7.4, 2.9 Hz, 1H), 6.03 (t, J=7.3 Hz, 1H), 2.87-2.71 (m, 2H), 2.70-2.55 (m, 2H), 2.35-2.25 (m, 1H), 1.69-1.56 (m, 1H), 1.18-1.05 (m, 4H), 0.83-0.70 (m, 6H). LCMS $[M+H]^+$ 624, RT 3.34 minutes (Method 5).

Example 9 (8 mg, 18% yield); $\delta_H$ (500 MHz, Methanol-d4) δ 9.03 (d, J=1.6 Hz, 1H), 8.90 (s, 1H), 8.71 (dd, J=4.9, 1.6 Hz, 1H), 8.60 (d, J=2.5 Hz, 1H), 8.46 (d, J=0.8 Hz, 1H), 8.39 (s, 1H), 8.31-8.25 (m, 1H), 8.16 (dd, J=4.8, 1.2 Hz, 1H), 7.97-7.87 (m, 2H), 7.57 (ddd, J=8.0, 4.9, 0.8 Hz, 1H), 7.37 (dd, J=8.4, 4.8 Hz, 1H), 6.70 (dd, J=8.2, 2.5 Hz, 1H), 6.12 (t, J=7.3 Hz, 1H), 3.08-2.92 (m, 2H), 2.78-2.62 (m, 2H), 2.33-2.23 (m, 1H), 1.71-1.55 (m, 1H), 1.16-1.03 (m, 4H), 0.84-0.71 (m, 6H). LCMS $[M+H]^+$ 624, RT 3.34 minutes (Method 5).

Example 10

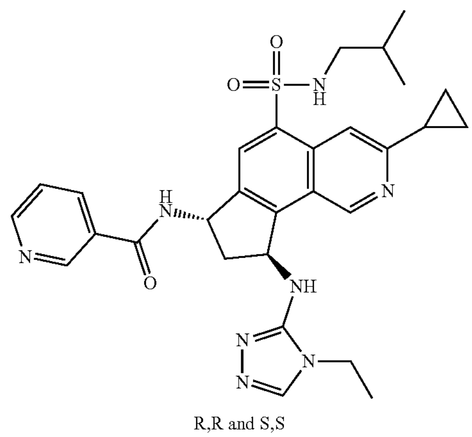 [SMILES: CCn1cnnc1N[C@H]1C[C@H](NC(=O)c2cccnc2)c2cc(S(=O)(=O)NCC(C)C)c3cc(C4CC4)ncc3c21]

R,R and S,S

N-[trans-(7RS,9RS)-3-cyclopropyl-9-[(4-ethyl-1,2,4-triazol-3-yl)aminol-5-(2-methylpropylsulfamoyl)-8,9-dihydro-7H-cyclopenta[h]isoquinolin-7-yl]pyridine-3-carboxamide To a solution of Intermediate 41 (55 mg, 0.097 mmol) in DMF (2.5 mL) was added formic hydrazide (17 mg, 0.29 mmol) and mercury dichloride (80 mg, 0.29 mmol). The mixture was stirred for 2 minutes then triethylamine (0.041 mL, 0.29 mmol) was added. The mixture was then heated at 90° C. for 30 minutes. Another portion of formic hydrazide (17 mg, 0.29 mmol) was added and the mixture was heated for a further hour. Acetonitrile (10 mL) and Celite (3 g) were added to the mixture, it was stirred for 5 minutes then filtered through Celite washing it with excess DCM and MeOH. The solvent of the filtrate was removed to give a brown oil. The oil was purified by flash column chromatography eluting with 0 to 10% of 7 M $NH_3$/MeOH in DCM gradient to afford the impure product as a brown solid. Further purification by reverse phase HPLC (Basic conditions) afforded the title compound as a mixture of enantiomers (20 mg, 35% yield). $\delta_H$ (500 MHz, Methanol-d4) 9.35 (s, 1H), 9.06 (d, J=1.6 Hz, 1H), 8.71 (dd, J=4.9, 1.6 Hz, 1H), 8.48-8.40 (m, 1H), 8.37-8.29 (m, 2H), 8.12 (s, 1H), 7.57 (ddd, J=8.0, 4.9, 0.7 Hz, 1H), 6.16-6.00 (m, 2H), 3.82 (p, J=7.3 Hz, 2H), 2.81-2.73 (m, 2H), 2.66 (qd, J=12.9, 6.9 Hz, 2H), 2.35-2.25 (m, 1H), 1.71-1.58 (m, 1H), 1.29 (t, J=7.3 Hz, 3H), 1.15-1.04 (m, 4H), 0.78 (dd, J=6.6, 5.4 Hz, 6H). LCMS [M+H]+ 575, RT 2.59 minutes (Method 3).

Example 11

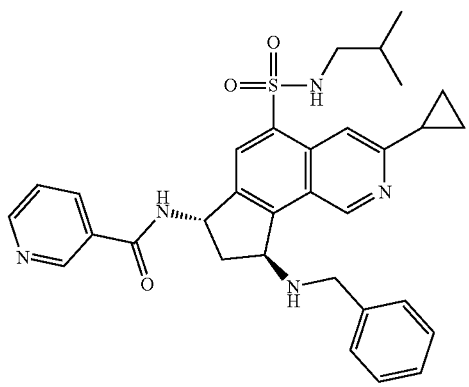

R,R and S,S

N-[trans-(7RS,9RS)-9-(benzylamino)-3-cyclopropyl-5-(2-methylpropylsulfamoyl)-8,9-dihydro-7H-cyclopenta[h]isoquinolin-7-yl]pyridine-3-carboxamide To a solution of Example 3 (15 mg, 0.031 mmol) in THF (1 mL) and DCM (1 mL) was added benzaldehyde (0.003 mL, 0.031 mmol). The solution was stirred for 5 hours. To the reaction was added sodium triacetoxyborohydride (20 mg, 0.094 mmol). The reaction was stirred for a further 18 hours. The solvent was removed to give a pale-yellow residue. The residue was purified by reverse phase HPLC (basic conditions) to afford the title compound as a mixture of enantiomers (11 mg, 62% yield). $\delta_H$ (500 MHz, Methanol-d4) 9.46-9.40 (m, 1H), 9.03 (dd, J=2.2, 0.7 Hz, 1H), 8.70 (dd, J=4.9, 1.6 Hz, 1H), 8.37 (d, J=0.8 Hz, 1H), 8.33-8.25 (m, 2H), 7.56 (ddd, J=8.0, 4.9, 0.8 Hz, 1H), 7.44 (d, J=7.1 Hz, 2H), 7.35 (t, J=7.6 Hz, 2H), 7.26 (t, J=7.3 Hz, 1H), 6.08 (t, J=7.5 Hz, 1H), 5.02 (d, J=6.0 Hz, 1H), 4.00-3.86 (m, 2H), 2.95-2.88 (m, 1H), 2.71-2.56 (m, 2H), 2.42 (dt, J=13.9, 7.3 Hz, 1H), 2.35-2.27 (m, 1H), 1.65-1.50 (m, 1H), 1.16-1.04 (m, 4H), 0.75 (dd, J=9.5, 6.7 Hz, 6H). LCMS [M+H]+ 570, RT 3.61 minutes (Method 3).

Example 12

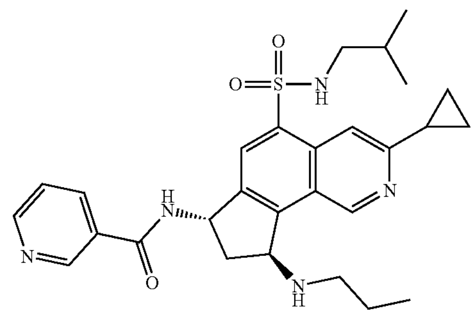

R,R and S,S

N-[trans-(7RS,9RS)-3-cyclopropyl-5-(2-methylpropylsulfamoyl)-9-(propylamino)-8,9-dihydro-7H-cyclopenta[h]isoquinolin-7-yl]pyridine-3-carboxamide To a solution of Example 3 (10 mg, 0.021 mmol) in THF (1 mL) and DCM (1 mL) was added propanal (0.002 mL, 0.031 mmol). The solution was stirred for 5 hours. Sodium triacetoxyborohydride (13 mg, 0.062 mmol) was added to the reaction and it was stirred for 2 hours. The solvent was removed to give a pale-yellow residue. The residue was purified by reverse phase HPLC (basic conditions) to afford the title compound as a mixture of enantiomers (11 mg, 95% yield). $\delta_H$ (500 MHz, Methanol-d4) 9.56 (s, 1H), 9.03 (dd, J=2.2, 0.7 Hz, 1H), 8.70 (dd, J=4.9, 1.6 Hz, 1H), 8.40 (d, J=0.7 Hz, 1H), 8.36-8.23 (m, 2H), 7.56 (ddd, J=8.0, 4.9, 0.8 Hz, 1H), 6.07 (t, J=7.6 Hz, 1H), 5.09 (d, J=6.3 Hz, 1H), 2.81 (ddd, J=13.6, 7.7, 1.9 Hz, 1H), 2.77-2.56 (m, 4H), 2.45 (dt, J=13.7, 7.4 Hz, 1H), 2.31 (ddd, J=13.2, 8.1, 5.1 Hz, 1H), 1.65-1.50 (m, 3H), 1.17-1.06 (m, 4H), 0.96 (t, J=7.4 Hz, 3H), 0.75 (dd, J=10.4, 6.7 Hz, 6H).

LCMS $[M+H]^+$ 522, RT 3.30 minutes (Method 4).

Example 13

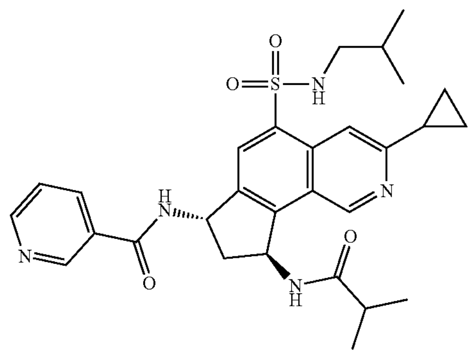

R,R and S,S

N-[trans-(7RS,9RS)-3-cyclopropyl-9-(2-methylpropanoylamino)-5-(2-methylpropylsulfamoyl)-8,9-dihydro-7H-cyclopenta[h]isoquinolin-7-yl]pyridine-3-carboxamide To a solution of Example 3 (20 mg, 0.042 mmol) in THF (1 mL) at 0° C. was added DIPEA (0.022 mL, 0.125 mmol) and 2-methylpropanoyl chloride (0.006 mL, 0.054 mmol). The solution was stirred at room temperature for 20 minutes. The solvent was removed to give a yellow gum. The gum was purified by reverse phase HPLC (basic conditions) to afford the title compound as a mixture of enantiomers (14 mg, 61% yield). $\delta_H$ (500 MHz, Methanol-d4) 9.27 (s, 1H), 9.04 (d, J=1.6 Hz, 1H), 8.75-8.67 (m, 1H), 8.41 (d, J=0.7 Hz, 1H), 8.35-8.27 (m, 2H), 7.57 (dd, J=7.7, 5.2 Hz, 1H), 6.21 (dd, J=8.0, 2.5 Hz, 1H), 6.10 (t, J=7.5 Hz, 1H), 2.74-2.57 (m, 4H), 2.42 (p, J=6.9 Hz, 1H), 2.30 (tt, J=7.8, 5.4 Hz, 1H), 1.62 (dp, J=13.5, 6.8 Hz, 1H), 1.20-1.05 (m, 10H), 0.77 (t, J=6.8 Hz, 6H). LCMS $[M+H]^+$ 550, RT 2.95 minutes (Method 3).

Examples 14 & 15

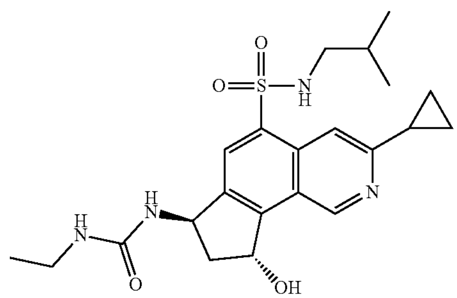

R,R and S,S

-continued

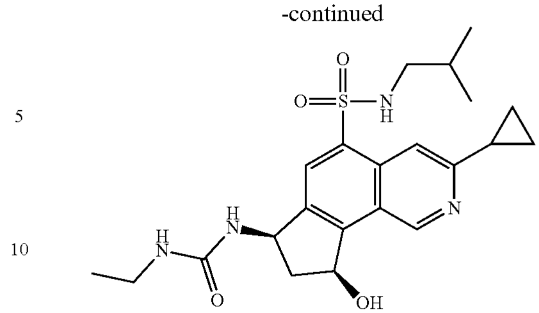

R,S and S,R 1-ethyl-3-[trans-(7RS,9RS)-3-cyclopropyl-9-hydroxy-5-(2-methylpropylsulfamoyl)-8,9-dihydro-7H-cyclopenta[h]isoquinolin-7-yl]urea (14)

1-ethyl-3-[cis-(7RS,9SR)-3-cyclopropyl-9-hydroxy-5-(2-methylpropylsulfamoyl)-8,9-dihydro-7H-cyclopenta[h]isoquinolin-7-yl]urea (15)

A solution of Intermediate 39 (23 mg, 0.061 mmol) and ethyl isocyanate (30 μL, 0.38 mmol) in dichloromethane (1 mL) was stirred at room temp overnight. The reaction was quenched with methanol and concentrated in vacuo to give a brown oil (28 mg) as a mixture of cis and trans diastereoisomers. The residue was purified by column chromatography to yield the title compounds as mixture of enantiomers:

Example 14, trans, (1.9 mg, 7%): LCMS $[M+H]^+$ 447, RT 1.68 min (Method 9).

Example 15, cis, (2.2 mg, 8%): LCMS $[M+H]^+$ 447, RT 1.71 min (Method 9). $^1$H NMR (300 MHz, DMSO-d6) $\delta_H$ 9.68 (s, 1H), 8.36 (s, 1H), 8.09 (s, 1H), 6.41 (d, J=8.5 Hz, 1H), 5.95 (d, J=5.5 Hz, 1H), 5.54 (s, 1H), 5.09 (d, J=8.1 Hz, 1H), 3.17-3.01 (m, 2H), 2.91 (m, 1H), 2.53 (m, 2H), 2.32 (m, 1H), 1.76 (m, 1H), 1.55 (m, 1H), 1.03 (t, J=7.2 Hz, 7H), 0.76 (d, J=3.5 Hz, 3H), 0.74 (d, J=3.6 Hz, 3H).

Example 16

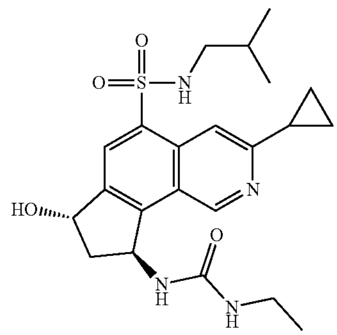

R,R and S,S 1-ethyl-3-[trans-(7RS,9RS)-3-cyclopropyl-7-hydroxy-5-(2-methylpropylsulfamoyl)-8,9-dihydro-7H-cyclopenta[h]isoquinolin-9-yl]urea A solution of Intermediate 37 (30 mg, 0.08 mmol) and ethyl isocyanate (19 μL, 0.24 mmol) in dichloromethane (1 mL) was stirred at room temp overnight (a few drops of DMF were added to aid solubility). The reaction was quenched with methanol and concentrated in vacuo to give a brown oil as a ~2:1 mixture of trans and cis isomers which were separated by column chromatography to give the title compound (5 mg, 14%) as a mixture of enantiomers. $^{1}H$ NMR (300 MHz, DMSO-d6) $\delta_H$ 9.34 (s, 1H), 8.40 (s, 1H), 8.23 (s, 1H), 8.10 (br, 1H), 6.49 (d, J=8.9 Hz, 1H), 5.89-5.75 (m, 1H), 5.69 (t, J=5.6 Hz, 1H), 5.60 (br, 1H), 5.39 (t, J=6.2 Hz, 1H), 3.12-2.92 (m, 2H), 2.54 (d, J=7.0 Hz, 2H), 2.28 (ddd, J=12.6, 6.8, 3.7 Hz, 3H), 1.59 (dt, J=13.2, 6.6 Hz, 1H), 1.10-0.88 (m, 7H), 0.76 (dd, J=6.6, 1.0 Hz, 6H). LCMS $[M+H]^+$ 447.4 with retention time 1.95 min (Method 16).

Example 17

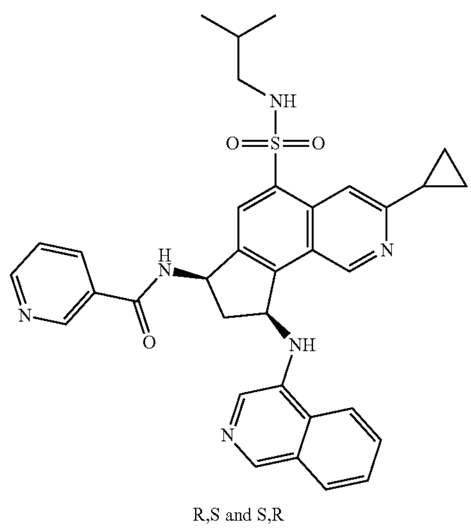 [SMILES: CC(C)CNS(=O)(=O)c1cc2c(c3cnc(C4CC4)cc13)[C@@H](Nc1cncc3ccccc13)C[C@H]2NC(=O)c1cccnc1]

R,S and S,R

N-[cis-(7RS,9SR)-3-cyclopropyl-9-(isoquinolin-4-ylamino)-5-(2-methylpropylsulfamoyl)-8,9-dihydro-7H-cyclopenta[h]isoquinolin-7-yl]pyridine-3-carboxamide To a mixture of sodium tert-butoxide (20 mg, 0.2081 mmol), methanesulfonato(2-di-t-butylphosphino-2',4',6'-tri-i-propyl-1,1'-biphenyl)(2'-amino-1,1'-biphenyl-2-yl)palladium(II) (3.3 mg, 0.004 mmol), 2-di-tert-butylphosphino-2',4',6'-triisopropylbiphenyl (1.8 mg, 0.004 mmol), 4-bromoisoquinoline (12.5 mg, 0.06 mmol) and intermediate 35 (18 mg, 0.03753 mmol), 1,4-dioxane (0.20 mL) was added. The reaction mixture was then heated at 90° C. for 2 hours. Purification by column chromatography (basic conditions) gave the title compound as a mixture of enantiomers (9.8 mg). LCMS (ES+) m/z=607 $(M+H)^+$ RT=2.55 (Method 6).

Examples 18-29

Examples 18-29 were made according the following procedure using the following stock solutions:

Intermediate 23 (130 mg) dissolved in a mixture of DCM (6 mL) and DMA (500 μL)

Intermediate 33 (130 mg) dissolved in DCM (6.5 mL)

Intermediate 31 (91 mg) dissolved in DCM (6.5 mL)

The relevant isocyanate (1.3 equivalents, see table) was added to the relevant amine stock solution (500 L—intermediate 23, 31 or 33 above) and the reaction mixtures stirred at room temperature for 2 hours. The solvent was removed, and the residues purified by preparative LCMS in basic mode (with examples 19 & 24 undergoing an additional preparative purification under acidic conditions and desalinated by a third purification in basic conditions) to give the products in the table below as mixtures of enantiomers.

LCMS data in the table was obtained using LCMS method 18.

| Example | structure | IUPAC name | Iso-cyanate substrate | RT | Mass |
|---|---|---|---|---|---|
| 18 | 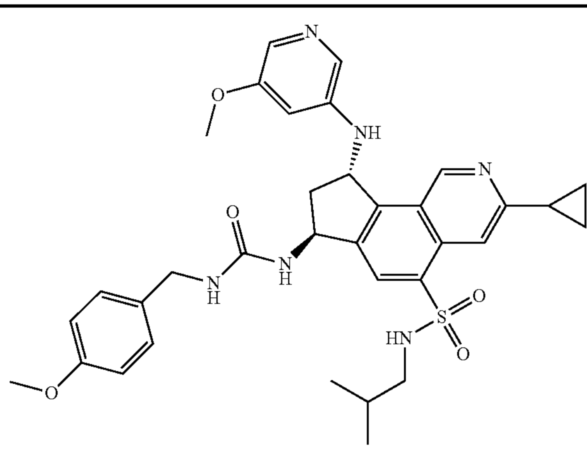 R,R and S,S | 1-[(4-methoxyphenyl)methyl]-3-[trans-(7R,9RS)-3-cyclopropyl-9-[(5-methoxypyridin-3-yl)amino]-5-(2-methylpropylsulfamoyl)-8,9-dihydro-7H-cyclopenta[h]isoquinolin-7-yl]urea | 4-methoxy-benzyl isocyanate | 2.12 | 645 |

-continued

| Example | structure | IUPAC name | Iso-cyanate substrate | RT | Mass |
|---|---|---|---|---|---|
| 19 | 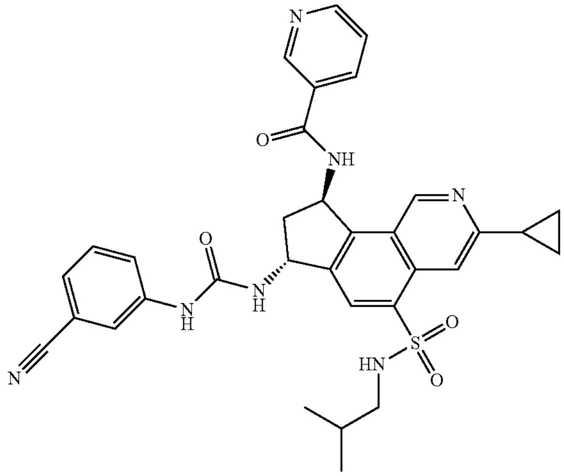 R,R and S,S | N-[trans-(7RS,9RS)-7-[(3-cyanophenyl)carbamoylamino]-3-cyclopropyl-5-(2-methylpropylsulfamoyl)-8,9-dihydro-7H-cyclopenta[h]isoquinolin-9-yl]pyridine-3-carboxamide | 3-cyanophenyl isocyanate | 2.31 | 624 |
| 20 | 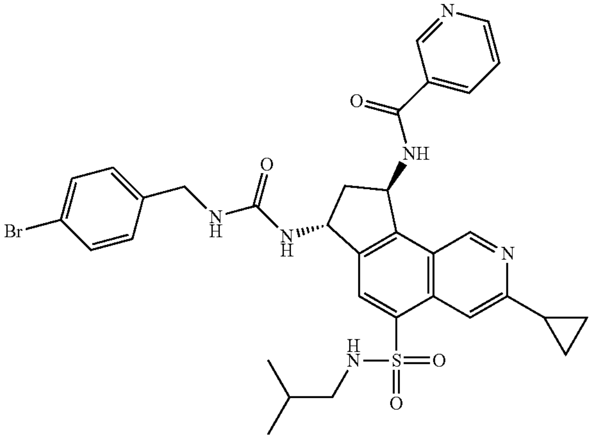 R,R and S,S | N-[trans-(7RS,9RS)-7-[(4-bromophenyl)methylcarbamoylamino]-3-cyclopropyl-5-(2-methylpropylsulfamoyl)-8,9-dihydro-7H-cyclopenta[h]isoquinolin-9-yl]pyridine-3-carboxamide | 4-bromobenzyl isocyanate | 2.48 | 691 |
| 21 | 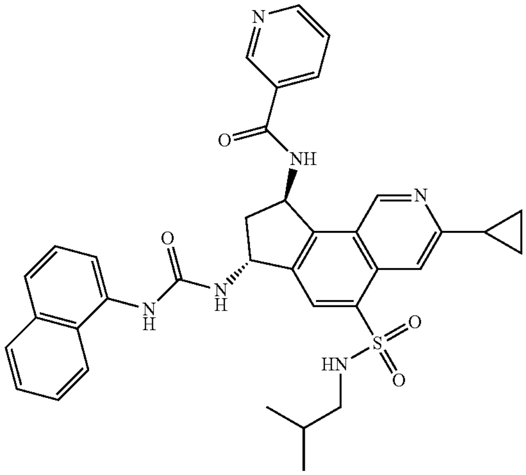 R,R and S,S | N-[trans-(7RS,9RS)-3-cyclopropyl-5-(2-methylpropylsulfamoyl)-7-(naphthalen-1-ylcarbamoyl)amino)-8,9-dihydro-7H-cyclopenta[h]isoquinolin-9-yl]pyridin-3-carboxamide | 1-naphthyl isocyanate | 2.48 | 649 |

-continued

| Example | structure | IUPAC name | Iso-cyanate substrate | RT | Mass |
|---|---|---|---|---|---|
| 22 | 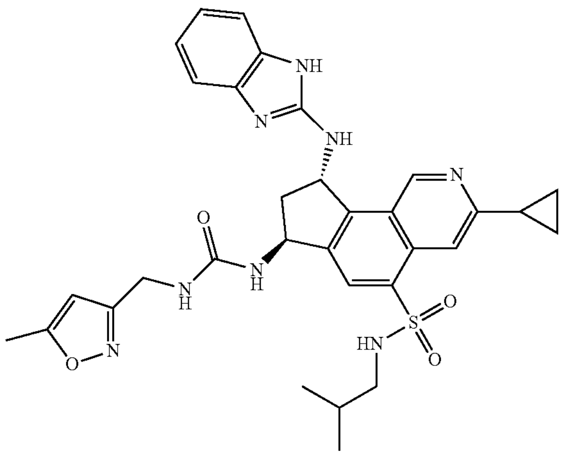 R,R and S,S | 1-[(5-methyl-1,2-oxazol-3-yl)methyl]-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea | 3-(isocyanato-methyl)-5-methyl-1,2-oxazole | 1.95 | 629 |
| 23 | 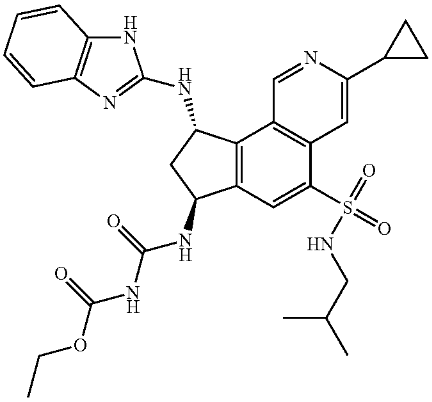 R,R and S,S | Ethyl N-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]carbamoyl]carbamate | ethoxy-carbonyl isocyanate | 2.06 | 606 |
| 24 | 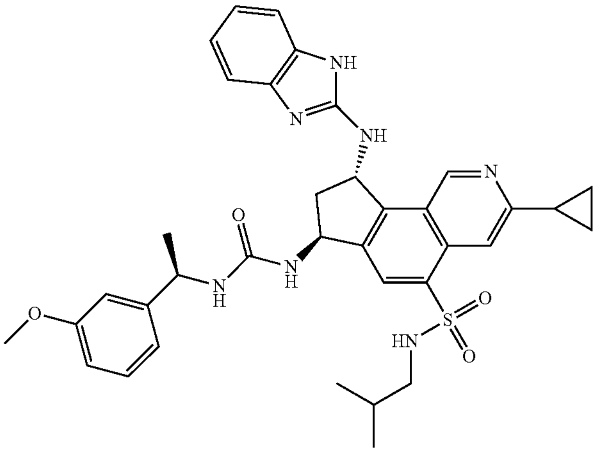 R,R and S,S | 1-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-yl]-3-[rac-(1S)-1-(3-methoxyphenyl)ethyl]urea | (r)-(+)-1-(3-methoxyphen-yl)ethyl isocyanate | 2.2 | 668 |

-continued

| Example | structure | IUPAC name | Iso-cyanate substrate | RT | Mass |
|---|---|---|---|---|---|
| 25 | 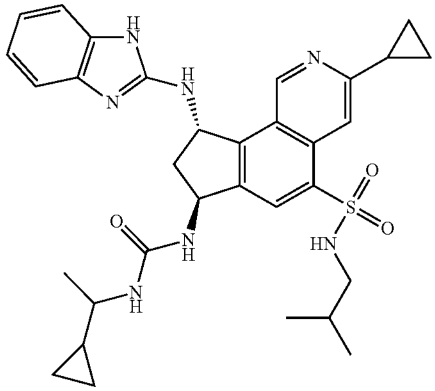 R,R and S,S | 1-(1-cyclopropylethyl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea | (1-isocyanato-ethyl)cyclo-propane | 2.11 | 602 |
| 26 | 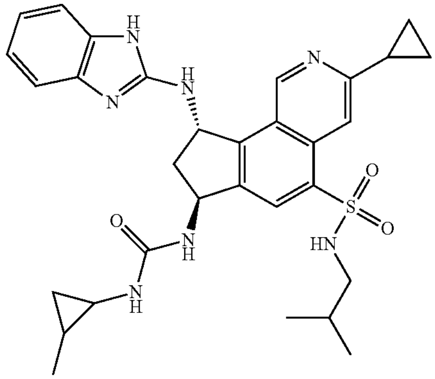 R,R and S,S | 1-(2-methylcyclopropyl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea | 1-isocyanato-2-methylcyclo-propane | 2.04 | 588 |
| 27 | 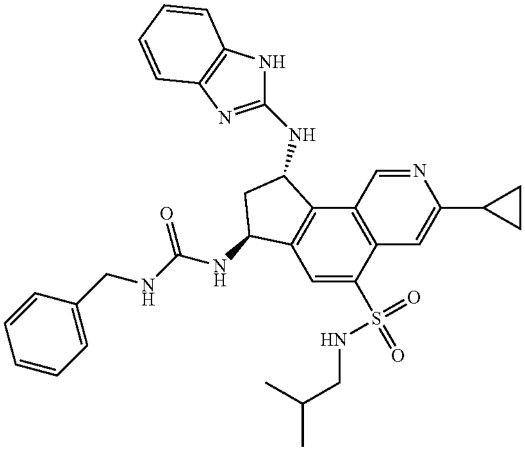 R,R and S,S | 1-benzyl-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea | benzyl isocyanate | 2.15 | 624 |

-continued

| Example | structure | IUPAC name | Iso-cyanate substrate | RT | Mass |
|---|---|---|---|---|---|
| 28 | 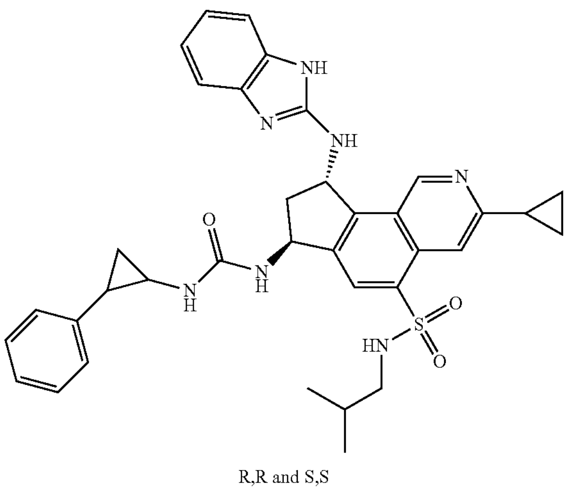 [SMILES: CC(C)CNS(=O)(=O)c1cc2c(c3cnc(C4CC4)cc13)[C@@H](Nc1nc3ccccc3[nH]1)C[C@@H]2NC(=O)NC1CC1c1ccccc1] R,R and S,S | 1-(2-phenylcyclopropyl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl)urea | (2-isocyanato-cyclopropyl) benzene | 2.24 | 650 |
| 29 | 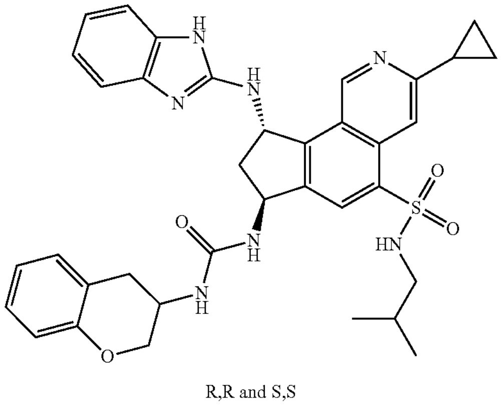 [SMILES: CC(C)CNS(=O)(=O)c1cc2c(c3cnc(C4CC4)cc13)[C@@H](Nc1nc3ccccc3[nH]1)C[C@@H]2NC(=O)NC1COc2ccccc2C1] R,R and S,S | 1-(3,4-dihydro-2H-chromen-3-yl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea | 3-isocyanato-3,4-dihydro-2h-1-benzopyran | 2.22 | 666 |

Examples 30-35

Examples 30-35 were made according the following procedure using the following stock solutions:

Intermediate 23 (100 mg) dissolved in a mixture of DCM (4.5 mL) and DMF (500 μL)

Intermediate 31 (70 mg) dissolved in DCM (5 mL)

The relevant acyl chloride (1.4 equivalents, see table*) was added to the relevant amine stock solution (500 μL—intermediate 23 or 31 above) and the reaction mixtures stirred at room temperature overnight. The solvent was removed, and the residues purified by preparative LCMS in basic mode (with example 34 undergoing an additional preparative purification under acidic conditions and desalinated by a third purification in basic conditions) to give the products in the table below as mixtures of enantiomers.

*In the case of example 31 the acid (1.4 equivalent) followed by DIPEA (15 μL), TBTU (10 mg) and DMF 500 μL) were added to the amine stock solution C (500 μL, intermediate 31).

LCMS data in the table was obtained using LCMS method 18.

| Example | Structure | Name | Substrate | RT | Mass |
|---|---|---|---|---|---|
| 30 | 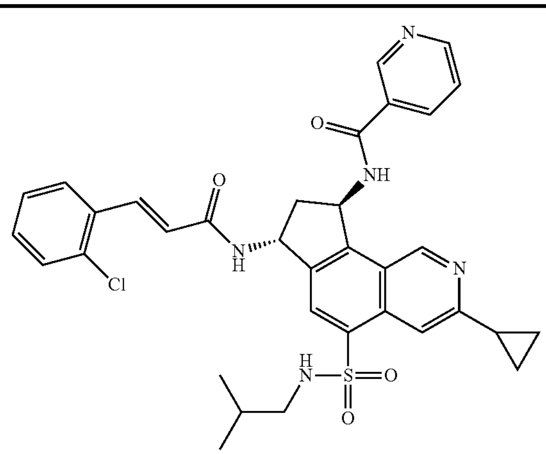 R,R and S,S | N-[trans-(7RS,9RS)-3-cyclopropyl-5-(2-methylpropylsulfamoyl)-7-[[rac-(E)-3-(2-chlorophenyl)prop-2-enoyl]amino]-8,9-dihydro-7H-cyclopenta[h]isoquinolin-9-yl]pyridine-3-carboxamide | 2-chlorocinnamoyl chloride | 2.57 | 644 |
| 31 | 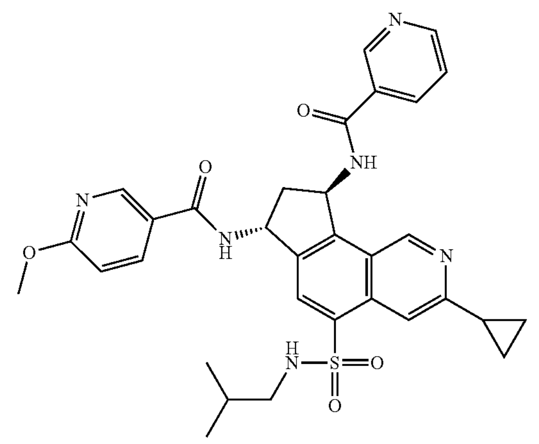 R,R and S,S | 6-methoxy-N-[trans-(7RS,9RS)-3-cyclopropyl-5-(2-methylpropylsulfamoyl)-9-(pyridine-3-carbonylamino)-8,9-dihydro-7H-cyclopenta[h]isoquinolin-7-yl]pyridine-3-carboxamide | 6-methoxypyridine-3-carboxylic acid | 2.23 | 615 |
| 32 | 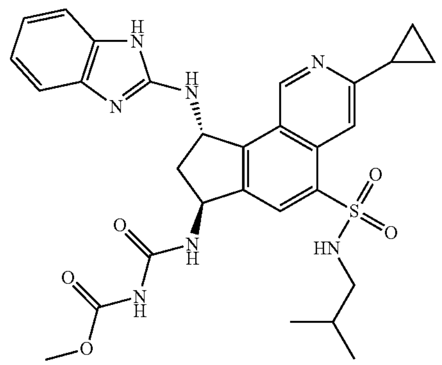 R,R and S,S | methyl 3-oxo-3-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]amino]propanoate | methyl malonyl chloride | 1.91 | 591 |

-continued

| Example | Structure | Name | Substrate | RT | Mass |
|---|---|---|---|---|---|
| 33 | 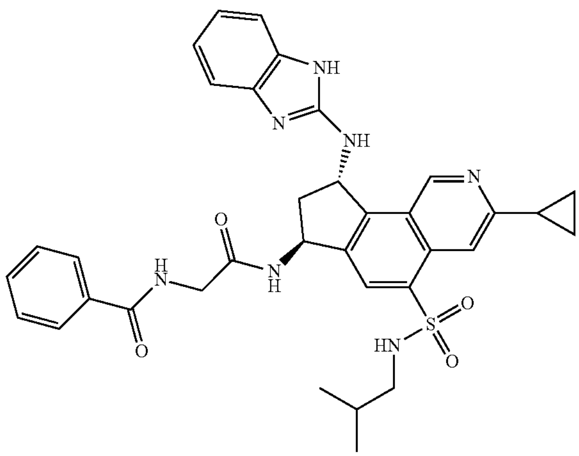 R,R and S,S | N-[2-oxo-2-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]amino]ethyl]benzamide | 2-(phenylformamido)acetyl chloride | 2.03 | 652 |
| 34 | 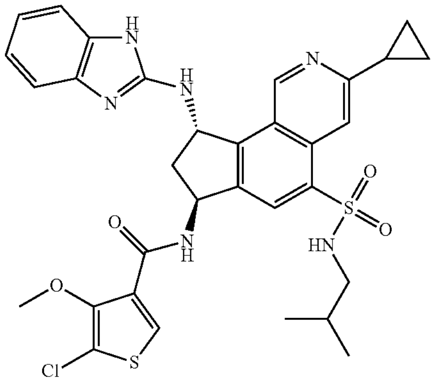 R,R and S,S | 5-chloro-4-methoxy-N-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]thiophene-3-carboxamide | 5-chloro-4-methoxythiophene-3-carbonyl chloride | 2.31 | 665 |
| 35 | 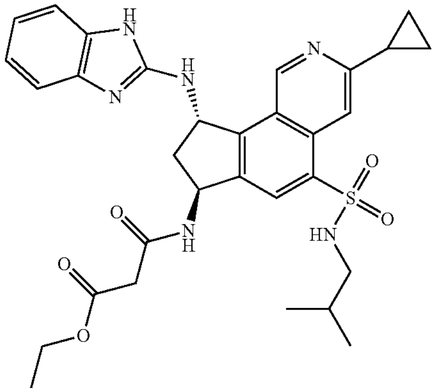 R,R and S,S | ethyl 3-oxo-3-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]amino]propanoate | ethyl malonyl chloride | 1.99 | 605 |

Examples 36-37

Examples 36-37 were made according the following procedure:

The relevant acyl chloride (1.1 equivalents, see table below) was added to Intermediate 25 (7 mg, 0.014 mmol) in a mixture of DCM (500 mL) and N,N-diisopropylethylamine (5 μL, 0.029 mmol). The reaction mixtures were stirred at room temperature for 1 hour then purified by basic preparative LCMS to give the products in the table below as mixtures of enantiomers.

LCMS data in the table was obtained using LCMS method 18.

| Example | Structure | Name | Substrate | RT | Mass |
|---|---|---|---|---|---|
| 36 | 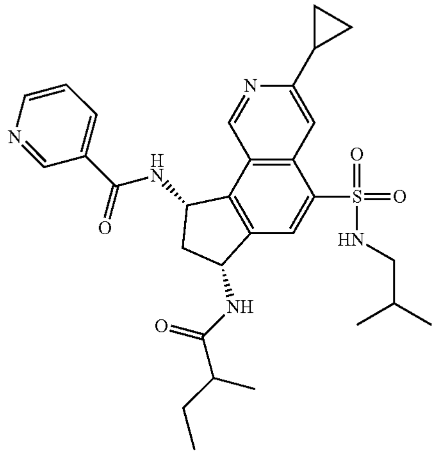 R,S and S,R | N-[cis-(7RS,9SR)-3-cyclopropyl-7-(2-methylbutanoylamino)-5-(2-methylpropylsulfamoyl)-8,9-dihydro-7H-cyclopenta[h]isoquinolin-9-yl]pyridine-3-carboxamide | dl-2-methylbutyryl chloride | 2.34 | 564 |
| 37 | 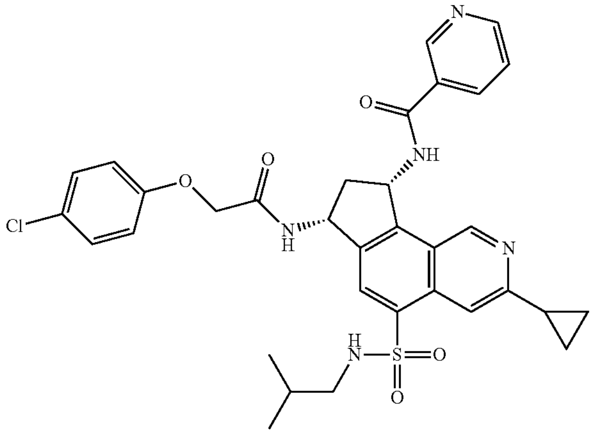 R,S and S,R | N-[cis-(7RS,9SR)-7-[[2-(4-chlorophenoxy)acetyl]amino]-3-cyclopropyl-5-(2-methylpropylsulfamoyl)-8,9-dihydro-7H-cyclopenta[h]isoquinolin-9-yl]pyridine-3-carboxamide | 4-chlorophenoxyacetyl chloride | 2.59 | 648 |

Examples 38-47

Examples 38-47 were made according the following procedure using the following stock solutions:

a) Example 3 (9.6 mg, 0.020 mmol) in DMF (1800 μL)

b) TBTU (7.5 mg, 0.023 mmol) in DMF (1800 μL)

c) N,N-diisopropylethylamine (20 (L, 0.115 mmol) in DMF (1800 μL)

200 L of each stock solution (a, b and c) were combined and added to the relevant substrate (see table below). The reaction mixture was stirred at room temperature overnight, then purified by basic preparative LCMS.

LCMS data in the table was obtained using LCMS method 18.

| Example | Structure | Name | Substrate | RT | Mass |
|---|---|---|---|---|---|
| 38 | 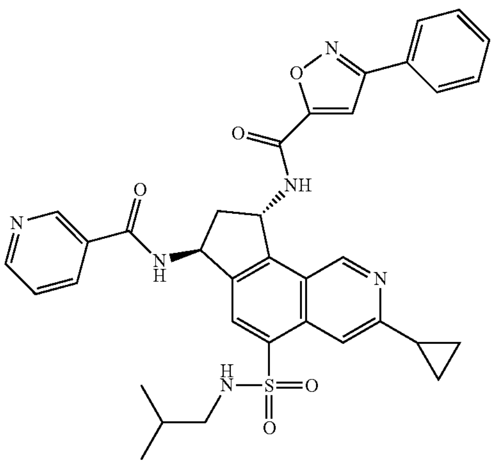 R,R and S,S | 3-phenyl-N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]-1,2-oxazole-5-carboxamide | 3-phenylisoxazole-5-carboxylic acid | 2.26 | 651 |
| 39 | 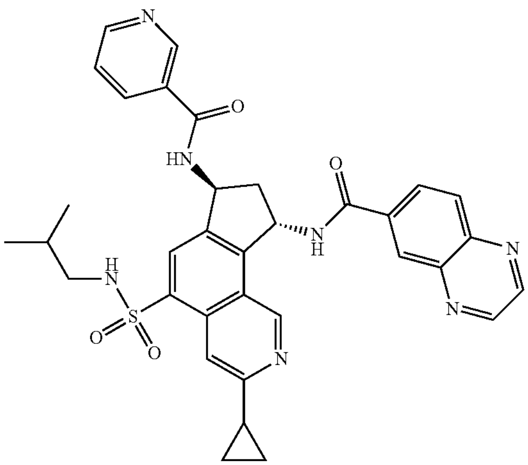 R,R and S,S | N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]quinoxaline-6-carboxamide | quinoxaline-6-carboxylic acid | 1.85 | 636 |
| 40 | 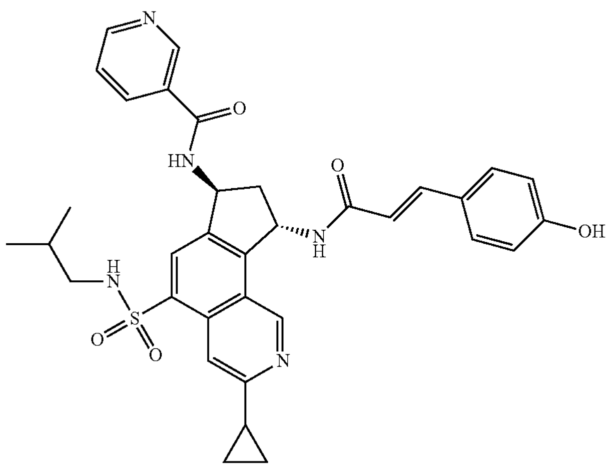 R,R and S,S | N-[trans-(7RS,9RS)-3-cyclopropyl-5-(2-methylpropylsulfamoyl)-9-[[rac-(E)-3-(4-hydroxyphenyl)prop-2-enoyl]amino]-8,9-dihydro-7H-cyclopenta[h]isoquinolin-7-yl]pyridine-3-carboxamide | 4-hydroxy-cinnamic acid | 1.88 | 626 |

-continued

| Example | Structure | Name | Substrate | RT | Mass |
|---|---|---|---|---|---|
| 41 | 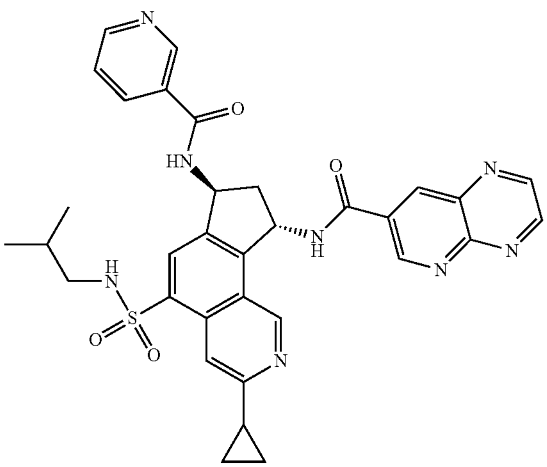 R,R and S,S | N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]pyrido[2,3-b]pyrazine-7-carboxamide | pyrido[2,3-b]pyrazine-7-carboxylic acid | 1.72 | 637 |
| 42 | 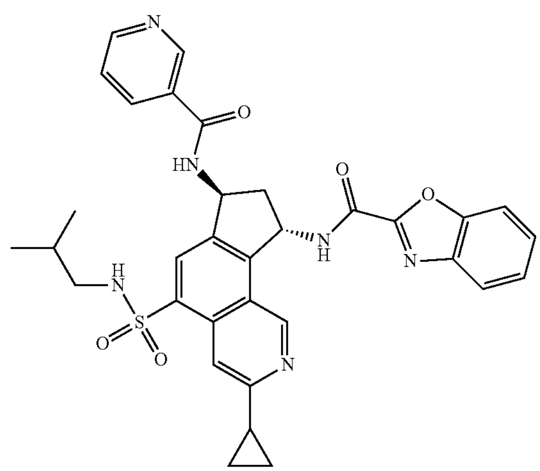 R,R and S,S | N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]-1,3-benzoxazole-2-carboxamide | benzooxazole-2-carboxylic acid | 2.08 | 625 |
| 43 | 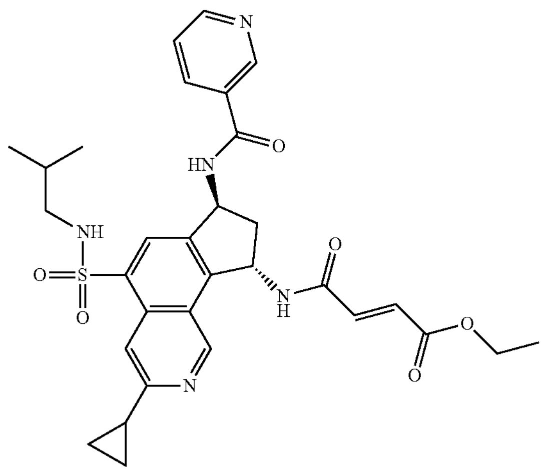 R,R and S,S | ethyl rac-(E)-4-oxo-4-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]amino]but-2-enoate | fumaric acid monoethyl ester | 1.98 | 606 |

-continued

| Example | Structure | Name | Substrate | RT | Mass |
|---|---|---|---|---|---|
| 44 | 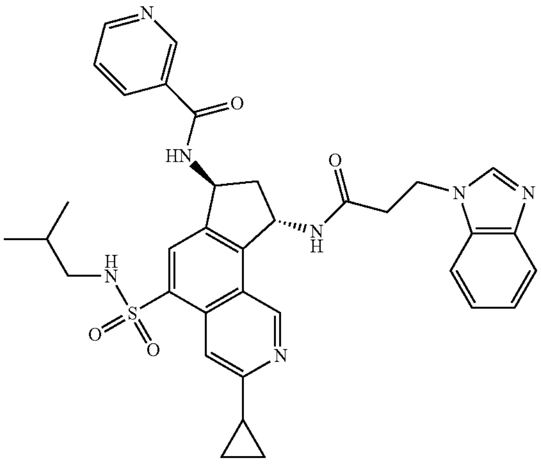 R,R and S,S | N-[trans-(7RS,9RS)-9-[3-(benzimidazol-1-yl)propanoylamino]-3-cyclopropyl-5-(2-methylpropylsulfamoyl)-8,9-dihydro-7H-cyclopenta[h]isoquinolin-7-yl]pyridine-3-carboxamide | 3-benzimi-dazol-1-yl-propionic acid | 1.56 | 652 |
| 45 | 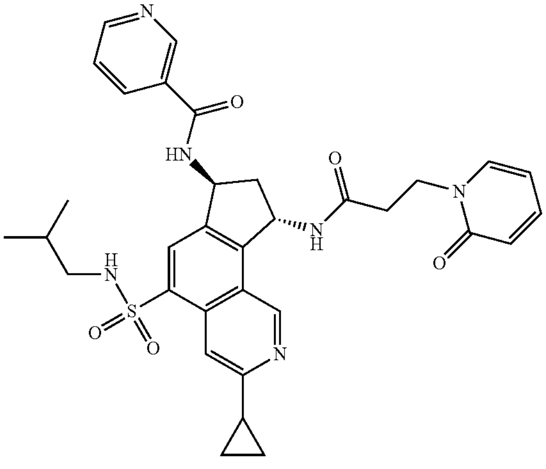 R,R and S,S | N-[trans-(7RS,9RS)-3-cyclopropyl-5-(2-methylpropylsulfamoyl)-9-[3-(2-oxopyridin-1-yl)propanoylamino]-8,9-dihydro-7H-cyclopenta[h]isoquinolin-7-yl]pyridine-3-carboxamide | 2-oxo-1(2h)-pyridinepro-panoic acid | 1.67 | 629 |
| 46 | 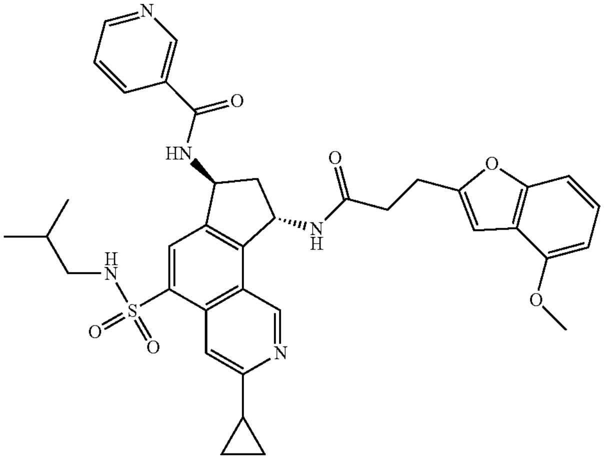 R,R and S,S | N-[trans-(7RS,9RS)-3-cyclopropyl-9-[(4-methoxy-1-benzofuran-2-carbonyl)amino]-5-(2-methylpropylsulfamoyl)-8,9-dihydro-7H-cyclopenta[h]isoquinolin-7-yl]pyridine-3-carboxamide | 2-benzofuran-carboxylic acid, 4-methoxy- | 2.2 | 654 |

-continued

| Example | Structure | Name | Substrate | RT | Mass |
|---|---|---|---|---|---|
| 47 | 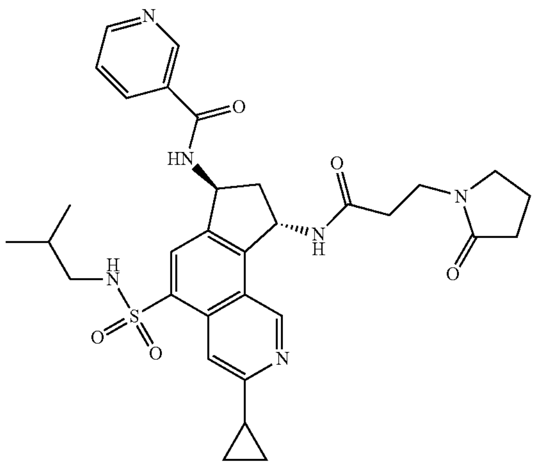 R,R and S,S | N-[trans-(7RS,9RS)-3-cyclopropyl-5-(2-methylpropylsulfamoyl)-9-[3-(2-oxopyrrolidin-1-yl)propanoylamino]-8,9-dihydro-7H-cyclopenta[h]isoquinolin-7-yl]pyridine-3-carboxamide | 3-(2-oxopyrrolidin-1-yl)propanoic acid | 1.66 | 619 |

Examples 48-52

Examples 48-52 were made according the following procedure:

A mixture of Example 3 (14 mg, 0.03 mmol), the relevant bromide (1.5 equivalents, see table below), methanesulfonato(2-di-t-butylphosphino-2',4',6'-tri-i-propyl-1,1'-biphenyl)(2'-amino-1,1'-biphenyl-2-yl)palladium(II) (2.4 mg, 0.003 mmol), 2-di-tert-butylphosphino-2',4',6'-triisopropylbiphenyl (1.3 mg, 0.003 mmol) and sodium tert-butoxide (15 mg, 0.15 mmol) was suspended in 1,4-dioxane (0.15 ml-) and heated at 90° C. for either 2 h or overnight. The reaction mixtures were cooled to room temperature and purified by basic preparative LCMS.

LCMS data in the table was obtained using LCMS method 18.

| Example | Structure | Name | Substrate | RT | Mass |
|---|---|---|---|---|---|
| 48 | 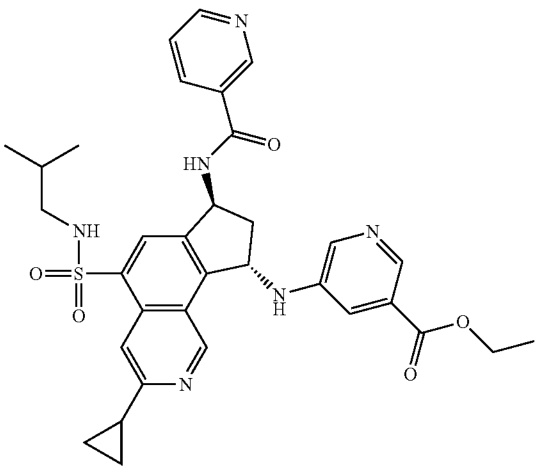 R,R and S,S | ethyl 5-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]amino]pyridine-3-carboxylate | ethyl 5-bromonicotinate | 2.22 | 629 |

-continued

| Example | Structure | Name | Substrate | RT | Mass |
|---|---|---|---|---|---|
| 49 | 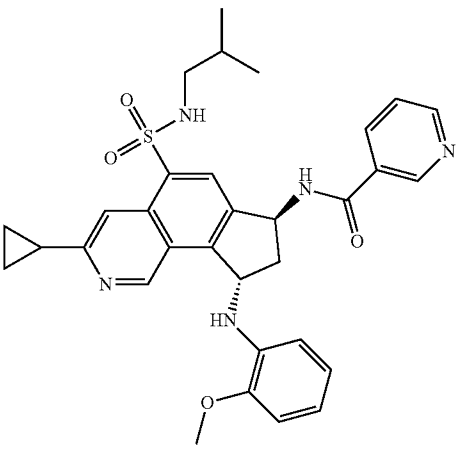 R,R and S,S | N-[trans-(7RS,9RS)-3-cyclopropyl-9-(2-methoxyanilino)-5-(2-methylpropylsulfamoyl)-8,9-dihydro-7H-cyclopenta[h]isoquinolin-7-yl]pyridine-3-carboxamide | 2-bromo-anisole | 2.65 | 586 |
| 50 | 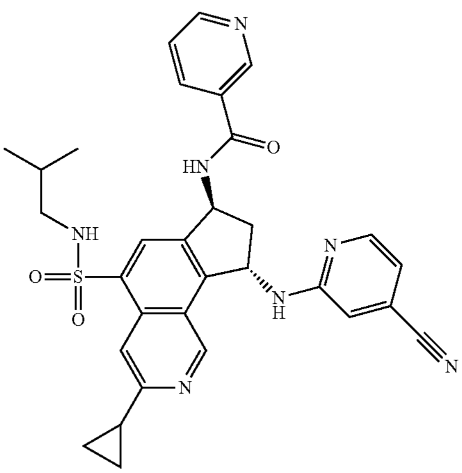 R,R and S,S | N-[trans-(7RS,9RS)-9-[(4-cyanopyridin-2-yl)amino]-3-cyclopropyl-5-(2-methylpropylsulfamoyl)-8,9-dihydro-7H-cyclopenta[h]isoquinolin-7-yl]pyridine-3-carboxamide | 2-bromo-4-cyanopyridine | 2.39 | 582 |
| 51 | 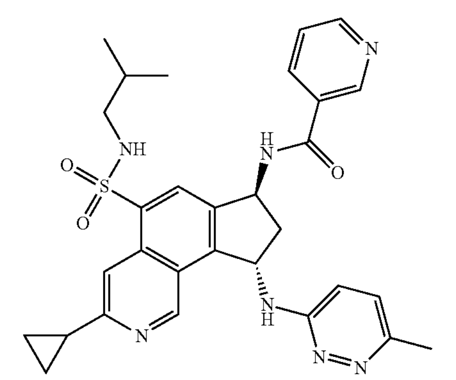 R,R and S,S | N-[trans-(7RS,9RS)-3-cyclopropyl-5-(2-methylpropylsulfamoyl)-9-[(6-methylpyridazin-3-yl)amino]-8,9-dihydro-7H-cyclopenta[h]isoquinolin-7-yl]pyridine-3-carboxamide | 3-bromo-6-methylpyridazine | 1.8 | 572 |

-continued

| Example | Structure | Name | Substrate | RT | Mass |
|---|---|---|---|---|---|
| 52 | 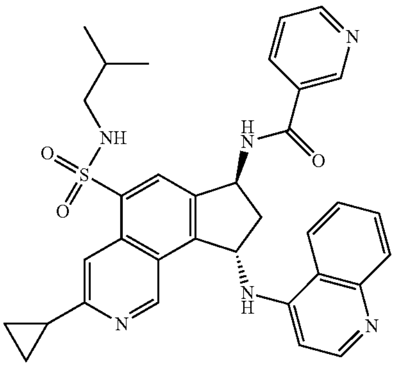 R,R and S,S | N-[trans-(7RS,9RS)-3-cyclopropyl-5-(2-methylpropylsulfamoyl)-9-(quinolin-4-ylamino)-8,9-dihydro-7H-cyclopenta[h]isoquinolin-7-yl]pyridine-3-carboxamide | 4-bromoiso-quinoline | 1.9 | 607 |

Examples 53-59

Examples 53-59 were made according the following procedure:

Example 3 (8.4 mg, 0.018 mmol) was added to a solution of the relevant isocyanate (1.3 equivalents, see table below) in DCM (0.5 m). N,N-diisopropylethylamine (15 µL, 0.086 mmol) was then added and the reaction mixture stirred at room temperature for 2 hours. The solvent was then removed, and the residue purified by basic preparative LCMS.

LCMS data in the table was obtained using LCMS method 18.

| Example | Structure | Name | Substrate | RT | Mass |
|---|---|---|---|---|---|
| 53 | 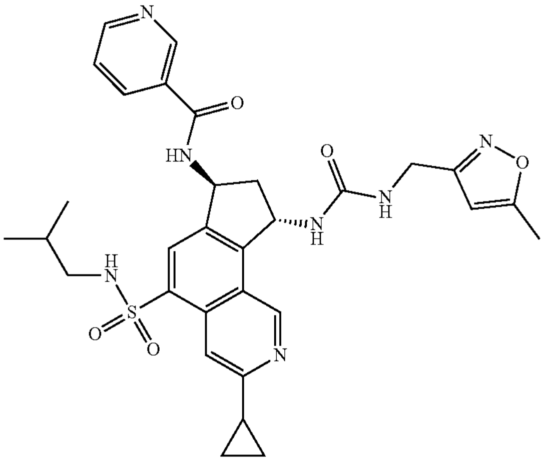 R,R and S,S | N-[trans-(7RS,9RS)-3-cyclopropyl-9-[(5-methyl-1,2-oxazol-3-yl)methylcarbamoylamino]-5-(2-methylpropylsulfamoyl)-8,9-dihydro-7H-cyclopenta[h]isoquinolin-7-yl]pyridine-3-carboxamide | 3-(isocyanato-methyl)-5-methyl-1,2-oxazole | 1.81 | 618 |

-continued

| Example | Structure | Name | Substrate | RT | Mass |
|---|---|---|---|---|---|
| 54 | 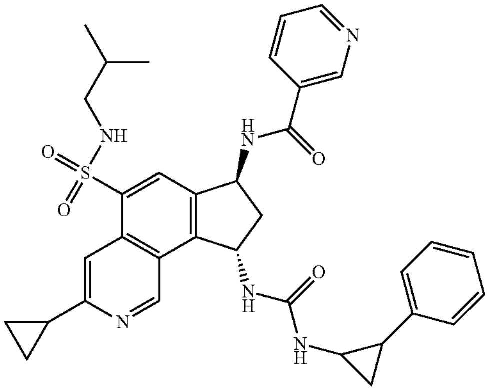 R,R and S,S | N-[trans-(7RS,9RS)-3-cyclopropyl-5-(2-methylpropylsulfamoyl)-9-[(2-phenylcyclopropyl)carbamoylamino]-8,9-dihydro-7H-cyclopenta[h]isoquinolin-7-yl]pyridine-3-carboxamide | (2-isocyanatocyclopropyl)benzene | 2.1 | 639 |
| 55 | 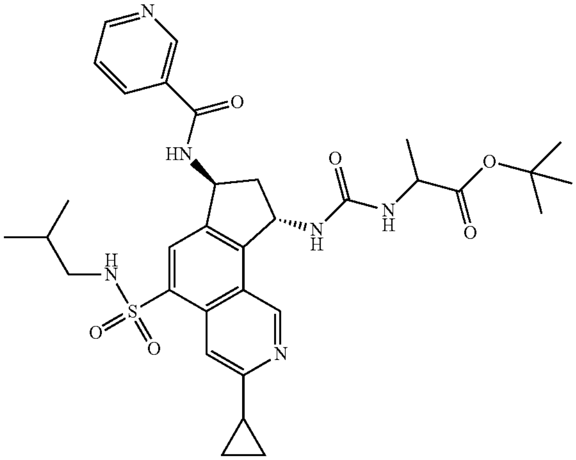 R,R and S,S | tert-butyl 2-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]carbamoylamino)propanoate | 2-isocyanato-propionic acid tert-butyl ester | 2.08 | 651 |
| 56 | 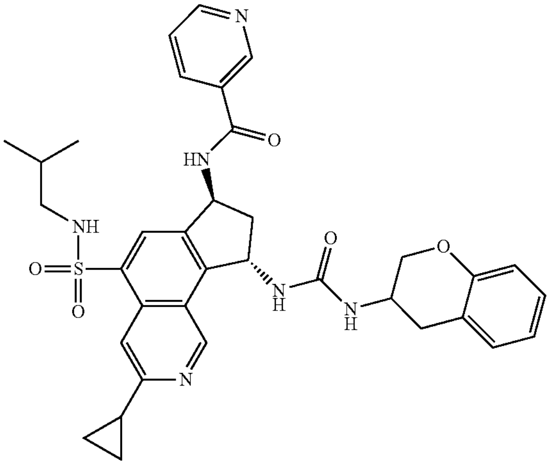 R,R and S,S | N-[trans-(7RS,9RS)-3-cyclopropyl-9-(3,4-dihydro-2H-chromen-3-ylcarbamoylamino)-5-(2-methylpropylsulfamoyl)-8,9-dihydro-7H-cyclopenta[h]isoquinolin-7-yl]pyridine-3-carboxamide | 3-isocyanato-3,4-dihydro-2h-1-benzopyran | 2.1 | 655 |

-continued

| Example | Structure | Name | Substrate | RT | Mass |
|---|---|---|---|---|---|
| 57 | 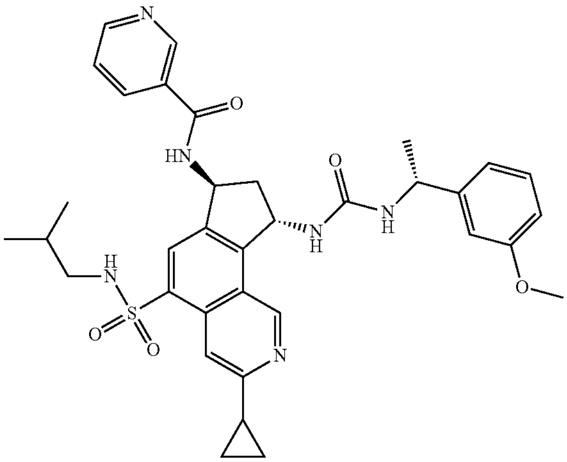 S,S and R,R | N-[trans-(7SR,9SR)-3-cyclopropyl-5-(2-methylpropylsulfamoyl)-9-[[rac-(1R)-1-(3-methoxyphenyl)ethyl]-carbamoylamino]-8,9-dihydro-7H-cyclopenta[h]isoquinolin-7-yl]pyridine-3-carboxamide | (r)-(+)-1-(3-methoxyphen-yl)ethyl isocyanate | 2.0 | 657 |
| 58 | 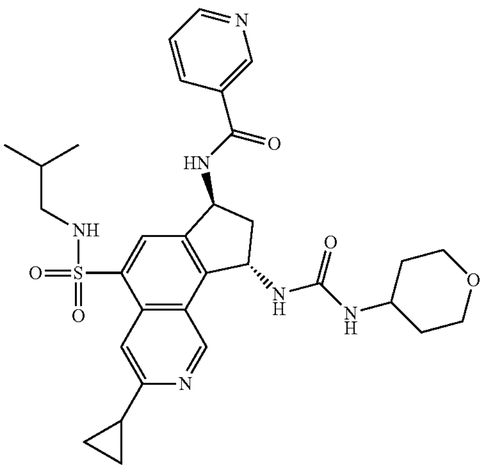 R,R and S,S | N-[trans-(7RS,9RS)-3-cyclopropyl-5-(2-methylpropylsulfamoyl)-9-(oxan-4-ylcarbamoylamino)-8,9-dihydro-7H-cyclopenta[h]isoquinolin-7-yl]pyridine-3-carboxamide | 4-isocyanatotetra-hydro-2h-pyran | 1.72 | 607 |
| 59 | 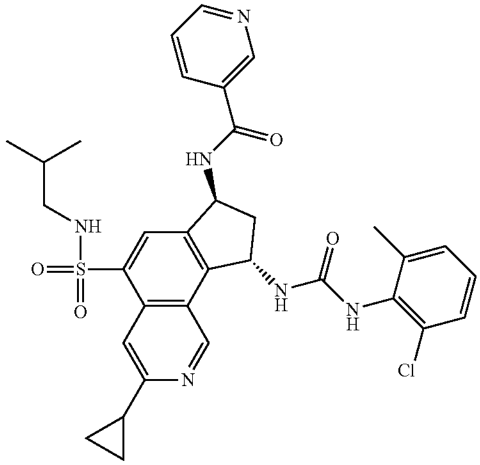 R,R and S,S | N-[trans-(4RS,9RS)-9-[(2-chloro-6-methylphenyl)carba-moylamino]-3-cyclopropyl-5-(2-methylpropylsulfamoyl)-8,9-dihydro-7H-cyclopenta[h]isoquinolin-7-yl]pyridine-3-carboxamide | 2-chloro-6-methylphenyl isocyanate | 2.06 | 647 |

Example 60

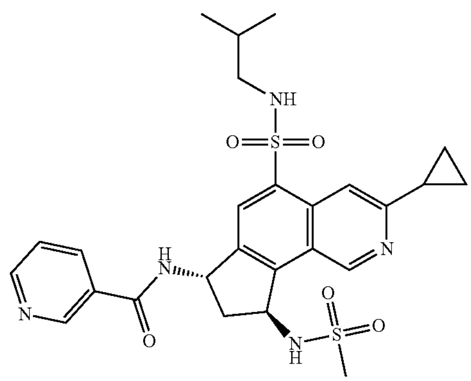

R,R and S,S

N-[trans-(7RS,9RS)-3-cyclopropyl-9-(methanesulfonamido)-5-(2-methylpropylsulfamoyl)-8,9-dihydro-7H-cyclopenta[h]isoquinolin-7-yl]pyridine-3-carboxamide To a mixture of Example 3 (10 mg, 0.02 mmol) and methanesulfonyl chloride (5 mg, 0.043 mmol) in DCM (0.6 mL, 9 mmol), N,N-diisopropylethylamine (10 μL, 0.057 mmol) was added. The reaction mixture was stirred at room temperature for 1 hour, the purified by reverse phase column chromatography (basic conditions) to give the title compound (7.1 mg, 60% yield) LCMS (ES+) m/z=558 $(M+H)^+$ RT=3.78 (Method 6).

Example 61

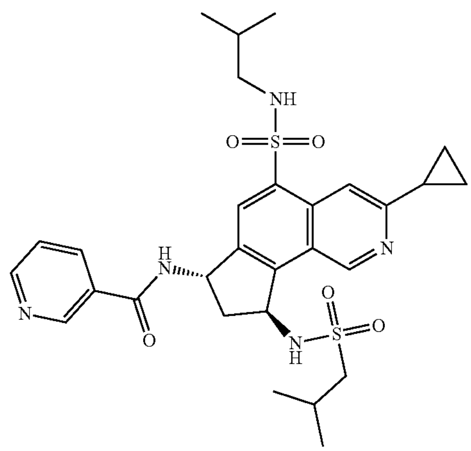

R,R and S,S

N-[trans-(7RS,9RS)-3-cyclopropyl-5-(2-methylpropylsulfamoyl)-9-(2-methylpropylsulfonylamino)-8,9-dihydro-7H-cyclopenta[h]isoquinolin-7-yl]pyridine-3-carboxamide To a mixture of Example 3 (9.6 mg, 0.02 mmol) and isobutanesulfonyl chloride (5 mg, 0.031 mmol) in DCM (500 μL), N,N-diisopropylethylamine (15 μL, 0.086 mmol) was added. The reaction mixture was stirred at room temperature overnight. Then a second and a third portion of isobutanesulfonyl chloride (10 and 15 mg respectively) were added and the reaction stirred for a further 3 hours at room temperature. Purification by reverse phase column chromatography (basic conditions) gave the title compound (3.4 mg, 30% Yield). LCMS (ES+) m/z=600 $(M+H)^+$ RT=4.11 (Method 6).

Example 62

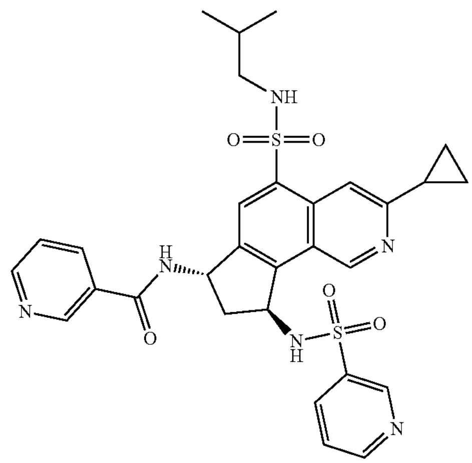

R,R and S,S

N-[trans-(7RS,9RS)-3-cyclopropyl-5-(2-methylpropylsulfamoyl)-9-(pyridin-3-ylsulfonylamino)-8,9-dihydro-7H-cyclopenta[h]isoquinolin-7-yl]pyridine-3-carboxamide To a mixture of Example 3 (10 mg, 0.02 mmol) and pyridine-3-sulfonyl chloride (6 mg, 0.03 mmol) in DCM (500 μL), N,N-diisopropylethylamine (15 μL, 0.086 mmol) was added. The reaction mixture was stirred at room temperature for 30 min. The solvent was removed, and the residue purified by reverse phase column chromatography (basic conditions) to give the title compound (7 mg, 60% Yield). LCMS (ES+) m/z=621 $(M+H)^+$ RT=2.25 (Method 6).

Example 63

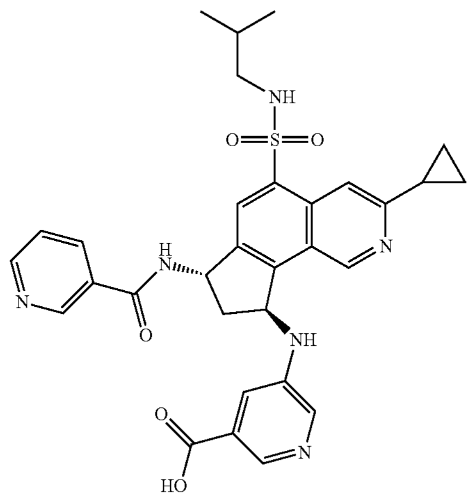

R, R and S, S

5-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]amino]pyridine-3-carboxylic acid A by-product in the procedure used to make example 48 above. The title compound was purified by preparative LCMS (initially under basic conditions, then under acidic conditions and finally under basic conditions to get the free acid). LCMS $[M+H]^+$ 601 with retention time 1.74 min (Method 6).

Example 64

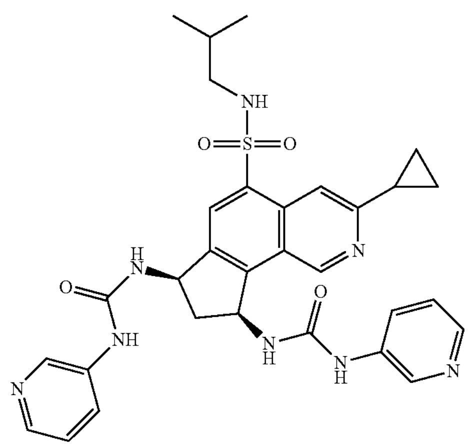

R, S and S, R 1-pyridin-3-yl-3-[cis-(7RS,9SR)-3-cyclopropyl-5-(2-methylpropylsulfamoyl)-7-(pyridin-3-ylcarbamoylamino)-8,9-dihydro-7H-cyclopenta[h]isoquinolin-9-yl]urea To a stirred suspension of intermediate 45 (100 mg, 0.267 mmol) in DCM (3 mL) at room temperature was added 3-isothiocyanatopyridine (90.9 mg, 0.75 mmol). The reaction was stirred at ambient temperature. DMF was added to aid solubilisation of isocyanate. An additional portion of 3-isothiocyanatopyridine (20 mg) was added and stirring continued for 90 min. Purification by HPLC (reverse phase basic conditions) gave the title compound (32 mg, 19% Yield). $^1H$ NMR (400 MHz, DMSO-d6) $\delta_H$ 9.49-9.40 (m, 1H), 8.90 (d, J=12.9 Hz, 2H), 8.58 (t, J=2.5 Hz, 2H), 8.37 (d, J=0.9 Hz, 1H), 8.20 (s, 1H), 8.18-8.08 (m, 3H), 7.99-7.89 (m, 2H), 7.33-7.24 (m, 2H), 7.16 (d, J=8.4 Hz, 1H), 7.00 (d, J=8.0 Hz, 1H), 5.86-5.74 (m, 1H), 5.30-5.20 (m, 1H), 3.22-3.10 (m, 1H), 2.61-2.52 (m, 2H), 2.31-2.22 (m, 1H), 1.99 (dt, J=13.4, 5.9 Hz, 1H), 1.59 (hept, J=6.7 Hz, 1H), 1.12-0.92 (m, 4H), 0.72 (dd, J=8.4, 6.7 Hz, 6H). LCMS (ES+) m/z=615 $(M+H)^+$, RT=1.80 (Method 15).

Examples 65 & 66

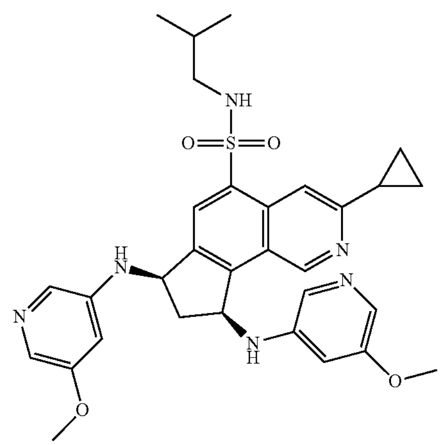

R, S and S, R

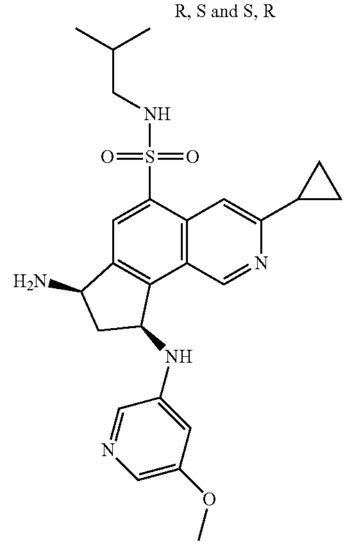

R, S and S, R cis-(7RS,9SR)-3-cyclopropyl-7,9-bis[(5-methoxy-pyridin-3-yl)aminol-N-(2-methylpropyl)-8,9-dihydro-7H-cyclopenta[h]isoquinoline-5-sulfonamide (65)

cis-(7RS,9SR)-7-amino-3-cyclopropyl-9-[(5-methoxypyridin-3-yl)aminol-N-(2-methylpropyl)-8,9-dihydro-7H-cyclopenta[h]isoquinoline-5-sulfonamide (66)

A mixture of intermediate 45 (100 mg, 0.27 mmol), 3-bromo-5-methoxy-pyridine (125 mg, 0.66 mmol), sodium tert-butoxide (103 mg, 1.07 mmol) and tBuXPhos PD G3 (54.67 mg, 0.067 mmol) was placed under an atmosphere of nitrogen prior to the addition of 1,4-dioxane (4 mL). The reaction mixture was sealed and stirred at ambient temperature for 2 h 45 min. The reaction was filtered through Celite, washing with EtOAc. The solvents were removed in vacuo and the resulting crude purified by HPLC (reverse phase basic conditions) to give the title compounds:

Example 65 (10.2 mg, 6.5% Yield). $^1$H NMR (300 MHz, DMSO-d6) $\delta_H$ 9.45 (d, J=0.9 Hz, 1H), 8.39 (d, J=0.9 Hz, 1H), 8.21 (s, 1H), 8.15 (t, J=6.0 Hz, 1H), 7.75 (t, J=2.5 Hz, 2H), 7.59 (t, J=2.1 Hz, 2H), 6.77 (dt, J=8.9, 2.4 Hz, 2H), 6.61 (d, J=9.4 Hz, 1H), 6.44 (d, J=8.8 Hz, 1H), 5.76-5.59 (m, 1H), 5.25-5.09 (m, 1H), 3.82-3.69 (m, 6H), 3.25-3.12 (m, 1H), 2.61-2.52 (m, 2H), 2.34-2.25 (m, 1H), 1.92-1.74 (m, 1H), 1.70-1.49 (m, 1H), 1.16-0.91 (m, 4H), 0.76 (dd, J=6.7, 5.0 Hz, 6H). LCMS (ES+) m/z=589 (M+H)$^+$, RT=2.23 (Method 15).

Example 66 (4.7 mg, 3.7% Yield). $^1$H NMR (300 MHz, DMSO-d6) $\delta_H$ 9.81 (s, 1H), 8.37 (s, 1H), 8.17 (s, 1H), 8.12 (t, J=5.7 Hz, 1H), 7.75 (d, J=2.3 Hz, 1H), 7.60 (d, J=2.4 Hz, 1H), 6.73 (t, J=2.4 Hz, 1H), 6.38 (d, J=9.1 Hz, 1H), 5.22-4.98 (m, 2H), 3.78 (s, 3H), 3.12-2.99 (m, 1H), 2.60-2.52 (m, 2H), 2.36-2.19 (m, 1H), 1.94-1.77 (m, 1H), 1.70-1.46 (m, 1H), 1.20-0.91 (m, 4H), 0.76 (dd, J=6.7, 4.8 Hz, 6H). LCMS (ES+) m/z=482 (M+H)$^+$, RT=1.94 (Method 15).

Example 67

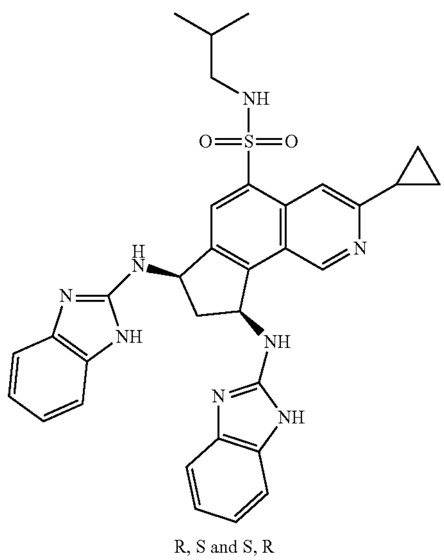 [SMILES: CC(C)CNS(=O)(=O)c1cc2c(c3cnc(C4CC4)cc13)[C@@H](Nc1nc3ccccc3[nH]1)C[C@H]2Nc1nc2ccccc2[nH]1]

R, S and S, R cis-(7RS,9SR)-7,9-bis(1H-benzimidazol-2-ylamino)-3-cyclopropyl-N-(2-methylpropyl)-8,9-dihydro-7H-cyclopenta[h]isoquinoline-5-sulfonamide To a stirred suspension of intermediate 45 (50 mg, 0.13 mmol) in 1-butanol (3 mL) at room temperature was added 2-chlorobenzimidazole (51 mg, 0.33 mmol). The reaction was sealed and stirred at 160° C. under microwave irradiation for 1 h then at 175° C. for 2 h. The reaction mixture was concentrated in vacuo and purified by HPLC (reverse phase basic conditions) to give the title compound (15 mg, 18% Yield). $^1$H NMR (300 MHz, DMSO-d6) $\delta_H$ 10.98 (d, J=12.5 Hz, 2H), 9.48 (d, J=0.9 Hz, 1H), 8.35 (d, J=1.0 Hz, 1H), 8.29 (s, 1H), 8.09 (t, J=5.9 Hz, 1H), 7.56 (d, J=9.2 Hz, 1H), 7.38 (d, J=8.8 Hz, 1H), 7.25 (t, J=8.0 Hz, 2H), 7.19-7.11 (m, 2H), 7.00-6.84 (m, 4H), 6.05 (td, J=8.7, 4.7 Hz, 1H), 5.48 (td, J=8.5, 4.8 Hz, 1H), 2.31-2.09 (m, 2H), 1.52 (hept, J=6.7 Hz, 1H), 1.13-0.91 (m, 4H), 0.67 (dd, J=6.7, 2.8 Hz, 6H). LCMS (ES+) m/z=607 (M+H)$^+$, RT=2.19 (Method 15)

Example 68

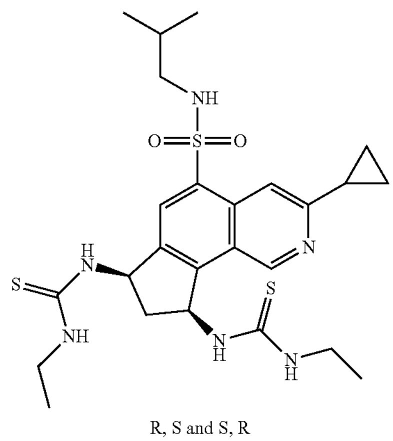 [SMILES: CCNC(=S)N[C@H]1C[C@@H](NC(=S)NCC)c2cc(S(=O)(=O)NCC(C)C)c3cc(C4CC4)ncc3c21]

R, S and S, R 1-ethyl-3-[cis-(7RS,9SR)-3-cyclopropyl-7-(ethylcarbamothioylamino)-5-(2-methylpropylsulfamoyl)-8,9-dihydro-7H-cyclopenta[h]isoquinolin-9-yl]thiourea Intermediate 45 (200 mg) was dissolved in MeOH (5 mL) and absorbed on an SCX cartridge. The cartridge was washed with MeOH and the free base eluted with 4 M $NH_3$ in MeOH. The solvent was removed, the resulting free base (150 mg, 0.40 mmol) was dissolved in DCM (9 mL), ethyl isothiocyanate (79.1 mg, 0.881 mmol) was added and the reaction stirred at ambient temperature overnight. The reaction was concentrated in vacuo and purified by column chromatography (0-100% gradient of EtOAc in isohexane) to give the title compound (7 mg, 3% Yield). $^1$H NMR (300 MHz, DMSO-d6) $\delta_H$ 9.35 (s, 1H), 8.36 (d, J=1.0 Hz, 1H), 8.22 (s, 1H), 8.13 (t, J=5.9 Hz, 1H), 8.07-7.89 (m, 1H), 7.87-7.50 (m, 3H), 6.71-6.42 (m, 1H), 6.02-5.74 (m, 1H), 3.80-3.35 (m, 4H), 3.14 (dt, J=13.2, 8.2 Hz, 1H), 2.63-2.53 (m, 2H), 2.34-2.21 (m, 1H), 1.92-1.74 (m, 1H), 1.62 (hept, J=6.7 Hz, 1H), 1.19-0.96 (m, 10H), 0.77 (dd, J=6.7, 4.9 Hz, 6H). LCMS (ES+) m/z=549 (M+H)$^+$, RT=2.22 (Method 15)

Example 69

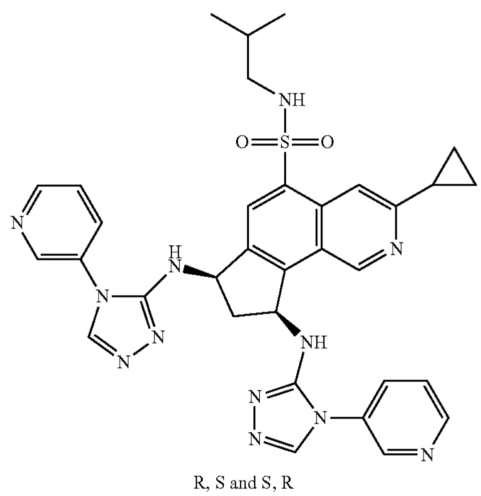 [SMILES: CC(C)CNS(=O)(=O)c1cc2c(c3cnc(C4CC4)cc13)[C@@H](Nc1nncn1-c1cccnc1)C[C@H]2Nc1nncn1-c1cccnc1]

R, S and S, R cis-(7RS,9SR)-3-cyclopropyl-N-(2-methyl propyl)-7,9-bis[(4-pyridin-3-yl-1,2,4-triazol-3-yl)aminol-8,9-dihydro-7H-cyclopenta[h]isoquinoline-5-sulfonamide To a solution of intermediate 46 (113 mg, 0.1747 mmol) in N,N-dimethylformamide (6 mL) were added formic acid hydrazide (42 mg, 0.701 mmol) and mercuric chloride (143 mg, 0.52 mmol). triethylamine (0.097 mL, 0.701 mmol) was then added and the reaction suspension heated to 80° C. for 2 h then left to stand at room temperature overnight. The reaction mixture was filtered through a plug of Celite, washing with EtOAc (10 mL). The solvents were removed in vacuo and the resulting crude residue containing several regioisomers was purified by HPLC to give the title compound (5 mg, 4% Yield). $^1$H NMR (300 MHz, DMSO-d6) $\delta_H$ 9.62 (s, 1H), 8.76-8.64 (m, 3H), 8.49-8.38 (m, 1H), 8.33 (s, 1H), 8.29-8.20 (m, 1H), 8.12-8.01 (m, 2H), 8.01-7.91 (m, 1H), 7.88-7.79 (m, 1H), 7.67-7.56 (m, 1H), 7.41-7.19 (m, 2H), 6.00 (t, J=8.1 Hz, 1H), 5.91-5.76 (m, 1H), 3.50-3.37 (m, 1H), 2.45-2.19 (m, 4H), 1.55-1.36 (m, 1H), 1.24 (s, 1H), 1.09-1.00 (m, 4H), 0.89-0.80 (m, 1H), 0.66 (dd, J=6.4 Hz, 6H). LCMS (ES+) m/z=663 $(M+H)^+$, RT=1.53 (Method 15).

Example 70

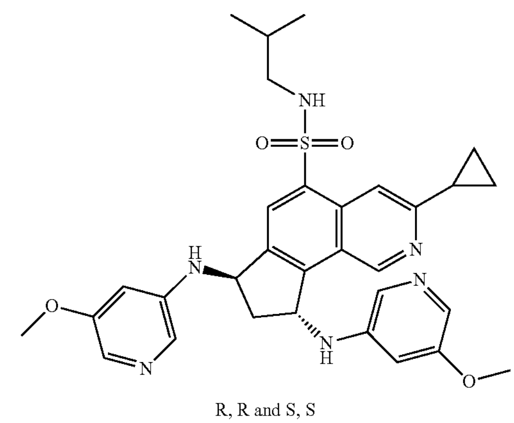

R, R and S, S trans-(7RS,9RS)-3-cyclopropyl-7,9-bis[(5-methoxy-pyridin-3-yl)aminol-N-(2-methylpropyl)-8,9-dihydro-7H-cyclopenta[h]isoquinoline-5-sulfonamide A vial was charged with intermediate 51 (50 mg, 0.11 mmol), 3-bromo-5-methoxypyridine (55 mg, 0.28 mmol), sodium tert-butoxide (42 mg, 0.44 mmol), methanesulfonato (2-di-tert-butylphosphino-2',4',6'-tri-iso-propyl-1,1'-biphenyl)(2'-amino-1,1'-biphenyl-2-yl)palladium (II) (22 mg, 0.03 mmol) and anhydrous dioxane (3 mL) and the resultant mixture was subjected to vacuum and backfilled with $N_2$ (×2), purged with $N_2$ for 5 min then heated to 80° C. for 50 min. The reaction mixture was filtered through Celite (EtOAc washings with a few mL of MeOH) and concentrated in vacuo. Purification by column chromatography eluting with 0-30% MeOH in DCM followed by reverse phase column chromatography eluting with 0-80% MeCN in $H_2O$ gave the title compound (31 mg, 49% yield). $^1$H NMR (400 MHz, DMSO-d6) $\delta_H$ 9.28 (d, J=0.9 Hz, 1H), 8.39 (d, J=0.9 Hz, 1H), 8.16 (d, J=5.2 Hz, 2H), 7.71 (dd, J=3.8, 2.3 Hz, 2H), 7.58 (dd, J=8.8, 2.4 Hz, 2H), 6.72 (t, J=2.4 Hz, 1H), 6.65 (t, J=2.4 Hz, 1H), 6.48 (d, J=8.8 Hz, 1H), 6.42 (d, J=8.6 Hz, 1H), 5.82 (t, J=7.7 Hz, 1H), 5.50-5.38 (m, 1H), 3.78 (s, 3H), 3.75 (s, 3H), 2.59-2.51 (m, 3H), 2.38 (dt, J=13.5, 7.0 Hz, 1H), 2.28 (q, J=6.4 Hz, 1H), 1.59 (dt, J=13.4, 6.7 Hz, 1H), 1.08-0.98 (m, 4H), 0.75 (d, J=6.7 Hz, 6H). LCMS $[M+H]^+$ 589, RT 2.12 minutes (Method 10).

Example 71

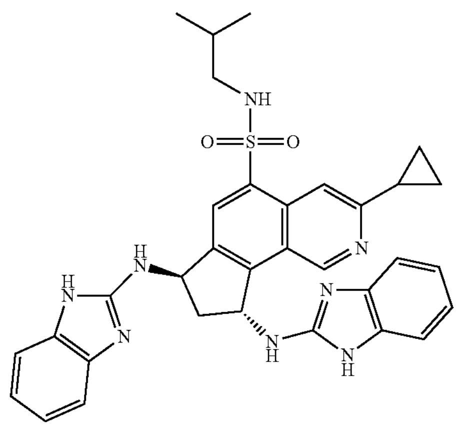

R, R and S, S trans-(7RS,9RS)-7,9-bis(1H-benzimidazol-2-ylamino)-3-cyclopropyl-N-(2-methylpropyl)-8,9-dihydro-7H-cyclopenta[h]isoquinoline-5-sulfonamide A microwave vial was charged with intermediate 51 (30 mg, 0.07 mmol), 1-butanol (2 mL), DIPEA (25 μL, 0.14 mmol) and 2-chlorobenzimidazole (25 mg, 0.1638 mmol). The resultant mixture was heated at 175° C. for 2 h under microwave irradiation. The reaction mixture was concentrated in vacuo and purified by column chromatography eluting with 0-30% MeOH in DCM followed by a second column eluting with 10% MeOH in EtOAc to give the title compound (3 mg, 7% yield). $^1$H NMR (300 MHz, DMSO-$d_6$) $\delta_H$ 10.89 (s, 1H), 10.75 (s, 1H), 9.43 (s, 1H), 8.36 (d, J=0.9 Hz, 1H), 8.29 (s, 1H), 8.10 (t, J=5.9 Hz, 1H), 7.42 (d, J=9.0 Hz, 1H), 7.29-7.11 (m, 5H), 7.00-6.83 (m, 4H), 6.27 (t, J=7.7 Hz, 1H), 5.95 (q, J=7.7 Hz, 1H), 2.72-2.51 (m, 4H), 2.26 (s, 1H), 1.56 (p, J=6.8 Hz, 1H), 1.08-0.93 (m, 4H), 0.71 (d, J=6.7 Hz, 6H). LCMS $[M+H]^+$ 607, RT 2.14 minutes (Method 10).

Examples 72 & 73

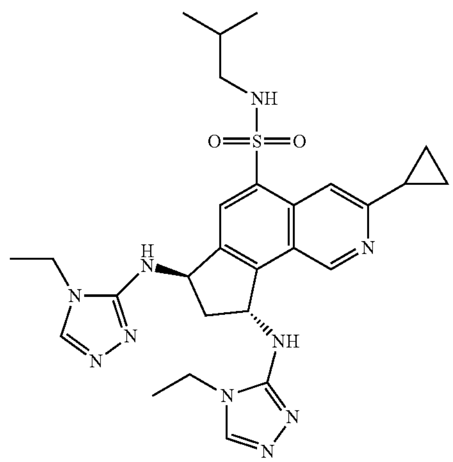

R, R and S, S

-continued

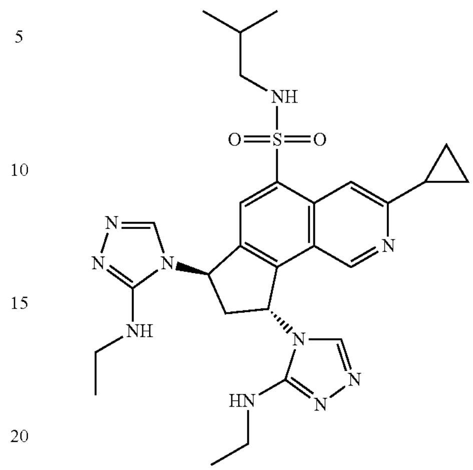

R, R and S, S trans-(7RS,9RS)-3-cyclopropyl-7,9-bis[(4-ethyl-1,2,4-triazol-3-yl)aminol-N-(2-methylpropyl)-8,9-dihydro-7H-cyclopenta[h]isoquinoline-5-sulfonamide (72) trans-(7RS,9RS)-3-cyclopropyl-7,9-bis[3-(ethylamino)-1,2,4-triazol-4-yl]-N-(2-methylpropyl)-8,9-dihydro-7H-cyclopenta[h]isoquinoline-5-sulfonamide (73)

To a solution of intermediate 52 (623 mg, 1.14 mmol) in anhydrous DMF (30 mL) were added formic acid hydrazide (280 mg, 4.66 mmol) and mercuric chloride (930 mg, 3.41 mmol). Anhydrous TEA (650 μL, 4.66 mmol) was then added and the mixture heated to 80° C. for 16 h. The reaction mixture was then filtered through Celite (MeCN washings) and concentrated in vacuo. Purification by column chromatography eluting with 0-50% MeOH in DCM then basic reverse phase column chromatography eluting with 0-80% MeCN in $H_2O$ gave the title compounds:

Example 72 (135 mg, 21% yield). $^1$H NMR (400 MHz, Methanol-d4) $\delta_H$ 9.32 (d, J=0.9 Hz, 1H), 8.43 (d, J=0.9 Hz, 1H), 8.38 (s, 1H), 8.12 (d, J=3.0 Hz, 2H), 6.01 (dd, J=7.5, 2.3 Hz, 1H), 5.70 (t, J=7.3 Hz, 1H), 3.91 (q, J=7.2 Hz, 2H), 3.82 (q, J=7.2 Hz, 2H), 2.84 (ddd, J=14.0, 7.6, 2.4 Hz, 1H), 2.72-2.55 (m, 3H), 2.34-2.26 (m, 1H), 1.65 (dt, J=13.5, 6.7 Hz, 1H), 1.39 (t, J=7.3 Hz, 3H), 1.31-1.26 (m, 3H), 1.13-1.07 (m, 4H), 0.81 (dd, J=6.7, 3.9 Hz, 6H). LCMS $[M+H]^+$ 565, RT 1.60 minutes (Method 10).

Example 73 (4 mg, 1% yield). $^1$H NMR (400 MHz, Methanol-d4) $\delta_H$ 8.90 (d, J=0.9 Hz, 1H), 8.51 (d, J=0.9 Hz, 1H), 8.18 (s, 1H), 7.81 (s, 1H), 7.50 (s, 1H), 6.50 (dd, J=7.3, 3.9 Hz, 1H), 6.19 (t, J=6.9 Hz, 1H), 3.53-3.39 (m, 4H), 3.04-2.95 (m, 2H), 2.69 (dd, J=6.9, 3.9 Hz, 2H), 2.37-2.27 (m, 1H), 1.62 (dt, J=13.4, 6.7 Hz, 1H), 1.35 (dt, J=20.5, 7.2 Hz, 6H), 1.14-1.08 (m, 4H), 0.79 (dd, J=6.7, 4.1 Hz, 6H).

LCMS $[M+H]^+$ 565, RT 1.52 minutes (Method 10).

Example 74

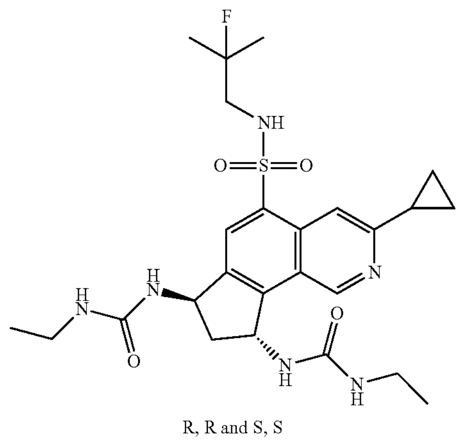 [SMILES: CCNC(=O)N[C@@H]1C[C@@H](NC(=O)NCC)c2c1cc(S(=O)(=O)NCC(C)(C)F)c1cc(C3CC3)ncc21]

R, R and S, S 1-ethyl-3-[trans-(7RS,9RS)-3-cyclopropyl-7-(ethylcarbamoylamino)-5-[(2-fluoro-2-methylpropyl)sulfamoyl]-8,9-dihydro-7H-cyclopenta[h]isoquinolin-9-yl]urea Synthesised in the same manner as intermediate 50 using intermediate 59 (74 mg, 0.14 mmol) and comparable stoichiometries of reagents heating at 120° C. for 12 h. Purification by reverse phase column chromatography (basic conditions) gave the title compound (4 mg, 5% yield). $^1$H NMR (400 MHz, DMSO-d6) $\delta_H$ 9.37 (s, 1H), 8.40 (s, 2H), 8.11 (s, 1H), 6.62 (d, J=8.8 Hz, 1H), 6.38 (d, J=8.6 Hz, 1H), 5.95-5.82 (m, 2H), 5.62 (t, J=5.6 Hz, 1H), 5.54 (d, J=8.0 Hz, 1H), 3.16-2.98 (m, 5H), 2.91 (d, J=19.5 Hz, 2H), 2.24 (ddd, J=21.3, 12.7, 7.5 Hz, 2H), 1.23 (dd, J=21.4, 6.0 Hz, 6H), 1.03 (dd, J=8.3, 6.2 Hz, 6H), 0.98 (t, J=7.2 Hz, 4H). LCMS $[M+H]^+$ 535, RT 1.61 minutes (Method 10).

Example 75

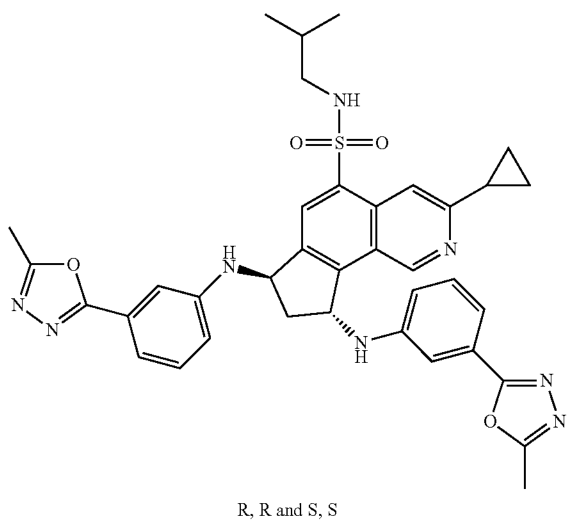 [SMILES: Cc1nnc(-c2cccc(N[C@@H]3C[C@@H](Nc4cccc(-c5nnc(C)o5)c4)c4c3cc(S(=O)(=O)NCC(C)C)c3cc(C5CC5)ncc43)c2)o1]

R, R and S, S trans-(7RS,9RS)-3-cyclopropyl-7,9-bis[3-(5-methyl-1,3,4-oxadiazol-2-yl)anilino]-N-(2-methylpropyl)-8,9-dihydro-7H-cyclopenta[h]isoquinoline-5-sulfonamide Synthesised in the same manner as Example 70 using intermediate 51 (30 mg, 0.07 mmol) and 2-(3-bromophenyl)-5-methyl-1,3,4-oxadiazole with comparable stoichiometries of reagents. Purification by column chromatography eluting with 0-30% MeOH in DCM followed by reverse phase HPLC (basic conditions) gave the title compound (21 mg, 48% yield). $^1$H NMR (400 MHz, DMSO-$d_6$) $\delta_H$ 9.29 (s, 1H), 8.39 (s, 1H), 8.19 (s, 1H), 8.14 (t, J=6.0 Hz, 1H), 7.39-7.28 (m, 4H), 7.20 (ddt, J=10.3, 7.8, 1.1 Hz, 2H), 7.03-6.92 (m, 2H), 6.63 (dd, J=19.5, 8.6 Hz, 2H), 5.88 (t, J=7.7 Hz, 1H), 5.51 (q, J=7.4 Hz, 1H), 2.66-2.58 (m, 1H), 2.57-2.52 (m, 8H), 2.45-2.37 (m, 1H), 2.31-2.24 (m, 1H), 1.58 (hept, J=6.7 Hz, 1H), 1.11-0.97 (m, 4H), 0.73 (dd, J=6.7, 2.5 Hz, 6H). LCMS $[M+H]^+$ 691, RT 2.46 minutes (Method 10).

Example 76

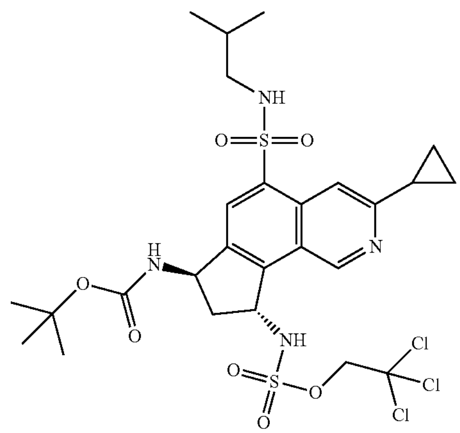

R, R and S, S tert-butyl N-[trans-(7RS,9RS)-3-cyclopropyl-5-(2-methylpropylsulfamoyl)-9-(2,2,2-trichloroethoxysulfonylamino)-8,9-dihydro-7H-cyclopenta[h]isoquinolin-7-yl]carbamate A vial was charged with magnesium oxide (160 mg, 3.97 mmol) and 4 Å molecular sieves and dried under vacuum. 2,2,2-trichloroethyl sulfamate (300 mg, 1.27 mmol), 2-methyl-2-phenylpropionic acid (80 mg, 0.48 mmol) and bis[rhodium(alpha, alpha, alpha', alpha'-tetramethyl-1,3-benzenedipropionic acid)](40 mg, 0.05 mmol) were then added under $N_2$ followed by isopropyl acetate (7 mL) and intermediate 13 (450 mg, 0.98 mmol). After 5 min, iodobenzene diacetate (640 mg, 1.95 mmol) was added to the mixture, which was stirred at room temperature. After 2 h 40 min, the reaction mixture was quenched with sat. aq. thiourea (2 mL) then dilute with DCM (40 mL) and $H_2O$ (40 mL) and the phases separated. The aqueous was extracted with DCM (4×20 mL), dried (phase separator) and concentrated in vacuo. Purification by column chromatography eluting with 0-50% EtOAc in iso-hexane gave a mixture of cis and trans isomers which was further purified using reverse phase HPLC (basic conditions) to give the title compound (6 mg, 1% yield). $^1$H NMR (300 MHz, DMSO-$d_6$) $\delta_H$ 9.56 (s, 1H), 8.33 (s, 1H), 8.09 (s, 2H), 7.41 (s, 1H), 5.51 (s, 1H), 5.37 (s, 1H), 4.72 (s, 2H), 2.60-2.53 (m, 3H), 2.33-2.24 (m, 2H), 1.61 (q, J=6.6 Hz, 1H), 1.44 (s, 9H), 1.12-0.97 (m, 4H), 0.77 (d, J=6.6 Hz, 6H) [Note: 1H is missing due to a weak NMR]. LCMS $[M+H]^+$ 687, RT 2.31 minutes (Method 11).

Example 77

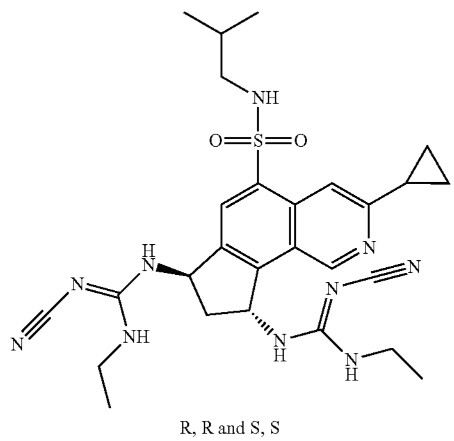 [SMILES: CCN/C(=N\C#N)N[C@@H]1C[C@@H](N/C(=N/C#N)NCC)c2c1cc(S(=O)(=O)NCC(C)C)c1cc(C3CC3)ncc21]

R, R and S, S 2-cyano-1-ethyl-3-[trans-(7RS,9RS)-3-cyclopropyl-5-(2-methylpropylsulfamoyl)-7-[[rac-(E)-N'-cyano-N-ethylcarbamimidoyl]aminol-8,9-dihydro-7H-cyclopenta[h]isoquinolin-9-yl]guanidine A vial was charged with intermediate 51 (30 mg, 0.07 mmol), DCM (2 mL), DIPEA (100 μL, 0.57 mmol) and diphenyl N-cyanocarbonimidate (35 mg, 0.14 mmol) and the mixture stirred at room temperature. After 3 h, ethylamine (1 mL, 2 mmol) was added and the mixture heated at 70° C. for 1 h then concentrated in vacuo. Purification by reverse phase HPLC (basic conditions) gave the title compound (19 mg, 49% yield). $^1$H NMR (400 MHz, DMSO-d6)$^{6H}$ 9.24 (d, J=0.9 Hz, 1H), 8.38 (d, J=1.0 Hz, 1H), 8.20 (s, 1H), 8.11 (s, 1H), 7.50 (d, J=8.8 Hz, 1H), 7.34 (d, J=8.5 Hz, 1H), 7.28-7.17 (m, 2H), 6.11 (s, 1H), 5.83 (q, J=7.7 Hz, 1H), 3.22-3.05 (m, 4H), 2.64-2.52 (m, 3H), 2.42 (ddd, J=13.7, 8.1, 3.0 Hz, 1H), 2.32-2.25 (m, 1H), 1.64 (hept, J=6.7 Hz, 1H), 1.09-1.03 (m, 7H), 0.98 (t, J=7.1 Hz, 3H), 0.79 (dd, J=6.6, 1.5 Hz, 6H). LCMS $[M+H]^+$ 565, RT 1.82 minutes (Method 10).

Example 78

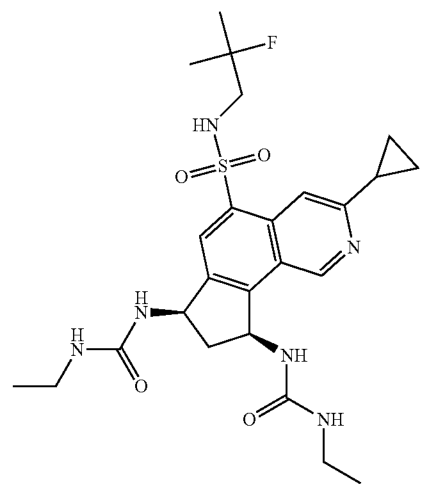

R, S and S, R 1-ethyl-3-[cis-(7RS,9SR)-3-cyclopropyl-7-(ethylcarbamoylamino)-5-[(2-fluoro-2-methylpropyl)sulfamoyl]-8,9-dihydro-7H-cyclopenta[h]isoquinolin-9-yl]urea Synthesised in the same manner as intermediate 50 using intermediate 61 (60 mg, 0.11 mmol) and comparable stoichiometries of reagents heating at 120° C. for 2 h. Purification by reverse phase column chromatography (basic conditions) gave the title compound (10 mg, 16% yield). $^1$H NMR (400 MHz, DMSO-$d_6$) $\delta_H$ 9.39 (s, 1H), 8.41 (s, 2H), 8.09 (s, 1H), 6.62 (d, J=8.9 Hz, 1H), 6.43 (d, J=8.5 Hz, 1H), 6.02 (t, J=5.6 Hz, 1H), 5.97 (d, J=6.0 Hz, 1H), 5.64 (q, J=7.9 Hz, 1H), 5.09 (q, J=7.9 Hz, 1H), 3.12-3.03 (m, 4H), 3.02-2.94 (m, 1H), 2.90 (d, J=21.6 Hz, 2H), 2.27 (s, 1H), 1.79-1.66 (m, 1H), 1.21 (dd, J=21.4, 9.3 Hz, 6H), 1.09-0.96 (m, 10H). LCMS $[M+H]^+$ 535, RT 1.62 minutes (Method 10).

Example 79-87

All entries in the following table were made according the either general procedure 1 or general procedure 2 (depending on the substrate used) with intermediate 51.

LCMS data in the table was obtained using LCMS Method 10.

| Example | structure<br>$^1$H NMR | IUPAC name | substrate | RT | Mass |
|---|---|---|---|---|---|
| 79 | 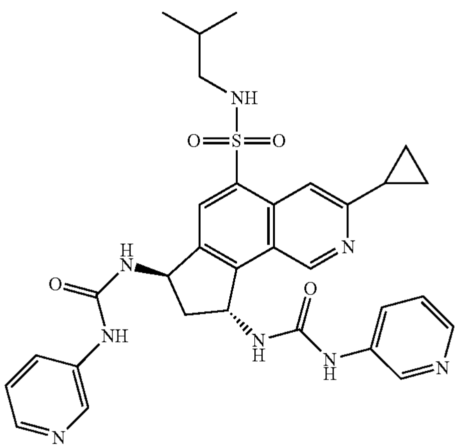<br>R,R and S,S | 1-pyridin-3-yl-3-[trans-(7RS,9RS)-3-cyclopropyl-5-(2-methylpropylsulfamoyl)-7-(pyridin-3-ylcarbamoylamino)-8,9-dihydro-7H-cyclopenta[h]isoquinolin-9-yl]urea | 3-isocyanato-pyridine | 1.74 | 615 |
| | $^1$H NMR (300 MHz, DMSO-$d_6$) $\delta_H$ 9.41 (s, 1H), 8.80 (s, 1H), 8.57 (dd, J = 13.6, 2.6 Hz, 2H), 8.50 (s, 1H), 8.38 (s, 1H), 8.21 (s, 1H), 8.14 (ddd, J = 5.1, 3.8, 1.5 Hz, 3H), 7.98-7.87 (m, 2H), 7.33-7.17 (m, 3H), 6.98 (d, J = 8.3 Hz, 1H), 5.99 (t, J = 7.6 Hz, 1H), 5.69 (q, J = 7.7 Hz, 1H), 2.57 (d, J = 6.8 Hz, 2H), 2.47-2.41 (m, 2H), 2.30-2.24 (m, 1H), 1.60 (dt, J = 13.3, 6.6 Hz, 1H), 1.12-0.98 (m, 4H), 0.74 (dd, J = 6.7, 3.4 Hz, 6H). | | | | |
| 80 | 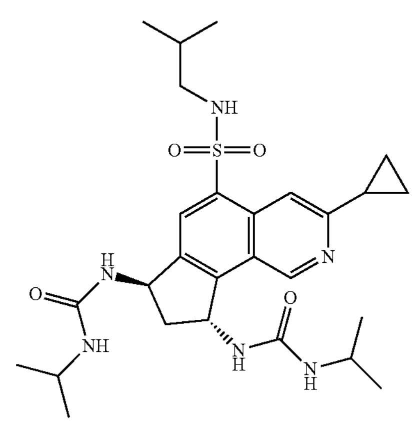<br>R,R and S,S | 1-propan-2-yl-3-[trans-(7RS,9RS)-3-cyclopropyl-5-(2-methylpropylsulfamoyl)-7-(propan-2-ylcarbamoylamino)-8,9-dihydro-7H-cyclopenta[h]isoquinolin-9-yl]urea | isopropyl isocyanate | 1.95 | 545 |
| | $^1$H NMR (400 MHz, DMSO-$d_6$) $\delta_H$ 9.38 (s, 1H), 8.34 (s, 1H), 8.12 (s, 2H), 6.49 (d, J = 9.0 Hz, 1H), 6.26 (d, J = 8.5 Hz, 1H), 5.84 (t, J = 7.5 Hz, 1H), 5.76 (d, J = 7.8 Hz, 1H), 5.56-5.46 (m, 2H), 3.80-3.66 (m, 2H), 2.57-2.52 (m, 2H), 2.38-2.16 (m, 3H), 1.61 (dt, J = 13.4, 6.7 Hz, 1H), 1.10-0.99 (m, 16H), 0.77 (dd, J = 6.7, 1.8 Hz, 6H) | | | | |

-continued

| Example | structure<br>$^1$H NMR | IUPAC name | substrate | RT | Mass |
| --- | --- | --- | --- | --- | --- |
| 81 | 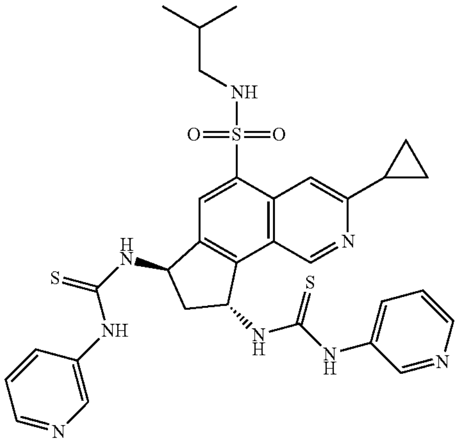<br>R,R and S,S | 1-pyridin-3-yl-3-[trans-(7RS,9RS)-3-cyclopropyl-5-(2-methylpropylsulfamoyl)-7-(pyridin-3-ylcarbamothioylamino)-8,9-dihydro-7H-cyclopenta[h]isoquinolin-9-yl]thiourea | 3-pyridyl isothiocyanate | 1.96 | 647 |
| | $^1$H NMR (400 MHz, DMSO-$d_6$) $\delta_H$ 9.88 (s, 1H), 9.61 (s, 1H), 9.43 (s, 1H), 8.84 (s, 1H), 8.71-8.55 (m, 2H), 8.52 (s, 1H), 8.39 (s, 1H), 8.35 (s, 1H), 8.29 (dd, J = 9.3, 4.6 Hz, 2H), 8.22 (s, 1H), 7.92 (dd, J = 18.5, 8.2 Hz, 2H), 7.41-7.28 (m, 2H), 6.78 (s, 1H), 6.45 (s, 1H), 2.64-2.55 (m, 4H), 2.31-2.26 (m, 1H), 1.64 (dq, J = 13.5, 6.7 Hz, 1H), 1.12-1.02 (m, 4H), 0.79 (dd, J = 6.6, 2.3 Hz, 6H). | | | | |
| 82 | 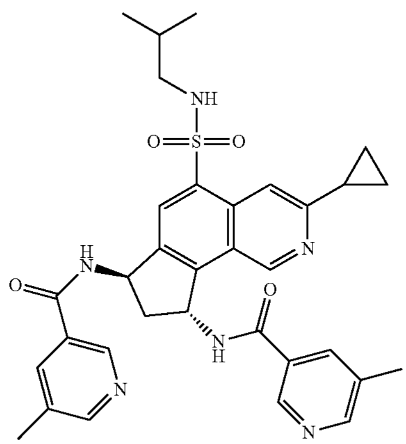<br>R,R and S,S | 5-methyl-N-[trans-(7RS,9RS)-3-cyclopropyl-5-(2-methylpropylsulfamoyl)-9-[(5-methylpyridine-3-carbonyl]amino]-8,9-dihydro-7H-cyclopenta[h]isoquinolin-7-yl]pyridine-3-carboxamide | 5-methylnicotinyl chloride | 1.92 | 613 |
| | $^1$H NMR (400 MHz, DMSO-$d_6$) $\delta_H$ 9.35 (s, 1H), 9.27 (d, J = 8.7 Hz, 1H), 9.14 (d, J = 8.3 Hz, 1H), 8.89 (d, J = 2.1 Hz, 1H), 8.83 (d, J = 2.1 Hz, 1H), 8.58 (d, J = 2.0 Hz, 1H), 8.54 (d, J = 2.0 Hz, 1H), 8.38 (s, 1H), 8.17 (s, 1H), 8.14 (s, 1H), 8.09 (d, J = 2.4 Hz, 1H), 8.04 (d, J = 2.3 Hz, 1H), 6.40 (t, J = 8.3 Hz, 1H), 6.20 (q, J = 7.8 Hz, 1H), 2.76-2.68 (m, 1H), 2.65-2.55 (m, 3H), 2.36 (s, 3H), 2.33 (s, 3H), 2.31-2.22 (m, 1H), 1.60 (dt, J = 13.7, 6.9 Hz, 1H), 1.09-0.97 (m, 4H), 0.74 (t, J = 7.1 Hz, 6H). | | | | |

-continued

| Example | structure $^1$H NMR | IUPAC name | substrate | RT | Mass |
|---|---|---|---|---|---|
| 83 | 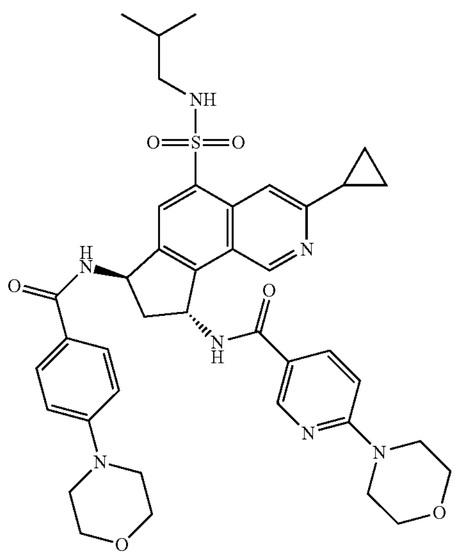 R,R and S,S | 6-morpholin-4-yl-N-[trans-(7RS,9RS)-3-cyclopropyl-5-(2-methylpropylsulfamoyl)-9-[(6-morpholin-4-ylpyridine-3-carbonyl)amino]-8,9-dihydro-7H-cyclopenta[h]isoquinolin-7-yl]pyridine-3-carboxamide | 6-morpholinonicotinoyl chloride | 2.02 | 755 |
| | 1H NMR (400 MHz, DMSO-d6) $\delta_H$ 9.34 (d, J = 0.9 Hz, 1H), 8.92 (d, J = 8.8 Hz, 1H), 8.75 (d, J = 8.4 Hz, 1H), 8.69 (d, J = 2.5 Hz, 1H), 8.65 (d, J = 2.4 Hz, 1H), 8.36 (d, J = 1.0 Hz, 1H), 8.14 (t, J = 5.9 Hz, 1H), 8.11 (s, 1H), 8.05 (dd, J = 9.0, 2.5 Hz, 1H), 8.00 (dd, J = 9.1, 2.5 Hz, 1H), 6.88 (d, J = 9.1 Hz, 1H), 6.84 (d, J = 9.1 Hz, 1H), 6.37 (t, J = 8.1 Hz, 1H), 6.16 (q, J = 7.8 Hz, 1H), 3.73-3.64 (m, 8H), 3.55 (dt, J = 9.7, 4.9 Hz, 8H), 2.71-2.62 (m, 1H), 2.55 (q, J = 6.3 Hz, 3H), 2.30-2.21 (m, 1H), 1.59 (dq, J = 13.4, 6.7 Hz, 1H), 1.02 (dd, J = 7.2, 4.8 Hz, 4H), 0.74 (t, J = 6.8 Hz, 6H). | | | | |
| 84 | 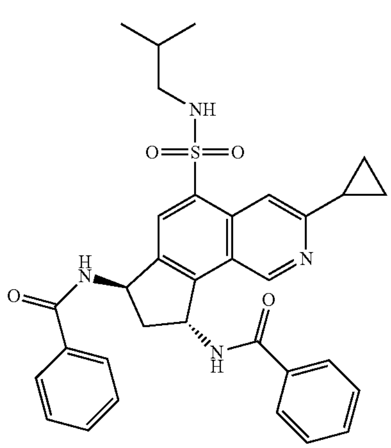 R,R and S,S | N-[trans-(7RS,9RS)-9-benzamido-3-cyclopropyl-5-(2-methylpropylsulfamoyl)-,8,9-dihydro-7H-cyclopenta[h]isoquinolin-7-yl]benzamide | benzoyl chloride | 1.32 | 583 |
| | $^1$H NMR (400 MHz, DMSO-$d_6$) $\delta_H$ 9.35 (s, 1H), 9.16 (d, J = 8.9 Hz, 1H), 8.98 (d, J = 8.4 Hz, 1H), 8.37 (d, J = 1.0 Hz, 1H), 8.19-8.12 (m, 2H), 7.96-7.86 (m, 4H), 7.60-7.41 (m, 6H), 6.39 (t, J = 8.2 Hz, 1H), 6.20 (q, J = 7.7 Hz, 1H), 2.76-2.69 (m, 1H), 2.64-2.52 (m, 3H), 2.27 (p, J = 6.5 Hz, 1H), 1.60 (dt, J = 13.5, 6.7 Hz, 1H), 1.08-0.96 (m, 4H), 0.74 (dd, J = 7.7, 6.7 Hz, 6H). | | | | |

-continued

| Example | structure<br>$^1H$ NMR | IUPAC name | substrate | RT | Mass |
|---|---|---|---|---|---|
| 85 | 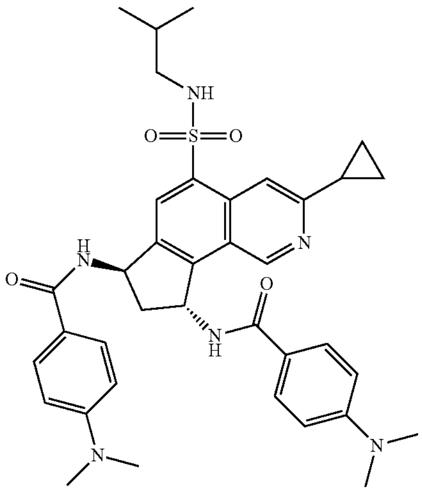<br>R,R and S,S | 4-(dimethylamino)-N-[trans-(7RS,9RS)-3-cyclopropyl-9-[[4-(dimethylamino)benzoyl]amino]-5-(2-methylpropylsulfamoyl)-8,9-dihydro-7H-cyclopenta[h]isoquinolin-7-yl]benzamide | 4-dimethylaminobenzoyl chloride | 2.48 | 669 |
| | $^1H$ NMR (400 MHz, DMSO-$d_6$) $\delta_H$ 9.34 (s, 1H), 8.78 (d, J = 9.0 Hz, 1H), 8.58 (d, J = 8.5 Hz, 1H), 8.35 (s, 1H), 8.11 (s, 2H), 7.83-7.70 (m, 4H), 6.76-6.64 (m, 4H), 6.38 (t, J = 8.2 Hz, 1H), 6.17 (q, J = 7.8 Hz, 1H), 2.97 (s, 6H), 2.95 (s, 6H), 2.72-2.59 (m, 1H), 2.52 (s, 3H), 2.30-2.20 (m, 1H), 1.65-1.54 (m, 1H), 1.08-0.95 (m, 4H), 0.74 (t, J = 6.9 Hz, 6H). | | | | |
| 86 | 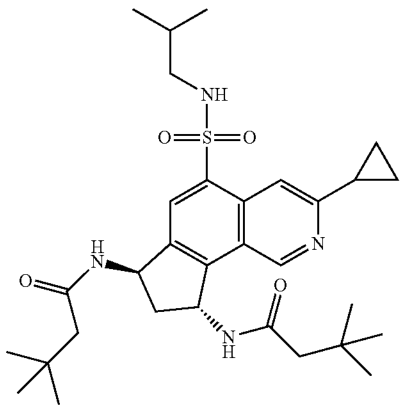<br>R,R and S,S | 3,3-dimethyl-N-[trans-(7RS,9RS)-3-cyclopropyl-9-(3,3-dimethylbutanoylamino)-5-(2-methylpropylsulfamoyl)-8,9-dihydro-7H-cyclopenta[h]isoquinolin-7-yl]butanamide | tert-butylacetyl chloride | 2.40 | 571 |
| | $^1H$ NMR (400 MHz, DMSO-$d_6$) $\delta_H$ 9.32 (s, 1H), 8.43 (d, J = 8.9 Hz, 1H), 8.33 (d, J = 0.9 Hz, 1H), 8.29 (d, J = 8.2 Hz, 1H), 8.14-8.09 (m, 2H), 6.02 (t, J = 7.9 Hz, 1H), 5.80 (q, J = 7.9 Hz, 1H), 2.55-2.51 (m, 2H), 2.43-2.34 (m, 1H), 2.33-2.22 (m, 2H), 2.10-2.00 (m, 2H), 1.94 (s, 2H), 1.57 (dq, J = 13.5, 6.8 Hz, 1H), 1.08-1.01 (m, 4H), 1.00 (s, 9H), 0.89 (s, 9H), 0.74 (dd, J = 6.7, 4.9 Hz, 6H). | | | | |

-continued

| Example | structure<br>$^1$H NMR | IUPAC name | substrate | RT | Mass |
|---|---|---|---|---|---|
| 87 | 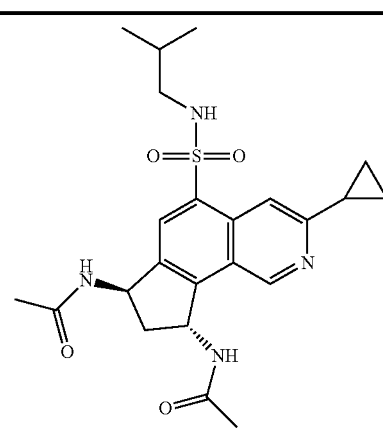<br>R,R and S,S | 1-ethyl-3-[trans-(7RS,9RS)-3-cyclopropyl-7-(ethylcarbamoylamino)-5-[(2-fluoro-2-methylpropyl)sulfamoyl]-8,9-dihydro-7H-cyclopenta[h]isoquinolin-9-yl]urea | acetyl chloride | 1.62 | 459 |
| | $^1$H NMR (400 MHz, DMSO-d6) $\delta_H$ 9.29 (d, J = 0.9 Hz, 1H), 8.54 (d, J = 8.9 Hz, 1H), 8.41 (d, J = 8.3 Hz, 1H), 8.36 (d, J = 0.9 Hz, 1H), 8.14 (t, J = 6.0 Hz, 1H), 8.06 (s, 1H), 6.01 (ddd, J = 9.5, 6.1, 4.0 Hz, 1H), 5.77 (q, J = 7.8 Hz, 1H), 2.55 (td, J = 6.5, 3.0 Hz, 2H), 2.38-2.24 (m, 3H), 1.92 (s, 3H), 1.81 (s, 3H), 1.63 (dt, J = 13.4, 6.7 Hz, 1H), 1.05 (d, J = 6.4 Hz, 4H), 0.78 (dd, J = 6.7, 3.0 Hz, 6H). | | | | |

Examples 88 and 89

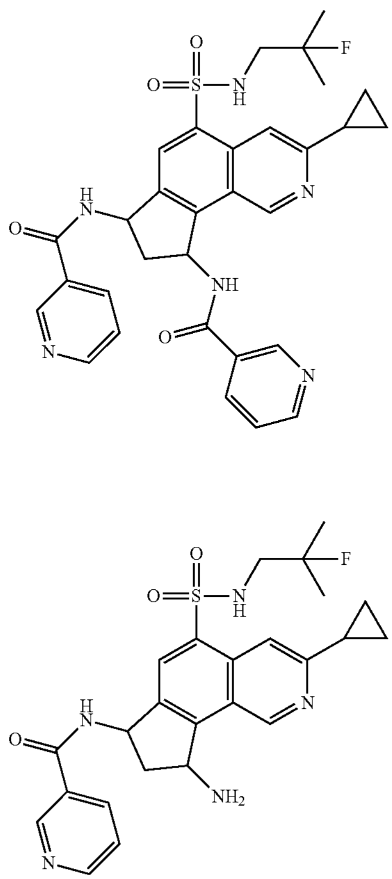

N-[3-cyclopropyl-5-[(2-fluoro-2-methylpropyl)sulfamoyl]-9-(pyridine-3-carbonylamino)-8,9-dihydro-7H-cyclopenta[h]isoquinolin-7-yl]pyridine-3-carboxamide (88)

N-[9-amino-3-cyclopropyl-5-[(2-fluoro-2-methylpropyl)sulfamoyl]-8,9-dihydro-7H-cyclopenta[h]isoquinolin-7-yl]pyridine-3-carboxamide (89)

To a solution of Intermediate 62 (120 mg, 0.258 mmol) in DCM (5 mL) at 0° C. was added diisopropylethylamine (150 mg, 1.16 mmol) and nicotinoyl chloride hydrochloride (45.9 mg, 0.258 mmol). The mixture was the stirred for 48 h (in the absence of the cooling bath). The reaction mixture was diluted with DCM and washed with water and then brine, passed through a phase separator cartridge and evaporated to leave a gum. The crude product was purified by flash chromatography eluting with a gradient of 1-50% MeOH in DCM to afford the title compound, Example 88 (22 mg, 14%) as an off-white solid; $\delta_H$ (300 MHz, MeOD-d4) 9.40-9.31 (m, 2H), 9.20 (d, J=8.4 Hz, 1H), 9.09 (dd, J=2.3, 0.9 Hz, 1H), 9.03 (dd, J=2.4, 0.9 Hz, 1H), 8.77-8.67 (m, 2H), 8.54-8.46 (m, 1H), 8.43 (d, J=0.9 Hz, 1H), 8.31-8.19 (m, 2H), 8.17 (s, 1H), 7.59-7.47 (m, 2H), 6.44-6.34 (m, 1H), 6.25-6.15 (m, 1H), 3.03-2.86 (m, 2H), 2.76-2.60 (m, 2H), 2.35-2.23 (m, 1H), 1.30-1.14 (m, 6H), 1.09-0.97 (m, 4H). LCMS [M+H]+ 603, RT 1.38 minutes (Method 11)

Later fractions from the column yielded Example 89 at ~60% purity. This material was purified by prep HPLC to give Example 89 (3 mg, 2%) as an off-white solid; $\delta_H$ (300 MHz, MeOD-d4) 9.51 (d, J=1.0 Hz, 1H), 9.05 (dd, J=2.3, 1.0 Hz, 1H), 8.72 (dd, J=4.9, 1.6 Hz, 1H), 8.44 (d, J=1.0 Hz, 1H), 8.36-8.27 (m, 2H), 7.58 (ddd, J=8.0, 5.0, 1.0 Hz, 1H), 6.14 (t, J=7.6 Hz, 1H), 5.21 (d, J=6.9 Hz, 1H), 3.13-2.91 (m, 2H), 2.73-2.51 (m, 2H), 2.39-2.28 (m, 1H), 1.32-1.20 (m, 6H), 0.90 (d, J=7.6 Hz, 4H) [4 NH protons not seen]. LCMS $[M+H]^+$ 498, RT 1.50 minutes (Method 15).

In Vitro Biochemical Assay

Protocol for preparation of IgE-Tb reagent 86 nmoles of IgE-Fc(N265Q, N371Q) (Young et al., 1995) at 172 μM in 100 mM $NaHCO_3$, pH 9.5 was added to 1 mg of LanthaScreen™ Amine Reactive Tb Chelate (ThermoFisher catalogue number PV3583) and incubated for 16 hours at 20° C. The material was then buffer exchanged into Phosphate Buffered Saline (being, 137 mM NaCl, 2.7 mM KCl, 10 mM $Na_2HPO_4$, 1.8 mM $K_2HPO_4$, pH 7.4) and the material quantified and the degree of Tb conjugation determined by measuring the absorption at 280 nm and 343 nm.

The integrity of the conjugated material was determined by analytical size exclusion chromatography on a S200 HR 10×300 column (GE Healthcare). Typical conjugation ratios were 4:1 Tb:IgE-Fc.

Young R J., Owens, R J., MacKay G A., Chan C M W., Shi J., Hide M., Francis D M., Henry A J., Sutton B J., and Gould H J (1995) Protein Engineering 8:193-199

Protocol for preparation of sFcεR1α-Y131A-AF488 reagent 400 nmoles FcεR1α (Y131A mutant) (Cook et al., 1997) at 400 μM in 100 mM NaOAc pH 5.5 was reacted with 1 mM final concentration sodium periodate (in 100 mM NaOAc, pH 5.5) for 60 minutes at 22° C. Oxidation was quenched with the addition of 40 μL of ethanediol and incubation for 60 minutes at 22° C. The protein was buffer exchanged in to conjugation buffer (50 mM $NaHCO_3$, 150 mM NaCl, pH 9.5) and concentrated to 750 μM. 175 nmoles of protein was added to 1 mg of Alexa Fluor™ 488 hydrazide (Invitrogen) and incubated for 16 hours at 22° C. Sodium cyanoborohydride (at 100 mM in conjugation buffer) was added to a final concentration of 1 mM and incubated for 60 minutes on ice. The protein was buffer exchanged into Phosphate Buffered Saline (being, 137 mM NaCl, 2.7 mM KCl, 10 mM $Na_2HPO_4$, 1.8 mM $K_2HPO_4$, pH 7.4) and the material quantified and the degree of Alexa Fluor™ 488 conjugation determined by measuring the absorption at 280 nm and 495 nm.

The integrity of the conjugated material was determined by analytical size exclusion chromatography on a S200 HR 10×300 column (GE Healthcare). Typical conjugation ratios were 2:1 Alexa Fluor™ 488: sFcεR1α Cook J P D., Henry A J., McDonnell J M., Owens R J., Sutton B J., and Gould H J (1997) Biochemistry 36:15579-15588

Protocol for preparation of sFcεR1α-AF488 reagent

To a solution of 1.32 pmoles WT FcεR1a, at 377 μM, in 100 mM NaOAc pH 5.5, was slowly added 50 mM sodium periodate (70 μL) in 100 mM NaOAc, pH 5.5, with gentle mixing, to give a final concentration of 1 mM. The solution was incubated for 60 minutes at 22° C. with gentle mixing. A second aliquot of 50 mM sodium periodate (70 μL) was added and the solution incubated for 60 minutes at 22° C. with gentle mixing. Oxidation was stopped by the slow addition of ethanediol (151.4 μL), with gentle mixing, to give a final concentration of 4% v/v. The solution was incubated with gentle mixing for 60 minutes at 22° C. The protein was buffer exchanged, using PD 10 columns (GE Healthcare), into conjugation buffer (50 mM $NaHCO_3$, 150 mM NaCl, pH 9.5) and concentrated using an Amicon Ultra 15 (10 kDa cutoff, Merck) to 1.13 mM.

175 nmoles of protein was added to 1 mg of Alexa Fluor™ 488 hydrazide (Invitrogen) and incubated for 18 hours at 22° C. with gentle mixing. The mixture was cooled on ice, and ice-cold sodium cyanoborohydride (at 100 mM in conjugation buffer) added, to give a final concentration of 1 mM and incubated for 60 minutes on ice. The protein was buffer exchanged into Phosphate Buffered Saline (being, 137 mM NaCl, 2.7 mM KCl, 10 mM $Na_2HPO_4$, 1.8 mM $K_2HPO_4$, pH 7.4) using NAP-10 columns (GE Healthcare). The material was quantified, and the degree of Alexa Fluor™ 488 conjugation determined by measuring the absorption at 280 nm and 497 nm. Typical conjugation ratios were 2:1 Alexa Fluor™ 488: sFcεR1α.

The aim was to measure binding of IgE-Tb to receptor, and the inhibition thereof by compounds, using an in vitro Fluorescence Resonance Energy Transfer (FRET) Assay.

Reagents

FRET reagents used were IgE labelled with Terbium (FRET donor), soluble IgE receptor FcεR1a labelled with Alexa Fluor™ 488 (FRET acceptor) and soluble IgE receptor FcεR1a with a Y131A mutation, labelled with Alexa Fluor™ 488 (FRET acceptor). Unlabelled FcεR1a was also used to generate a background control. The assay buffer consisted of 20 mM Tris pH7.2, 150 mM NaCl, and 0.002% Tween, 1% DMSO.

Assay Reaction

For examples 16 and 89, the assay was conducted according to the following: Each assay reaction was conducted in a volume of 25 μl in a 384-well half-volume plate. 10 point compound serial dilutions (3-fold) were generated in DMSO at a concentration of ×50 that of the final assay concentration (FAC). Compound solutions were then prepared by IgE-Tb diluting 10-fold in assay buffer. For the assay, 5 μl of diluted compound was added to 10 μl of IgE-Tb, followed by addition of 10 μl FcεR1a-Y131A-AF488. FRET reagents FACs were 5 nM IgE-Tb, 25 nM FcεR1α-Y131A-AF488. Usually the top FAC of compound in the assay was 10 μM. The final DMSO concentration was 2%. The minimum signal (MIN) was measured by adding 5 μl unlabelled FcεR1a at 1 μM (FAC=200 nM) to the FRET reagents. The maximum FRET signal (MAX) was measured in wells containing FRET reagents but no compound.

The assay was incubated for 2 hours at room temperature, protected from light and evaporation, and with gentle agitation.

FRET Measurement

Measurement of FRET for each well was carried out by exciting at 330 nm and measuring emission at 495/520 nm using an Envision plate reader (Perkin Elmer). FRET ratio was calculated as follows:

$$\text{Emission at } 520/\text{Emission at } 495\times 1000.$$

The FRET ratio was used for the data analysis.

Data Analysis

Z' was calculated as follows (6=standard deviation and p=mean):

$$1-((3\times\sigma_{MAX})+(3\times\sigma_{MIN}))/(\mu_{MAX}-\mu_{MIN})$$

Z' above 0.5 was considered a good assay.

Background signal (MIN) was subtracted from all wells. Using the background subtracted values, the percent inhibition by compound in each test-well was calculated as follows:

$$100-\text{Test-well } FRET \text{ ratio/MAX } FRET \text{ ratio}\times 100.$$

Percent inhibition was plotted against compound concentration. IC50 values for each compound were determined using four parameter logistic fit model using the XLFIT5 software package.

For examples 1-15, 36-47, 53-62, and 64-88, the assay was conducted according to the following: Each assay reaction was conducted in a volume of 25 μl in a 384-well half-volume plate. 10 point compound serial dilutions (3-fold) were generated in DMSO at a concentration of ×50 that of the final assay concentration (FAC). Compound solutions were then prepared by diluting 10-fold in assay buffer. For the assay, 51 of diluted compound was added to 101 of IgE-Tb and incubated for 30 minutes before the addition of 101 sFcεR1α-Y131A-AF488. FRET reagents FACs were 5 nM IgE-Tb, 25 nM sFcεR1α-Y131A-AF488. Usually the top FAC of compound in the assay was 10 μM. The final DMSO concentration was 2%. The minimum signal (MIN) was measured by adding 51.11 unlabelled sFcεR1α at 1 μM (FAC=200 nM) to the FRET reagents. The maximum FRET signal (MAX) was measured in wells containing FRET reagents but no compound.

The assay was incubated for 18 hours at room temperature, protected from light and evaporation, and with gentle agitation.

FRET measurement

Measurement of FRET for each well was carried out by exciting at 337 nm and measuring emission at 490/520 nm using a PHERAstar FSX plate reader (BMG Labtech). FRET ratio was calculated as follows:

$$\text{Emission at 520/Emission at } 490 \times 1000.$$

The FRET ratio was used for the data analysis.

Data Analysis

Z' was calculated as follows (6=standard deviation and p=mean):

$$1-((3\times\sigma_{MAX})+(3\times\sigma_{MIN}))/(\mu_{MAX}-\mu_{MIN})$$

Z' above 0.5 was considered a good assay.

Background signal (MIN) was subtracted from all wells. Using the background subtracted values, the percent inhibition by compound in each test-well was calculated as follows:

$$100-\text{Test-well } FRET \text{ ratio/MAX } FRET \text{ ratio} \times 100.$$

Percent inhibition was plotted against compound concentration. IC50 values for each compound were determined using four parameter logistic fit model using the XLFIT5 software package.

For examples 17-35, 48-52 and 63, the assay was conducted according to the following: Each assay reaction was conducted in a volume of 25 μl in a 384-well half-volume plate. 10 point compound serial dilutions (3-fold) were generated in DMSO at a concentration of ×50 that of the final assay concentration (FAC). Compound solutions were then prepared by diluting 10-fold in assay buffer. For the assay, 5 μl of diluted compound was added to 10 μl of IgE-Tb, followed by addition of 10 μl sFcεR1α-AF488. FRET reagents FACs were 0.75 nM IgE-Tb, 0.9 nM sFcεR1α-AF488. Usually the top FAC of compound in the assay was 10 μM. The final DMSO concentration was 2%. The minimum signal (MIN) was measured by adding 5 μl unlabelled sFcεR1α at 1 μM (FAC=200 nM) to the FRET reagents. The maximum FRET signal (MAX) was measured in wells containing FRET reagents but no compound.

The assay was incubated for 18 hours at room temperature, protected from light and evaporation, and with gentle agitation.

FRET Measurement

Measurement of FRET for each well was carried out by exciting at 337 nm and measuring emission at 490/520 nm using a PHERAstar FSX plate reader (BMG Labtech). FRET ratio was calculated as follows:

$$\text{Emission at 520/Emission at } 490 \times 1000.$$

The FRET ratio was used for the data analysis.

Data Analysis

Z' was calculated as follows (6=standard deviation and μ=mean):

$$1-((3\times\sigma_{MAX})+(3\times\sigma_{MIN}))/(\mu_{MAX}-\mu_{MIN})$$

Z' above 0.5 was considered a good assay.

Background signal (MIN) was subtracted from all wells. Using the background subtracted values, the percent inhibition by compound in each test-well was calculated as follows:

$$100-\text{Test-well } FRET \text{ ratio/MAX } FRET \text{ ratio} \times 100.$$

Percent inhibition was plotted against compound concentration. IC50 values for each compound were determined using four parameter logistic fit model using the XLFIT5 software package Compounds tested in the above assays show IC50 values ranging from 4n M to 1975 nM.

The table below shows the range of IC50 values for each example:

| Example Number | FRET $IC_{50}$ range |
|---|---|
| 4, 18, 38, 39, 40, 41, 42, 43, 46, 59, 64, 66, 70, 71, 79, 80, 81 | 1-10 nanomolar |
| 1, 5, 6, 7, 8, 10, 14, 15, 17, 19, 20, 21, 22, 23, 24, 25, 26, 30, 31, 32, 44, 48, 53, 54, 55, 56, 58, 60, 61, 62, 65, 67, 72, 82, 83, 84 | 10-50 nanomolar |
| 11, 13, 17, 27, 28, 33, 34, 45, 47, 49, 57, 63, 74, 85 | 50-100 nanomolar |
| 2, 3, 9, 12, 16, 36, 37, 68, 69, 73, 75, 76, 77, 78, 86, 87, 88, 89 | 0.1-2 micromolar |

The invention claimed is:

1. A compound of general formula (I) or a pharmaceutically acceptable salt thereof, (I)

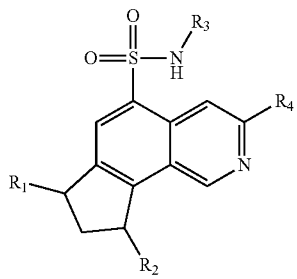

Wherein:

R1 represents:

Hydroxy;

Amino;

—NH—C(O)—$Ra^1$;

—NH—C(O)—NH—$Rb^1$;

—NH—C(O)—C1-6-alkanediyl-C(O)—C1-6-alkoxy optionally substituted with one or more aryl substituted with one or more halogen, —OH, or C1-6-alkyl;

—NH—C(O)—C1-6-alkanediylC(O)-aryl optionally substituted with one or more hydroxy; halogen; or C1-6-alkyl;

—NH—C(O)—C1-6-alkanediyl-NHC(O)-aryl optionally substituted with one or more hydroxy; halogen; or C1-6-alkyl;

—NH—C(O)—C1-6-alkanediyl-aryloxy optionally substituted with one or more hydroxy; halogen; or C1-6-alkyl;

—NH—C(O)—NH—C(O)O—C1-6-alkyl;

—NH-Heteroaryl optionally substituted with one or more Halogen; C1-6-alkyl, C1-6-alkoxy; cyano; or heteroaryl;

—NH—C(S)—NH-$Rc^1$;

—NH-Aryl optionally substituted with one or more Halogen; C1-6-alkyl, C1-6-alkoxy; cyano; or heteroaryl;

—NH—C(O)O-$Rd^1$;

—NH—C(N—CN)—NH—C1-6-alkyl; or

Heteroaryl optionally substituted with one or more C1-6-alkyl, C1-6-alkylamino; or heteroarylamino;

wherein $Ra^1$ represents

C1-6-alkyl optionally substituted with one or more Aryl or Heteroaryl, each of which is optionally substituted with Halogen; C1-6-alkoxy; or cyano;

Aryl optionally substituted with one or more Halogen; C1-6-alkyl, C1-6-alkoxy; or C1-6-akylamino;

Heteroaryl optionally substituted with one or more Halogen; C1-6-alkyl, C1-6-alkoxy; cyano; or heterocycloalkyl;

—C2-6-alkenediyl-aryl optionally substituted with one or more C1-6-alkyl; or Halogen;

—R1'C(O)OR1" group, wherein R1" is alkyl and R1' is alkanediyl;

C3-8-cycloalkyl optionally substituted with one or more Halogen; C1-6-alkyl, C1-6-alkoxy; cyano; or C3-8-heterocycloalkyl optionally substituted with one or more Halogen; C1-6-alkyl, C1-6-alkoxy; or cyano;

$Rb^1$ represents

C1-6-alkyl optionally substituted with aryl optionally substituted with one or more Halogen, C1-6-alkoxy; heteroaryl which is optionally substituted with one or more Halogen; C1-6-alkyl; or C1-6-alkoxy;

C3-12-cycloalkyloptionally substituted with one or more C1-6-alkyl group, or aryl;

Aryl optionally substituted with one or more cyano;

C2-6-alkenediyl-aryl optionally substituted with one or more Halogen; C1-6-alkyl; —OH; Aryl substituted with one or more Halogen; C1-6-alkyl; or —OH;

Heterorary1 optionally substituted with one or more Halogen, C1-6-alkyl, or C1-6-alkoxy; or Heterocycloalkyl optionally substituted with one or more Halogen; C1-C6-alkoxy; cyano; or Amino;

$Rc^1$ represents

C1-6-alkyl; or

Heteroaryl;

$Rd^1$ represents:

C1-6-alkyl;

R2 represents:

Hydroxy;

—NH—C(O)O—C1-6-Alkyl;

—NH—C(S)—NH—$Ra^2$;

—NH—C(O)—NH—$Rb^2$;

—NH-Aryl optionally substituted with one or more C1-6-alkoxy; C1-6-Alkylamino; heteroarylamino;

—NH—C1-6-Alkyl optionally substituted with one or more C1-6-alkyl; C1-6-alkoxy; cyano; aryl; heteroaryl; C(O)O—C1-6-Alkyl group; C1-6-Alkylamino group; said substituent being optionally substituted with one or more hydroxy; halogen; oxo;

Heteroaryl optionally substituted with one or more heteroaryl, C1-6-alkylamino or heteroarylamino; said heteroaryl or heteroarylamino being optionally substituted with one or more group chosen amongst amino; C1-6-alkyl; C1-6-alkylamino; heteroarylamino;

—NH-Heteroaryl optionally substituted with one or more Halogen; C1-6-alkyl, C1-6-alkoxy; cyano; heteroaryl; C(O)OH; C(O)O—C1-6-Alkyl group; C1-6-Alkylamino group;

Aryl-C1-6-Alkylamino;

—C1-6-alkylamino;

—NH—C(O)—C1-6-alkyl;

—NH—CO-$Rc^2$;

—NH—C(O)—C2-6-alkenediyl-C(O)O—C1-6-Alkyl;

—NH—C(O)—C2-6-alkenediyl-aryl optionally substituted with one or more hydroxy. C1-6-alkyl;

Halogen;

—NH—C(O)—C1-6-alkanediyl-heteroaryl optionally substituted with one or more oxo group;

—NH—C(O)—C1-6-alkanediyl-heterocycloalkyl optionally substituted with one or more oxo group;

—$NHSO_2$—C1-6-alkyl;

—$NHSO_2$—Heteroaryl optionally substituted with one or more Halogen; C1-6-alkyl, C1-6-alkoxy;

C(O)OH group;

—NH—C(S)—NH—C1-6-Alkyl;

—$NHSO_2$—C1-6-alkoxy optionally substituted with one or more Halogen group;

—NH—C(N—CN)—NH—C1-6-alkyl; or

Amino group;

$Ra^2$ represents

Heteroaryl; or

C1-6-alkyl;

$Rb^2$ represents

C1-6-alkyl optionally substituted with one or more Aryl; alkoxy-Aryl; or heteroaryl optionally substituted with one or more C1-6-alkyl;

Heteroaryl optionally substituted with one or more Halogen; C1-6-alkyl, C1-6-alkoxy; or cyano; or Cycloalkyl optionally substituted with one or more Halogen; C1-6-alkyl, C1-6-alkoxy; cyano; or aryl;

C1-6-alkanediyl-C(O)O—C1-6-alkyl;

Heterocycloalkyl; or

Aryl optionally substituted with one or more Halogen; C1-6-alkyl, C1-6-alkoxy; cyano; or C1-6-alkyl-C(O)O—C1-6-alkyl;

$Rc^2$ represents

C1-6-alkyl;

C3-8-cycloalkyl;

C3-8-heterocycloalkyl;

Aryl optionally substituted with one or more C1-6-alky; or C1-6-alkylamino;

Heteroaryl optionally substituted with one or more Halogen; C1-6-alkyl, C1-6-alkoxy; cyano; heterocycloalkyl; Aryl; or amino;

C2-6-alkenediyl-Aryl optionally substituted with one or more Halogen; C1-6-alkyl; or —OH;

C2-6-alkanediyl-Heterocyloalkyl optionally substituted with one or more C1-6-alkyl; or —OH;

C2-6-alkanediyl-C1-6-alkoxy group optionally substituted with one oxo group;

R3 represents a group chosen amongst:

C1-6-alkyl optionally substituted with one or more independently selected $R3^a$;

C1-3-alkanediyl-C3-6-cycloalkyl optionally substituted with one or more independently selected $R3^a$;

C1-3-alkanediyl-C3-6-heterocycloalkyl optionally substituted with one or more independently selected $R3^a$;

C3-6-heterocycloalkyl optionally substituted with one or more independently selected R3a; or C3-6-cycloalkyl optionally substituted with one or more independently selected $R3^a$;

$R3^a$ represents hydrogen Halogen, C1-2-alkyl; hydroxy; or C1-2-alkoxy;

R4 represents:

C3-6-cycloalkyl optionally substituted with one or more independently selected $R4^a$ group; C1-6-alkanediyl-C3-6-cycloalkyl optionally substituted with one or more independently selected $R4^a$ group; or C1-6-alkanediyl-C3-6-heterocycloalkyl optionally substituted with one or more independently selected $R4^a$ group; and $R4^a$ represents a group chosen amongst hydroxy; Halogen; C1-2-alkyl.

2. A compound according to claim 1 wherein R4 represents cyclopropyl optionally substituted with one or more groups independently selected from hydroxy, Chloro, Fluoro, Bromo, and methyl.

3. A compound according to claim 1 wherein R4 represents cyclopropyl.

4. A compound according to claim 1 wherein R1 and R2 represent independently from each other —NH—CO—$Ra^1$ and $Ra^1$ represents Heteroaryl optionally substituted with one or more Halogen; C1-6-alkyl, C1-6-alkoxy; cyano; or heterocycloalkyl; or $Ra^1$ represents —NH-heteroaryl optionally substituted with one or more Halogen; C1-6-alkyl, C1-6-alkoxy; cyano; heterocycloalkyl; or aryl.

5. A compound according to claim 1 wherein R1 represents:

hydroxy; pyridine-carbonylamino; ethylcarbamoylamino; (methoxyphenyl)methylcarbamoylamino; [(bromphenyl) methyl]carbamoylamino;

naphthalenylcarbamoylamino; (methyl-oxazolyl)methyl] carbamoylamino; ethoxycarbonyl-carbamoylamino; [(methoxyphenyl)ethyl]carbonylamino; (cyclopropylethyl)carbamoylamino; (methyl)cyclopropyl]carbamoylamino; (benzyl)carbamoylamino; (phenyl-cyclopropyl)carbamoylamino; (chromanyl)carbamoylamino; (chlorophenyl)propenoyl]amino; (methoxypyridine-carbonyl)amino; [(methoxy-oxo-propanoyl)amino]; (benzamidoacetyl)amino; (chloro-methoxy-thiophene-carbonyl)amino; (ethoxy-oxo-propanoyl)amino; methylbutanoylamino; [(chlorophenoxy)acetyl]amino; (methoxypyridinyl)amino; amino; benzimidazolyl-amino; ethylcarbamothioylamino; (pyridinyl-triazolyl) amino; (ethyl-triazolyl)amino; (ethylamino)-triazolyl; ethylcarbamoylamino; (methyl-oxadiazolyl)anilino; tert-butoxycarbonylamino; [N'-cyano-N-ethyl-carbamimidoyl]amino; pyridin-3-yl-carbamoylamino; propan-2-yl-carbamoylamino; (5-methylpyridine-3-carbonyl) amino; (6-morpholin-4-ylpyridine-3-carbonyl)amino; benzamido; [(dimethylamino)benzoyl]amino; or Dimethylbutanoylamino.

6. A compound according to claim 1 wherein R1 represents: Hydroxy; pyridine-3-carbonylamino; ethylcarbamoylamino; (4-methoxyphenyl)methylcarbamoylamino; (3-cyanophenyl)carbamoylamino; [(4-bromphenyl)methyl] carbamoylamino; naphthalen-1-ylcarbamoylamino; [(5-methyl-1,2-oxazol-3-yl)methyl]carbamoylamino; ethoxycarbonyl-carbamoylamino; [(1R)-1-(3-methoxyphenyl)ethyl]carbonylamino; (1-cyclopropylethylcarbamoylamino); 2-(methyl)cyclopropyl]carbamoylamino; (1-benzyl)carbamoylamino; (2-phenyl-cyclopropyl) carbamoylamino; (chroman-3-yl)carbamoylamino; (E)-3-(2-chlorophenyl)prop-2-enoyl]amino; (6-methoxypyridine-3-carbonyl)amino; [(3-methoxy-3-oxo-propanoyl)amino]; (2-benzamidoacetyl)amino; (5-chloro-4-methoxy-thiophene-3-carbonyl)amino; (3-ethoxy-3-oxo-propanoyl) amino; 2-methylbutanoylamino; [2-(4-chlorophenoxy) acetyl]amino; (5-methoxypyridin-3-yl)amino; amino; 1H-benzimidazol-2-ylamino; ethylcarbamothioylamino; (4-pyridin-3-yl-1,2,4-triazol-3-yl)amino; 3-(ethylamino)-1,2,4-triazol-4-yl; 3-(5-methyl-1,3,4-oxadiazol-2-yl)anilino; tert-butoxycarbonylamino; [(Z)—N'-cyano-N-ethyl-carbamimidoyl]amino; propan-2-ylcarbamoylamino; pyridin-3-ylcarbamothioylamino; (5-methylpyridine-3-carbonyl) amino; 6-morpholin-4-ylpyridine-3-carbonyl)amino; benzamido; [4-(dimethylamino)benzoyl]amino; or 3,3-dimethylbutanoylamino.

7. A compound according to claim 1 wherein R2 represents: tert-butoxycarbonyl-amino; amino; pyridylcarbamothioylamino; ethylcarbamoylamino; pyridinyl-amino; (pyridinyl-triazolyl)amino; (pyridinyl-amino)-triazolyl; (ethyl-triazolyl)amino; benzylamino; propylamino; methylpropanoylamino; hydroxy; ethylcarbamoylamino; isoquinolinyl-amino; (methoxypyridinyl)amino; (pyridinyl)carbonylamino; benzimidazolylamino; [(phenyl)-oxazolyl] carbonylamino; quinoxaline-carbonylamino; [(hydroxyphenyl)propenoyl]amino; pyrido-pyrazine-carbonylamino; benzoxazole-carbonylamino; [ethoxy-oxo-butenoyl]amino; (benzimidazolyl)propanoylamino; (oxopyridinyl)propanoylamino; methoxy-benzofuran-carbonyl)amino; (oxopyrrolidinyl)propanoylamino; [(ethoxy-carbonyl-pyridyl)amino]; (methoxyanilino); (cyano-pyridyl)amino; [(methyl-pyridazinyl)amino]; quinolinyl-amino; (methyl-oxazolyl)methyl-carbamoyl-amino; (phenylcyclopropyl)carbamoylamino; [(tert-butoxymethyl-oxo-ethyl)carbamoylamino]; dihydro-2H-chromenylcarbamoylamino; [(methoxyphenyl)ethylcarbamoylamino]; oxanylcarbamoylamino; (chloro-methylphenyl)carbamoylamino; methanesulfonamido; methylpropylsulfonylamino; pyridinylsulfonylamino; [(carboxypyridyl)amino]; pyridylcarbamoylamino; methoxy-pyridinyl)amino; ethyl-carbamothioyl-amino; (pyridinyl-triazolyl)amino; (methoxy-pyridinyl)amino; (ethyl-triazolyl)amino(ethylamino)-triazolyl; (methyl-oxadiazolyl)anilino; trichloroethoxysulfonylamino; [(Z)—N'-cyano-N-ethyl-carbamimidoyl]amino; pyridinylcarbamoylamino; propanylcarbamoylamino; pyridinylcarbamothioylamino; methylpyridinecarbonyl)amino; (morpholinylpyridinecarbonyl) amino; Benzamido; [(dimethylamino)benzoyl]amino; or dimethylbutanoylamino.

8. A compound according to claim 1 wherein R2 represents: tert-butoxycarbonyl-amino; amino; 3-pyridylcarbamothioylamino; ethylcarbamoylamino; pyridine-3-yl-amino; (4-pyridin-3-yl-1,2,4-triazol-3-yl)amino; 3-(pyridin-3-ylamino)-1,2,4-triazol-4-yl; (4-ethyl-1,2,4-triazol-3-yl) amino; benzylamino; propylamino; 2-methylpropanoylamino; hydroxy; ethylcarbamoylamino; isoquinolin-4-ylamino; (5-methoxypyridin-3-yl)amino; (pyridine-3-yl)carbonylamino; 1H-benzimidazol-2-ylamino; [3-(phenyl)-1,2-oxazol-5-yl]carbonylamino; quinoxaline-6-carbonylamino; 3-(4-hydroxyphenyl)prop-2-enoyl]amino; pyrido[2,3-b]pyrazine-7-carbonylamino; 1,3-benzoxazole-2-carbonylamino; [(E)-4-ethoxy-4-oxo-but-2-enoyl]amino; 3-(benzimidazol-1-yl)propanoylamino; 3-(2-oxopyridin-1-yl)propanoylamino; 4-methoxy-1-benzofuran-2-carbonyl)amino; 3-(2-oxopyrrolidin-1-yl) propanoylamino; [(5-ethoxycarbonyl-3-pyridyl)amino]; (2-methoxyanilino); (4-cyano-2-pyridyl)amino; [(6-methylpyridazin-3-yl)amino]; quinolin-4-ylamino; (5-methyl-1,2-oxazol-3-yl)methylcarbamoylamino; (2-phenylcyclopropyl)carbamoylamino; [(2-tert-butoxy-1-methyl-2-oxo-ethyl)carbamoylamino]; 3,4-dihydro-2H-chromen-3-ylcarbamoylamino; [1-(3-methoxyphenyl) ethylcarbamoylamino]; oxan-4-ylcarbamoylamino; (2-chloro-6-methylphenyl)carbamoylamino; methanesulfonamido; 2-methylpropylsulfonylamino; pyridin-3-ylsulfonylamino; [(5-carboxy-3-pyridyl)amino]; 3-pyridylcarbamoylamino; 5-methoxypyridin-3-yl)amino; ethylcarbamothioylamino; (4-pyridin-3-yl-1,2,4-triazol-3-yl)amino; (5-methoxypyridin-3-yl)amino; (4-ethyl-1,2,4-triazol-3-yl)amino; 3-(ethylamino)-1,2,4-triazol-4-yl; 3-(5-methyl-1,3,4-oxadiazol-2-yl)anilino; 2,2,2-trichloroethoxysulfonylamino; [(Z)—N'-cyano-N-ethyl-carbamimidoyl]amino; pyridin-3-ylcarbamoylamino; propan-2-ylcarbamoylamino; pyridin-3-ylcarbamothioylamino; 5-methylpyridine-3-carbonyl)amino; (6-morpholin-4-ylpyridine-3-carbonyl)amino; Benzamido; [4-(dimethylamino)benzoyl]amino; or 3,3-dimethylbutanoylamino.

9. A compound according to claim 1 which is tert-butyl N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]carbamate;

tert-butyl N-[cis-(7RS,9SR)-3-cyclopropyl-5-(2-methylpropylsulfamoyl)-7-(pyridine-3-carbonylamino)-8,9-dihydro-7H-cyclopenta[h]isoquinolin-9-yl]carbamate;

N-[trans-(7RS,9RS)-9-amino-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(pyridin-3-ylcarbamothioylamino)-8,9-dihydro-7H-cyclopenta[h]isoquinolin-7-yl]pyridine-3-carboxamide;

N-[trans-(7RS,9RS)-3-cyclopropyl-9-(ethylcarbamoylamino)-5-(2-methylpropylsulfamoyl)-8,9-dihydro-7H-cyclopenta[h]isoquinolin-7-yl]pyridine-3-carboxamide;

N-[cis-(7RS,9SR)-3-cyclopropyl-5-(2-methylpropylsulfamoyl)-9-(pyridin-3-ylamino)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(pyridin-3-ylamino)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[(4-pyridin-3-yl-1,2,4-triazol-3-yl)amino]-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[3-(pyridin-3-ylamino)-1,2,4-triazol-4-yl]-8,9-dihydro-7H-cyclopenta[h]isoquinolin-7-yl]pyridine-3-carboxamide;

N-[trans-(7RS,9RS)-3-cyclopropyl-9-[(4-ethyl-1,2,4-triazol-3-yl)amino]-5-(2-methylpropylsulfamoyl)-8,9-dihydro-7H-cyclopenta[h]isoquinolin-7-yl]pyridine-3-carboxamide;

N-[trans-(7RS,9RS)-9-(benzylamino)-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(propylamino)-8,9-dihydro-7H-cyclopenta[h]isoquinolin-7-yl]pyridine-3-carboxamide;

N-[trans-(7RS,9RS)-3-cyclopropyl-9-(2-methylpropanoylamino)-5-(2-methylpropylsulfamoyl)-8,9-dihydro-7H-cyclopenta[h]isoquinolin-7-yl]pyridine-3-carboxamide;

1-ethyl-3-[trans-(7RS,9RS)-3-cyclopropyl-9-hydroxy-5-(2-methylpropylsulfamoyl)-8,9-dihydro-7H-cyclopenta[h]isoquinolin-7-yl]urea;

1-ethyl-3-[cis-(7RS,9SR)-3-cyclopropyl-9-hydroxy-5-(2-methylpropylsulfamoyl)-8,9-dihydro-7H-cyclopenta[h]isoquinolin-7-yl]urea 1-ethyl-3-[trans-(7RS,9RS)-3-cyclopropyl-7-hydroxy-5-(2-methylpropylsulfamoyl)-8,9-dihydro-7H-cyclopenta[h]isoquinolin-9-yl]urea;

N-[cis-(7RS,9SR)-3-cyclopropyl-9-(isoquinolin-4-ylamino)-5-(2-methylpropylsulfamoyl)-8,9-dihydro-7H-cyclopenta[h]isoquinolin-7-yl]pyridine-3-carboxamide;

1-[(4-methoxyphenyl)methyl]-3-[trans-(7RS,9RS)-3-cyclopropyl-9-[(5-methoxypyridin-3-yl)amino]-5-(2-methylpropylsulfamoyl)-8,9-dihydro-7H-cyclopenta[h]isoquinolin-7-yl]urea;

N-[trans-(7RS,9RS)-7-[(3-cyanophenyl)carbamoylamino]-3-cyclopropyl-5-(2-methylpropylsulfamoyl)-8,9-dihydro-7H-cyclopenta[h]isoquinolin-9-yl]pyridine-3-carboxamide;

N-[trans-(7RS,9RS)-7-[(4-bromophenyl)methylcarbamoylamino]-3-cyclopropyl-5-(2-methylpropylsulfamoyl)-8,9-dihydro-7H-cyclopenta[h]isoquinolin-9-yl]pyridine-3-carboxamide;

N-[trans-(7RS,9RS)-3-cyclopropyl-5-(2-methylpropylsulfamoyl)-7-(naphthalen-1-ylcarbamoylamino)-8,9-dihydro-7H-cyclopenta[h]isoquinolin-9-yl]pyridine-3-carboxamide;

1-[(5-methyl-1,2-oxazol-3-yl)methyl]-3-[trans-(7RS,9RS)-9-(1H-benzimidazol-2-ylamino)-3-cyclopropyl- 5-(2-methylpropylsulfamoyl)-8,9-dihydro-7H-cyclopenta[h]isoquinolin-7-yl]urea;

Ethyl N-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]carbamoyl]carbamate;

1-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]-3-[rac-(1S)-1-(3-methoxyphenyl)ethyl]urea;

1-(1-cyclopropylethyl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

1-(2-methylcyclopropyl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

1-benzyl-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

1-(2-phenylcyclopropyl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

1-(3,4-dihydro-2H-chromen-3-yl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

N-[trans-(7RS,9RS)-3-cyclopropyl-5-(2-methylpropylsulfamoyl)-7-[[rac-(E)-3-(2-chlorophenyl)prop-2-enoyl]amino]-8,9-dihydro-7H-cyclopenta[h]isoquinolin-9-yl]pyridine-3-carboxamide;

6-methoxy-N-[trans-(7RS,9RS)-3-cyclopropyl-5-(2-methylpropylsulfamoyl)-9-(pyridine-3-carbonylamino)-8,9-dihydro-7H-cyclopenta[h]isoquinolin-7-yl]pyridine-3-carboxamide;

methyl 3-oxo-3-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]amino]propanoate N-[2-oxo-2-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]amino]ethyl]benzamide;

5-chloro-4-methoxy-N-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]thiophene-3-carboxamide ethyl 3-oxo-3-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]amino]propanoate;

N-[cis-(7RS,9SR)-3-cyclopropyl-7-(2-methylbutanoylamino)-5-(2-methylpropylsulfamoyl)-8,9-dihydro-7H-cyclopenta[h]isoquinolin-9-yl]pyridine-3-carboxamide;

N-[cis-(7RS,9SR)-7-[[2-(4-chlorophenoxy)acetyl]amino]-3-cyclopropyl-5-(2-methylpropylsulfamoyl)-8,9-dihydro-7H-cyclopenta[h]isoquinolin-9-yl]pyridine-3-carboxamide;

3-phenyl-N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]-1,2-oxazole-5-carboxamide;

N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]quinoxaline-6-carboxamide;

N-[trans-(7RS,9RS)-3-cyclopropyl-5-(2-methylpropylsulfamoyl)-9-[[rac-(E)-3-(4-hydroxyphenyl)prop-2-enoyl]amino]-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]pyrido[2,3-b]pyrazine-7-carboxamide;

N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]-1,3-benzoxazole-2-carboxamide;

ethyl rac-(E)-4-oxo-4-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]amino]but-2-enoate;

N-[trans-(7RS,9RS)-9-[3-(benzimidazol-1-yl)propanoylamino]-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[3-(2-oxopyridin-1-yl)propanoylamino]-8,9-dihydro-7H-cyclopenta[h]isoquinolin-7-yl]pyridine-3-carboxamide;

N-[trans-(7RS,9RS)-3-cyclopropyl-9-[(4-methoxy-1-benzofuran-2-carbonyl)amino]-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[3-(2-oxopyrrolidin-1-yl)propanoylamino]-8,9-dihydro-7H-cyclopenta[h]isoquinolin-7-yl]pyridine-3-carboxamide;

ethyl 5-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]amino]pyridine-3-carboxylate;

N-[trans-(7RS,9RS)-3-cyclopropyl-9-(2-methoxyanilino)-5-(2-methylpropylsulfamoyl)-8,9-dihydro-7H-cyclopenta[h]isoquinolin-7-yl]pyridine-3-carboxamide;

N-[trans-(7RS,9RS)-9-[(4-cyanopyridin-2-yl)amino]-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[(6-methylpyridazin-3-yl)amino]-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(quinolin-4-ylamino)-8,9-dihydro-7H-cyclopenta[h]isoquinolin-7-yl]pyridine-3-carboxamide;

N-[trans-(7RS,9RS)-3-cyclopropyl-9-[(5-methyl-1,2-oxazol-3-yl)methylcarbamoylamino]-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[(2-phenylcyclopropyl)carbamoylamino]-8,9-dihydro-7H-cyclopenta[h]isoquinolin-7-yl]pyridine-3-carboxamide;

tert-butyl 2-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]carbamoylamino]propanoate;

N-[trans-(7RS,9RS)-3-cyclopropyl-9-(3,4-dihydro-2H-chromen-3-ylcarbamoylamino)-5-(2-methylpropylsulfamoyl)-8,9-dihydro-7H-cyclopenta[h]isoquinolin-7-yl]pyridine-3-carboxamide;

N-[trans-(7SR,9SR)-3-cyclopropyl-5-(2-methylpropylsulfamoyl)-9-[[rac-(1R)-1-(3-methoxyphenyl)ethyl]carbamoylamino]-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(oxan-4-ylcarbamoylamino)-8,9-dihydro-7H-cyclopenta[h]isoquinolin-7-yl]pyridine-3-carboxamide;

N-[trans-(7RS,9RS)-9-[(2-chloro-6-methylphenyl)carbamoylamino]-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-9-(methanesulfonamido)-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(2-methylpropylsulfonylamino)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(pyridin-3-ylsulfonylamino)-8,9-dihydro-7H-cyclopenta[h]isoquinolin-7-yl]pyridine-3-carboxamide;

5-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]amino]pyridine-3-carboxylic acid;

1-pyridin-3-yl-3-[cis-(7RS,9SR)-3-cyclopropyl-5-(2-methylpropylsulfamoyl)-7-(pyridin-3-ylcarbamoylamino)-8,9-dihydro-7H-cyclopenta[h]isoquinolin-9-yl]urea;

cis-(7RS,9SR)-3-cyclopropyl-7,9-bis[(5-methoxypyridin-3-yl)amino]-N-(2-methylpropyl)-8,9-dihydro-7H-cyclopenta[h]isoquinoline-5-sulfonamide;

cis-(7RS,9SR)-7-amino-3-cyclopropyl-9-[(5-methoxypyridin-3-yl)amino]-N-(2-methylpropyl)-8,9-dihydro-7H-cyclopenta[h]isoquinoline-5-sulfonamide;

cis-(7RS,9SR)-7,9-bis(1H-benzimidazol-2-ylamino)-3-cyclopropyl-N-(2-methylpropyl)-8,9-dihydro-7H-cyclopenta[h]isoquinoline-5-sulfonamide;

1-ethyl-3-[cis-(7RS,9SR)-3-cyclopropyl-7-(ethylcarbamothioylamino)-5-(2-methylpropylsulfamoyl)-8,9-dihydro-7H-cyclopenta[h]isoquinolin-9-yl]thiourea;

cis-(7RS,9SR)-3-cyclopropyl-N-(2-methylpropyl)-7,9-bis[(4-pyridin-3-yl-1,2,4-triazol-3-yl)amino]-8,9-dihydro-7H-cyclopenta[h]isoquinoline-5-sulfonamide;

trans-(7RS,9RS)-3-cyclopropyl-7,9-bis[(5-methoxypyridin-3-yl)amino]-N-(2-methylpropyl)-8,9-dihydro-7H-cyclopenta[h]isoquinoline-5-sulfonamide;

trans-(7RS,9RS)-7,9-bis(1H-benzimidazol-2-ylamino)-3-cyclopropyl-N-(2-methylpropyl)-8,9-dihydro-7H-cyclopenta[h]isoquinoline-5-sulfonamide;

trans-(7RS,9RS)-3-cyclopropyl-7,9-bis[(4-ethyl-1,2,4-triazol-3-yl)amino]-N-(2-methylpropyl)-8,9-dihydro-7H-cyclopenta[h]isoquinoline-5-sulfonamide;

trans-(7RS,9RS)-3-cyclopropyl-7,9-bis[3-(ethylamino)-1,2,4-triazol-4-yl]-N-(2-methylpropyl)-8,9-dihydro-7H-cyclopenta[h]isoquinoline-5-sulfonamide;

1-ethyl-3-[trans-(7RS,9RS)-3-cyclopropyl-7-(ethylcarbamoylamino)-5-[(2-fluoro-2-methylpropyl)sulfamoyl]-8,9-dihydro-7H-cyclopenta[h]isoquinolin-9-yl]urea;

trans-(7RS,9RS)-3-cyclopropyl-7,9-bis[3-(5-methyl-1,3,4-oxadiazol-2-yl)anilino]-N-(2-methylpropyl)-8,9-dihydro-7H-cyclopenta[h]isoquinoline-5-sulfonamide;

tert-butyl N-[trans-(7RS,9RS)-3-cyclopropyl-5-(2-methylpropylsulfamoyl)-9-(2,2,2-trichloroethoxysulfonylamino)-8,9-dihydro-7H-cyclopenta[h]isoquinolin-7-yl]carbamate;

2-cyano-1-ethyl-3-[trans-(7RS,9RS)-3-cyclopropyl-5-(2-methylpropylsulfamoyl)-7-[[rac-(E)-N'-cyano-N-ethylcarbamimidoyl]amino]-8,9-dihydro-7H-cyclopenta[h]isoquinolin-9-yl]guanidine;

1-ethyl-3-[cis-(7RS,9SR)-3-cyclopropyl-7-(ethylcarbamoylamino)-5-[(2-fluoro-2-methylpropyl)sulfamoyl]-8,9-dihydro-7H-cyclopenta[h]isoquinolin-9-yl]urea;

1-pyridin-3-yl-3-[trans-(7RS,9RS)-3-cyclopropyl-5-(2-methylpropylsulfamoyl)-7-(pyridin-3-ylcarbamoylamino)-8,9-dihydro-7H-cyclopenta[h]isoquinolin-9-yl]urea;

1-propan-2-yl-3-[trans-(7RS,9RS)-3-cyclopropyl-5-(2-methylpropylsulfamoyl)-7-(propan-2-ylcarbamoylamino)-8,9-dihydro-7H-cyclopenta[h]isoquinolin-9-yl]urea;

1-pyridin-3-yl-3-[trans-(7RS,9RS)-3-cyclopropyl-5-(2-methylpropylsulfamoyl)-7-(pyridin-3-ylcarbamothioylamino)-8,9-dihydro-7H-cyclopenta[h]isoquinolin-9-yl]thiourea;

5-methyl-N-[trans-(7RS,9RS)-3-cyclopropyl-5-(2-methylpropylsulfamoyl)-9-[(5-methylpyridine-3-carbonyl)amino]-8,9-dihydro-7H-cyclopenta[h]isoquinolin-7-yl]pyridine-3-carboxamide;

6-morpholin-4-yl-N-[trans-(7RS,9RS)-3-cyclopropyl-5-(2-methylpropylsulfamoyl)-9-[(6-morpholin-4-ylpyridine-3-carbonyl)amino]-8,9-dihydro-7H-cyclopenta[h]isoquinolin-7-yl]pyridine-3-carboxamide;

N-[trans-(7RS,9RS)-9-benzamido-3-cyclopropyl-5-(2-methylpropylsulfamoyl)-8,9-dihydro-7H-cyclopenta[h]isoquinolin-7-yl]benzamide;

4-(dimethylamino)-N-[trans-(7RS,9RS)-3-cyclopropyl-9-[[4-(dimethylamino)benzoyl]amino]-5-(2-methylpropylsulfamoyl)-8,9-dihydro-7H-cyclopenta[h]isoquinolin-7-yl]benzamide;

3,3-dimethyl-N-[trans-(7RS,9RS)-3-cyclopropyl-9-(3,3-dimethylbutanoylamino)-5-(2-methylpropylsulfamoyl)-8,9-dihydro-7H-cyclopenta[h]isoquinolin-7-yl]butanamide;

N,N'-(trans-(7RS,9RS)-3-cyclopropyl-5-(N-isobutylsulfamoyl)-8,9-dihydro-7H-cyclopenta[h]isoquinoline-7,9-diyl)diacetamide;

N-[3-cyclopropyl-5-[(2-fluoro-2-methylpropyl)sulfamoyl]-9-(pyridine-3-carbonylamino)-8,9-dihydro-7H-cyclopenta[h]isoquinolin-7-yl]pyridine-3-carboxamide; or N-[9-amino-3-cyclopropyl-5-[(2-fluoro-2-methylpropyl)sulfamoyl]-8,9-dihydro-7H-cyclopenta[h]isoquinolin-7-yl]pyridine-3-carboxamide.

10. A method for the treatment or prevention of disorders caused by IgE, comprising administration to a patient in need thereof a compound according to claim 1 or a pharmaceutically acceptable salt thereof.

11. A method for the treatment or prevention of allergy, non-allergic mast cell responses, type 1 hypersensitivity, urticaria, or familiar sinus inflammation comprising administration to a patient in need thereof a compound according to claim 1 or a pharmaceutically acceptable salt thereof.

12. A method for the treatment or prevention of airway constriction in asthma, local inflammation in eczema, increased mucus secretion in allergic rhinitis, urticaria, or increased vascular permeability comprising administration to a patient in need thereof a compound according to claim 1 or a pharmaceutically acceptable salt thereof.

13. A method for the treatment or prevention of eosinophilic granulomatosis with polyangiitis, aspirin exacerbated respiratory disease, or cutaneous T-cell lymphoma comprising administration to a patient in need thereof a compound according to claim 1 or a pharmaceutically acceptable salt thereof.

14. A pharmaceutical composition comprising a compound of formula (I) according to claim 1 a pharmaceutically acceptable salt thereof in association with a pharmaceutically acceptable carrier.

15. A method for the treatment or prevention of allergy, non-allergic mast cell responses, type 1 hypersensitivity, urticaria, familiar sinus inflammation, eosinophilic granulomatosis with polyangiitis, aspirin exacerbated respiratory disease, or cutaneous T-cell lymphoma, which comprises the administration of a compound according to claim 1 or a pharmaceutically acceptable salt thereof in a therapeutically effective amount to a patient.

16. A compound according to claim 2 wherein R4 represents cyclopropyl.

17. A compound according to claim 1 wherein R1 and R2 represent independently from each other —NH—CO—$Ra^1$ and $Ra^1$ represents Heteroaryl optionally substituted with one or more Halogen; C1-6-alkyl, C1-6-alkoxy; cyano; or heterocycloalkyl; or $Ra^1$ represents —NH-heteroaryl optionally substituted with one or more Halogen; C1-6-alkyl, C1-6-alkoxy; cyano; heterocycloalkyl; or aryl.

18. A compound according to claim 2 wherein R1 represents:

hydroxy; pyridine-carbonylamino; ethylcarbamoylamino; (methoxyphenyl)methylcarbamoylamino; [(bromphenyl) methyl]carbamoylamino;

naphthalenylcarbamoylamino; (methyl-oxazolyl)methyl] carbamoylamino; ethoxycarbonyl-carbamoylamino; [(methoxyphenyl)ethyl]carbonylamino; (cyclopropylethyl)carbamoylamino;

(methyl)cyclopropyl]carbamoylamino; (benzyl)carbamoylamino; (phenyl-cyclopropyl)carbamoylamino; (chromanyl)carbamoylamino; (chlorophenyl)propenoyl]amino;

(methoxypyridine-carbonyl)amino; [(methoxy-oxo-propanoyl)amino]; (benzamidoacetyl)amino;

(chloro-methoxy-thiophene-carbonyl)amino; (ethoxy-oxo-propanoyl)amino;

methylbutanoylamino;

[(chlorophenoxy)acetyl]amino; (methoxypyridinyl) amino; amino; benzimidazolyl-amino;

ethylcarbamothioylamino; (pyridinyl-triazolyl)amino; [(ethyl-triazolyl)amino; (ethylamino)-triazolyl;

ethylcarbamoylamino; (methyl-oxadiazolyl)anilino; tert-butoxycarbonylamino; [N'-cyano-N-ethyl-carbamimidoyl]amino; pyridin-3-yl-carbamoylamino; propan-2-yl-carbamoylamino; (5-methylpyridine-3-carbonyl) amino; (6-morpholin-4-ylpyridine-3-carbonyl)amino; benzamido;

[(dimethylamino)benzoyl]amino; or Dimethylbutanoylamino.

19. A compound according to claim 2 wherein R1 represents:

Hydroxy; pyridine-3-carbonylamino; ethylcarbamoylamino; (4-methoxyphenyl)methylcarbamoylamino; (3-cyanophenyl)carbamoylamino; [(4-bromphenyl) methyl]carbamoylamino; naphthalen-1-ylcarbamoylamino; [(5-methyl-1,2-oxazol-3-yl)methyl]carbamoylamino; ethoxycarbonyl-carbamoylamino; [(1R)-1-(3-methoxyphenyl)ethyl]carbonylamino;

(1-cyclopropylethylcarbamoylamino); 2-(methyl)cyclopropyl]carbamoylamino; (1-benzyl)carbamoylamino; (2-phenyl-cyclopropyl)carbamoylamino; (chroman-3-yl)carbamoylamino; (E)-3-(2-chlorophenyl)prop-2-enoyl]amino; (6-methoxypyridine-3-carbonyl)amino; [(3-methoxy-3-oxo-propanoyl)amino]; (2-benzamidoacetyl)amino; (5-chloro-4-methoxy-thiophene-3-carbonyl)amino; (3-ethoxy-3-oxo-propanoyl) amino; 2-methylbutanoylamino; [2-(4-chlorophenoxy) acetyl]amino; (5-methoxypyridin-3-yl)amino; amino; 1H-benzimidazol-2-ylamino; ethylcarbamothioylamino; (4-pyridin-3-yl-1,2,4-triazol-3-yl)amino; 3-(ethylamino)-1,2,4-triazol-4-yl; 3-(5-methyl-1,3,4-oxadiazol-2-yl)anilino; tert-butoxycarbonylamino; [(Z)—N'-cyano-N-ethyl-carbamimidoyl]amino; propan-2-ylcarbamoylamino; pyridin-3-ylcarbamothioylamino; (5-methylpyridine-3-carbonyl)amino; 6-morpholin-4-ylpyridine-3-carbonyl)amino; benzamido; [4-(dimethylamino)benzoyl]amino; or 3,3-dimethylbutanoylamino.

20. A compound according to claim 2 wherein R2 represents: tert-butoxycarbonyl-amino; amino; pyridylcarbamothioylamino; ethylcarbamoylamino; pyridinyl-amino; (pyridinyl-triazolyl)amino; (pyridinyl-amino)-triazolyl; (ethyl-triazolyl)amino; benzylamino; propylamino; methylpropanoylamino; hydroxy; ethylcarbamoylamino; isoquinolinyl-amino; (methoxypyridinyl)amino; (pyridinyl)carbonylamino; benzimidazolylamino; [(phenyl)-oxazolyl] carbonylamino; quinoxaline-carbonylamino; [(hydroxyphenyl)propenoyl]amino; pyrido-pyrazine-carbonylamino; benzoxazole-carbonylamino; [ethoxy-oxo-butenoyl]amino; (benzimidazolyl)propanoylamino; (oxopyridinyl)propanoylamino; methoxy-benzofuran-carbonyl)amino; (oxopyrrolidinyl)propanoylamino; [(ethoxy-carbonyl-pyridyl)amino]; (methoxyanilino); (cyano-pyridyl)amino; [(methyl-pyridazinyl)amino]; quinolinyl-amino; (methyl-oxazolyl)methyl-carbamoyl-amino; (phenylcyclopropyl)carbamoylamino; [(tert-butoxymethyl-oxo-ethyl)carbamoylamino]; dihydro-2H-chromenylcarbamoylamino; [(methoxyphenyl)ethylcarbamoylamino]; oxanylcarbamoylamino; (chloro-methylphenyl)carbamoylamino; methanesulfonamido; methylpropylsulfonylamino; pyridinylsulfonylamino; [(carboxypyridyl)amino]; pyridylcarbamoylamino; methoxy-pyridinyl)amino; ethyl-carbamothioyl-amino; (pyridinyl-triazolyl)amino; (methoxy-pyridinyl)amino; [(ethyl-triazolyl)amino(ethylamino)-triazolyl; (methyl-oxadiazolyl)anilino; trichloroethoxysulfonylamino; [(Z)—N'-cyano-N-ethyl-carbamimidoyl]amino; pyridinylcarbamoylamino; propanyl-carbamoylamino; pyridinylcarbamothioylamino; methylpyridinecarbonyl)amino; (morpholinylpyridinecarbonyl) amino; Benzamido; [(dimethylamino)benzoyl]amino; or dimethylbutanoylamino.

* * * * *